US011351387B2

(12) United States Patent
Stevenson et al.

(10) Patent No.: US 11,351,387 B2
(45) Date of Patent: Jun. 7, 2022

(54) METHOD OF MANUFACTURING A SINGULATED FEEDTHROUGH INSULATOR FOR A HERMETIC SEAL OF AN ACTIVE IMPLANTABLE MEDICAL DEVICE INCORPORATING A POST CONDUCTIVE PASTE FILLED PRESSING STEP

(71) Applicant: Greatbatch Ltd., Clarence, NY (US)

(72) Inventors: Robert A. Stevenson, Canyon Country, CA (US); Thomas Marzano, East Amherst, NY (US); Keith W. Seitz, Clarence Center, NY (US); Christine A. Frysz, Orchard Park, NY (US); Dallas J. Rensel, Sanborn, NY (US); Brian P. Hohl, Clarence, NY (US)

(73) Assignee: Greatbatch Ltd., Clarence, NY (US)

( * ) Notice: Subject to any disclaimer, the term of this patent is extended or adjusted under 35 U.S.C. 154(b) by 290 days.

(21) Appl. No.: 16/578,476

(22) Filed: Sep. 23, 2019

(65) Prior Publication Data
US 2020/0030613 A1     Jan. 30, 2020

Related U.S. Application Data

(63) Continuation of application No. 16/101,639, filed on Aug. 13, 2018, now Pat. No. 10,420,949, which is a
(Continued)

(51) Int. Cl.
*A61N 1/37* (2006.01)
*A61N 1/375* (2006.01)
(Continued)

(52) U.S. Cl.
CPC .............. *A61N 1/3754* (2013.01); *A61N 1/05* (2013.01); *A61N 1/08* (2013.01); *B23K 35/3013* (2013.01);
(Continued)

(58) Field of Classification Search
CPC .......... A61N 1/3754; A61N 1/05; A61N 1/08; B23K 35/3013; H01G 2/103; H01G 4/005; H01G 4/12; H01G 4/30; H01G 4/35
See application file for complete search history.

(56) References Cited

U.S. PATENT DOCUMENTS

| 3,137,808 A | 6/1964 | Coda et al. |
| 3,189,978 A | 6/1965 | Stetson |

(Continued)

FOREIGN PATENT DOCUMENTS

| EP | 0697725 | 2/1996 |
| EP | 2392382 | 12/2011 |

OTHER PUBLICATIONS

European Search Report, Application No. 13151535.5, dated Jul. 22, 2013.
(Continued)

*Primary Examiner* — Jeffrey T Carley
(74) *Attorney, Agent, or Firm* — Michael F. Scalise

(57) ABSTRACT

A method for manufacturing a singulated feedthrough insulator for a hermetic seal of an active implantable medical device (AIMD) is described. The method begins with forming a green-state ceramic bar with a via hole filled with a conductive paste. The green-state ceramic bar is dried to convert the paste to an electrically conductive material filling via hole and then subjected to a pressing step. Following pressing, a green-state insulator is singulated from the green-state ceramic bar. The singulated green-state insulator in next sintered to form an insulator that is sized and shaped for hermetically sealing to close a ferrule opening. The thusly produced feedthrough is suitable installation in an opening in the housing of an active implantable medical device.

28 Claims, 56 Drawing Sheets

Related U.S. Application Data continuation-in-part of application No. 15/164,945, filed on May 26, 2016, now Pat. No. 10,046,166, which is a continuation-in-part of application No. 14/864,959, filed on Sep. 25, 2015, now Pat. No. 9,352,150, which is a continuation of application No. 13/743,276, filed on Jan. 16, 2013, now Pat. No. 9,233,253.

(60) Provisional application No. 61/587,373, filed on Jan. 17, 2012, provisional application No. 61/587,287, filed on Jan. 17, 2012, provisional application No. 61/587,029, filed on Jan. 16, 2012.

(51) Int. Cl.

| | | |
|---|---|---|
| *A61N 1/05* | (2006.01) | |
| *B23K 35/30* | (2006.01) | |
| *A61N 1/08* | (2006.01) | |
| *H01R 43/00* | (2006.01) | |
| *H01G 4/35* | (2006.01) | |
| *C22C 29/12* | (2006.01) | |
| *H01G 4/12* | (2006.01) | |
| *H01G 2/10* | (2006.01) | |
| *H01G 4/005* | (2006.01) | |
| *H02G 3/22* | (2006.01) | |
| *H01G 4/30* | (2006.01) | |
| *C04B 37/02* | (2006.01) | |
| *C04B 35/645* | (2006.01) | |
| *B32B 18/00* | (2006.01) | |
| *H01G 4/40* | (2006.01) | |
| *A61N 1/372* | (2006.01) | |
| *B22F 7/04* | (2006.01) | |
| *B22F 3/04* | (2006.01) | |
| *B22F 3/02* | (2006.01) | |
| *B22F 3/15* | (2006.01) | |
| *C04B 35/00* | (2006.01) | |
| *C22C 1/04* | (2006.01) | |

(52) U.S. Cl.
CPC ............ *B32B 18/00* (2013.01); *C04B 35/645* (2013.01); *C04B 37/026* (2013.01); *C22C 29/12* (2013.01); *H01G 2/103* (2013.01); *H01G 4/005* (2013.01); *H01G 4/12* (2013.01); *H01G 4/30* (2013.01); *H01G 4/35* (2013.01); *H01R 43/00* (2013.01); *H02G 3/22* (2013.01); *A61N 1/372* (2013.01); *A61N 1/375* (2013.01); *B22F 3/02* (2013.01); *B22F 3/04* (2013.01); *B22F 3/15* (2013.01); *B22F 2007/042* (2013.01); *B22F 2999/00* (2013.01); *C04B 35/00* (2013.01); *C04B 2237/122* (2013.01); *C04B 2237/125* (2013.01); *C04B 2237/343* (2013.01); *C04B 2237/403* (2013.01); *C04B 2237/72* (2013.01); *C22C 1/0466* (2013.01); *H01G 4/40* (2013.01); *Y10T 156/1052* (2015.01)

(56) References Cited

U.S. PATENT DOCUMENTS

| | | | |
|---|---|---|---|
| 3,617,830 A | 11/1971 | Perna | |
| 4,424,551 A | 1/1984 | Stevenson et al. | |
| 5,272,283 A | 12/1993 | Kuzma | |
| 5,333,095 A | 7/1994 | Stevenson et al. | |
| 5,365,928 A | 11/1994 | Rhinehart et al. | |
| 5,434,358 A | 7/1995 | Glahn et al. | |
| 5,470,345 A | 11/1995 | Hassler et al. | |
| 5,620,476 A | 4/1997 | Truex et al. | |
| 5,623,724 A | 4/1997 | Gurkovich et al. | |
| 5,650,759 A | 7/1997 | Hittman et al. | |
| 5,700,548 A | 12/1997 | Warnier et al. | |
| 5,735,884 A | 4/1998 | Thompson et al. | |
| 5,751,539 A | 5/1998 | Stevenson et al. | |
| 5,782,891 A | 7/1998 | Hassler et al. | |
| 5,855,995 A * | 1/1999 | Haq | A61N 1/02 428/210 |
| 5,896,267 A | 4/1999 | Hittman et al. | |
| 5,905,627 A | 5/1999 | Brendel et al. | |
| 5,959,829 A | 9/1999 | Stevenson et al. | |
| 5,973,906 A | 10/1999 | Stevenson et al. | |
| 6,008,980 A | 12/1999 | Stevenson et al. | |
| 6,041,496 A | 3/2000 | Haq et al. | |
| 6,146,743 A | 11/2000 | Haq et al. | |
| 6,159,560 A | 12/2000 | Stevenson et al. | |
| 6,252,761 B1 | 6/2001 | Branchevsky | |
| 6,275,379 B1 | 8/2001 | Sleboda et al. | |
| 6,284,080 B1 | 9/2001 | Haq et al. | |
| 6,414,835 B1 | 7/2002 | Wolf et al. | |
| 6,456,481 B1 | 9/2002 | Stevenson | |
| 6,470,545 B1 | 10/2002 | Branchevsky | |
| 6,529,103 B1 | 3/2003 | Brendel et al. | |
| 6,566,978 B2 | 5/2003 | Stevenson et al. | |
| 6,567,259 B2 | 5/2003 | Stevenson et al. | |
| 6,643,903 B2 | 11/2003 | Stevenson et al. | |
| 6,660,116 B2 | 12/2003 | Wolf | |
| 6,694,583 B2 | 2/2004 | Branchevsky | |
| 6,765,779 B2 | 7/2004 | Stevenson et al. | |
| 6,765,780 B2 | 7/2004 | Brendel et al. | |
| 6,888,715 B2 | 5/2005 | Stevenson et al. | |
| 6,985,347 B2 | 1/2006 | Stevenson et al. | |
| 6,987,660 B2 | 1/2006 | Stevenson et al. | |
| 6,999,818 B2 | 2/2006 | Stevenson et al. | |
| 7,012,192 B2 | 3/2006 | Stevenson et al. | |
| 7,035,076 B1 | 4/2006 | Stevenson | |
| 7,038,900 B2 | 5/2006 | Stevenson et al. | |
| 7,068,491 B1 | 6/2006 | Burdon et al. | |
| 7,113,387 B2 | 9/2006 | Stevenson et al. | |
| 7,136,273 B2 | 11/2006 | Stevenson et al. | |
| 7,164,572 B1 | 1/2007 | Burdon et al. | |
| 7,199,995 B2 | 4/2007 | Stevenson | |
| 7,310,216 B2 | 12/2007 | Stevenson et al. | |
| 7,327,553 B2 | 2/2008 | Brendel | |
| 7,480,988 B2 | 1/2009 | Ok et al. | |
| 7,489,495 B2 | 2/2009 | Stevenson | |
| 7,535,693 B2 | 5/2009 | Stevenson et al. | |
| 7,551,963 B2 | 6/2009 | Rusin et al. | |
| 7,623,335 B2 | 11/2009 | Stevenson et al. | |
| 7,679,926 B2 | 3/2010 | Hsu et al. | |
| 7,693,576 B1 | 4/2010 | Lavie et al. | |
| 7,719,854 B2 | 5/2010 | Youker et al. | |
| 7,797,048 B2 | 9/2010 | Stevenson et al. | |
| 7,812,691 B1 | 10/2010 | Fisk et al. | |
| 7,901,761 B1 * | 3/2011 | Jiang | H05K 1/092 428/210 |
| 7,957,806 B2 | 6/2011 | Stevenson et al. | |
| 7,989,080 B2 | 8/2011 | Greenberg et al. | |
| 8,000,804 B1 | 8/2011 | Wessendorf et al. | |
| 8,043,454 B1 | 10/2011 | Jiang et al. | |
| 8,095,224 B2 | 1/2012 | Truex et al. | |
| 8,163,397 B2 | 4/2012 | Ok et al. | |
| 8,179,658 B2 | 5/2012 | Stevenson et al. | |
| 8,763,245 B1 | 7/2014 | Lucisano et al. | |
| 9,233,253 B2 | 1/2016 | Stevenson et al. | |
| 2002/0027282 A1 | 3/2002 | Kawakami et al. | |
| 2002/0139556 A1 * | 10/2002 | Ok | H05K 3/4046 174/50.6 |
| 2003/0179536 A1 * | 9/2003 | Stevenson | H01G 4/35 361/302 |
| 2003/0213605 A1 | 11/2003 | Brendel et al. | |
| 2005/0190527 A1 | 9/2005 | Stevenson et al. | |
| 2005/0195556 A1 | 9/2005 | Shah | |
| 2006/0229693 A1 | 10/2006 | Bauer et al. | |
| 2006/0259093 A1 | 11/2006 | Stevenson et al. | |
| 2007/0060969 A1 | 3/2007 | Burdon et al. | |
| 2007/0060970 A1 | 3/2007 | Burdon et al. | |
| 2007/0236861 A1 | 10/2007 | Burdon et al. | |

(56) References Cited

U.S. PATENT DOCUMENTS

| | | | |
|---|---|---|---|
| 2008/0314502 A1* | 12/2008 | Ok | H05K 3/4061 |
| | | | 156/89.16 |
| 2009/0097219 A1 | 4/2009 | Cho et al. | |
| 2009/0243756 A1 | 10/2009 | Stevenson et al. | |
| 2009/0259265 A1 | 10/2009 | Stevenson et al. | |
| 2010/0023086 A1 | 1/2010 | Lim | |
| 2010/0160991 A1 | 6/2010 | Lim | |
| 2010/0234907 A1 | 9/2010 | Dobak | |
| 2011/0000699 A1 | 1/2011 | Bealka et al. | |
| 2011/0034965 A1 | 2/2011 | Troetzschel et al. | |
| 2011/0048990 A1 | 3/2011 | Goda | |
| 2011/0102967 A1 | 5/2011 | Munns et al. | |
| 2011/0106205 A1* | 5/2011 | Reiterer | H01G 4/35 |
| | | | 607/37 |
| 2011/0248184 A1* | 10/2011 | Shah | A61B 5/1459 |
| | | | 250/458.1 |
| 2012/0193117 A1 | 8/2012 | Specht et al. | |
| 2012/0197327 A1* | 8/2012 | Specht | H01R 13/5224 |
| | | | 607/5 |

OTHER PUBLICATIONS

European Search Report, Application No. 13151536.3, dated Jun. 13, 2013.
European Search Report, Application No. 13151537.1, dated Jun. 24, 2013.
European Search Report, Application No. 13151537.1, dated Jul. 11, 2013.
Lu, et al., "Pt-Al2O3 interfacial bonding in implantable hermetic feedthroughs: Morphology and orientation", Society tor Biomaterial—2011 Wiley Periodicals, Inc., Dec. 24, 2011, 817-824.

* cited by examiner

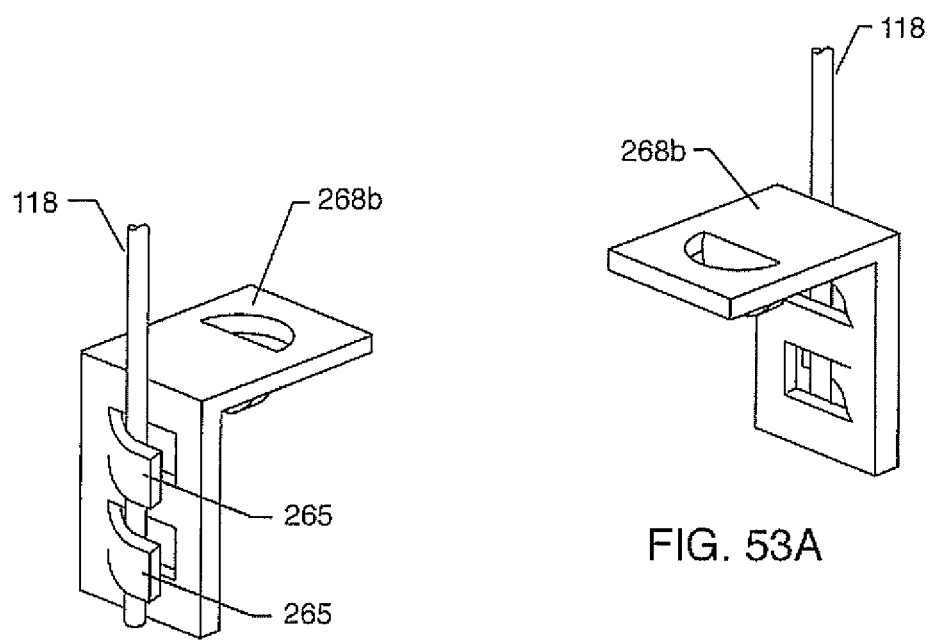
FIG. 53
FIG. 53A
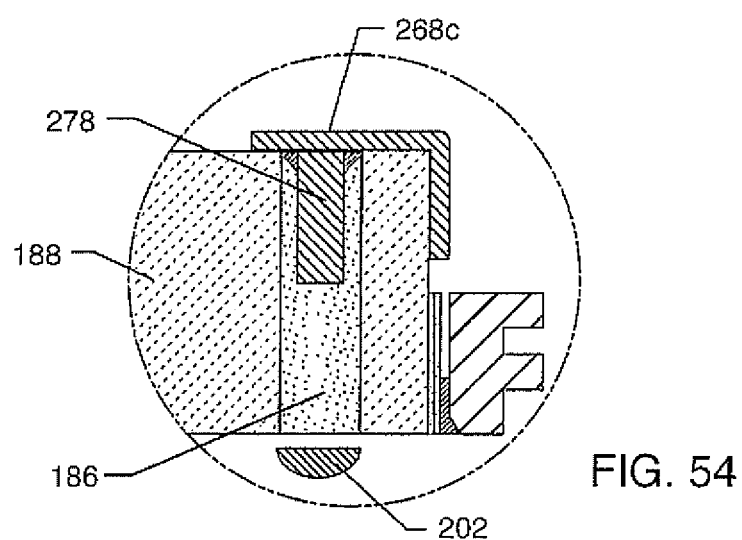
FIG. 54

(BEFORE PRESSING)

(AFTER PRESSING)

METHOD OF MANUFACTURING A SINGULATED FEEDTHROUGH INSULATOR FOR A HERMETIC SEAL OF AN ACTIVE IMPLANTABLE MEDICAL DEVICE INCORPORATING A POST CONDUCTIVE PASTE FILLED PRESSING STEP

CROSS-REFERENCE TO RELATED APPLICATIONS

The present application is a continuation of U.S. patent application Ser. No. 16/101,639, filed on Aug. 13, 2018, now U.S. Pat. No. 10,420,949, which is a continuation-in-part of U.S. patent application Ser. No. 15/164,945, filed on May 26, 2016, now U.S. Pat. No. 10,046,166, which is a continuation-in-part of U.S. patent application Ser. No. 14/864,959, filed on Sep. 25, 2015, now U.S. Pat. No. 9,352,150, which is a continuation of U.S. patent application Ser. No. 13/743,276, filed on Jan. 16, 2013, now U.S. Pat. No. 9,233,253, which claimed priority to U.S. provisional application Ser. Nos. 61/587,029, filed on Jan. 16, 2012; 61/587,287, filed on Jan. 17, 2012; and 61/587,373, filed on Jan. 17, 2012. The contents of all of the applications referenced above are fully incorporated herein with these references.

FIELD OF THE INVENTION

The present invention generally relates to implantable medical devices and hermetic terminal subassemblies. More particularly, the present invention relates to a hermetic terminal subassembly utilizing a novel way of making a three-way connection between a conductively filled via of an insulator, an internal metallization of a feedthrough filter capacitor and a leadwire extending to electronics inside the implantable medical devices.

BACKGROUND OF THE INVENTION

A wide assortment of active implantable medical devices (AIMD) are presently known and in commercial use. Such devices include cardiac pacemakers, cardiac defibrillators, cardioverters, neurostimulators, and other devices for delivering and/or receiving electrical signals to/from a portion of the body. Sensing and/or stimulating leads extend from the associated implantable medical device to a distal tip electrode or electrodes in contact with body tissue.

The hermetic terminal or feedthrough of these implantable devices is considered critical. Hermetic terminals or feedthroughs are generally well-known in the art for connecting electrical signals through the housing or case of an AIMD. For example, in implantable medical devices such as cardiac pacemakers, implantable cardioverter defibrillators, and the like, a hermetic terminal comprises one or more conductive terminal pins supported by an insulative structure for feedthrough passage from the exterior to the interior of an AIMD electromagnetic shield housing. Hermetic terminals or feedthroughs for AIMDs must be biocompatible as well as resistant to degradation under applied bias current or voltage. Hermeticity of the feedthrough is imparted by judicious material selection and carefully prescribed manufacturing processing. Sustainable hermeticity of the feedthrough over the lifetime of these implantable devices is critical because the hermetic terminal intentionally isolates the internal circuitry and components of the device from the external environment to which the component is exposed. In particular, the hermetic terminal isolates the internal circuitry, connections, power sources and other components in the device from ingress of body fluids. Ingress of body fluids into an implantable medical device is known to be a contributing factor to device malfunction and may contribute to the compromise or failure of electrical circuitry, connections, power sources and other components within an implantable medical device that are necessary for consistent and reliable device therapy delivery to a patient. Furthermore, ingress of body fluids may compromise an implantable medical device's functionality which may constitute electrical shorting, element or joint corrosion, metal migration or other such harmful consequences affecting consistent and reliable device therapy delivery.

In addition to concerns relative to sustained terminal or feedthrough hermeticity, other potentially compromising conditions must be addressed, particularly when a hermetic terminal or feedthrough is incorporated within an implantable medical device. For example, the hermetic terminal or feedthrough pins are typically connected to one or more leadwires of implantable therapy delivery leads. These implantable therapy delivery leads can effectively act as antennas of electromagnetic interference (EMI) signals. Therefore, when these electromagnetic signals enter within the interior space of a hermetic implantable medical device, facilitated by the therapy delivery leads, they can negatively impact the intended function of the medical device and as a result, negatively impact therapy delivery intended for a patient by that device. EMI engineers commonly refer to this as the "genie in the bottle" effect. In other words, once the genie (i.e., EMI) is inside the hermetic device, it can wreak havoc with electronic circuit functions by cross-coupling and re-radiating within the device.

Another particularly problematic condition associated with implanted therapy delivery leads occurs when a patient is in an MRI environment. In this case, the electrical currents imposed on the implanted therapy delivery leads can cause the leads to heat to the point where tissue damage is likely. Moreover, the electrical currents developed in these implanted therapy delivery leads during an MRI procedure can disrupt or damage the sensitive electronics within the implantable medical device.

Therefore, materials selection and fabrication processing parameters are of utmost importance in creating a hermetic terminal (or feedthrough) or a structure embodying a hermetic terminal (or feedthrough), that can survive anticipated and possibly catastrophically damaging environmental conditions and that can be practically, and cost effectively manufactured.

Hermetic terminals or feedthrough assemblies utilizing ceramic dielectric materials may fail in a brittle manner. A brittle failure typically occurs when the ceramic structure is deformed elastically up to an intolerable stress, at which point the ceramic fails catastrophically. Virtually all brittle failures occur by crack propagation in a tensile stress field. Even microcracking caused by sufficiently high tensile stress concentrations may result in a catastrophic failure including loss of hermeticity identified as critical in hermetic terminals for implantable medical devices. Loss of hermeticity may be a result of design aspects such as a sharp corner which creates a stress riser, mating materials with a difference of coefficient of thermal expansions (CTE) that generate tensile stresses that ultimately result in loss of hermeticity of the feedthrough or interconnect structure.

In the specific case of hermetic terminal or feedthrough designs, a tensile stress limit for a given ceramic based hermetic design structure cannot be specified because failure stress in these structures is not a constant. As indicated above, variables affecting stress levels include the design itself, the materials selection, symmetry of the feedthrough, and the bonding characteristics of mating surfaces within the feedthrough. Hence, length, width and height of the overall ceramic structure matters as do the number, spacing, length and diameter of the vias in that structure. The selection of the mating materials, that is, the material that fills the vias and the material that forms the base ceramic, are important. Finally, the fabrication processing parameters, particularly at binder burnout, sintering and cool down, make a difference. When high reliability is required in an application such as indicated with hermetic terminals or feedthroughs for AIMDs, to provide ensurance for a very low probability of failure it is necessary to design a hermetic terminal assembly or feedthrough structure so that stresses imparted by design, materials and/or processing are limited to a smaller level of an average possible failure stress. Further, to provide ensurance for a very low probability of failure in a critical ceramic-based assembly or subassembly having sustainable hermetic requirements, it is also necessary to design structures embodying a hermetic terminal or feedthrough such that stresses in the final assembly or subassembly are limited to a smaller level of an average possible failure stress for the entire assembly or subassembly. In hermetic terminals and structures comprising hermetic terminals for AIMDs wherein the demand for biocompatibility exists, this task becomes even more difficult.

The most critical feature of a feedthrough design or any terminal subassembly is the metal/ceramic interface within the feedthrough that establishes the hermetic seal. The present invention therefore, provides a hermetic feedthrough comprising a monolithic alumina insulator substrate within which a platinum conductive pathway or via resides. More specifically, the present invention provides a hermetic feedthrough in which the hermetic seal is created through the intimate bonding of the platinum metal residing within the alumina substrate.

A traditional ceramic-to-metal hermetic terminal is an assembly of three components: metal leadwires that conduct electrical current, a ceramic insulator, and a metal housing, which is referred to as the flange or the ferrule. Brazed joints hermetically seal the metal leadwires and the flange or ferrule to the ceramic insulator. For a braze-bonded joint, the braze material is generally intended to deform in a ductile manner in order to compensate for perturbations that stress the bond between the mating materials as the braze material may provide ductile strain relief when the thermal expansion mismatch between the ceramic and metal is large. Thus, mating materials with large mismatches in CTE can be coupled through braze materials whose high creep rate and low yield strength reduce the stresses generated by the differential contraction existing between these mating materials.

Thermal expansion of metal is generally considerably greater than those of ceramics. Hence, successfully creating a hermetic structure, and one that can sustain its hermeticity in service, is challenging due to the level of residual stresses in the final structure. Specifically, thermal expansion mismatch results in stresses acting along the ceramic/metal interface that tend to separate the ceramic from the metal and so the bond developed between the ceramic and the metal must be of sufficient strength to withstand these stresses, otherwise adherence failure, that is, loss of hermeticity, will occur. One method for limiting these stresses is to select combinations of materials whose thermal contractions after bonding are matched.

In making the selection for a CTE match, it is important to note that very few pairs of materials have essentially identical thermal expansion curves. Generally, the metal component is selected first based on electrical and thermal conductivity, thermal expansion, ability to be welded or soldered, mechanical strength, and chemical resistance or biocompatibility requirements; the ceramic is then selected based primarily on electrical resistivity, dielectric strength, low gas permeability, environmental stability, and thermal expansion characteristics. In the specific case of selecting platinum wire, often the ceramic formulation is modified in order to match its CTE to that of the platinum wire. In yet a more specific case of selecting platinum paste, the platinum paste formulation may be modified as well. If the mating materials are alumina of at least 96% purity and essentially pure platinum paste, then matching CTE is not possible. Thus, for AIMD's, consistently achieving hermetic terminal structures that are capable of sustaining hermeticity throughout the application's service life has proven challenging.

Producing a stress-free structure often not only involves bonding a pair of materials but also achieving that bond at a very specific temperature so that their contractions on cooling to room temperature are essentially the same even though the contraction curves may not coincide. Since this often is a significant challenge, hermetic terminals are produced by metalizing the alumina and using a brazing material to form the bond at some other temperature than an intersection of the CTE curves. (NOTE: Forming a bond between two materials that become rigid at the intersection of the two CTE curves makes it possible to produce a structure that is stress free at room temperature, unless the two CTE curves separate substantially from each other from the intersection point and room temperature.) The deformation of the braze material by time-independent plastic flow or creep relaxation limits the stresses generated in the ceramic. Given this, the impact of the rate of cooling on the final stress level of a structure must also be considered. In some cases, residual stresses are generated deliberately to provide protective compressive stresses in the ceramic part and in the bond interface. Usually this is accomplished by selecting components with different CTEs. Another way is to control the shrinkage of one material over its mating material. In either case, it is important to minimize stress levels such that the interface on which hermeticity depends is well within the stress level at which failure might occur.

In an embodiment, the present invention is directed to mating bound particulate high purity alumina of at least 96% and particles of essentially pure platinum metal that are suspended within a mixture of solvents and binders, i.e. a platinum paste. This combination of materials does not use a braze material to buffer the CTE mismatch between these two materials. Further, since the intent of this invention is to provide hermetic terminals and subassemblies comprising hermetic terminals for AIMDs, the present invention does not consider modifications to the alumina formulation or the platinum paste in an attempt to match their CTEs. Rather, this invention discloses sustainable hermetic terminals and structures embodying these hermetic terminals. This is achieved by adjusting platinum paste solids loading, prescribing via packing, prescribing binder burnout, sintering and cool down parameters, such that shrinkage of the alumina is greater than the shrinkage of the platinum fill in the via and an intimate and tortuous (a mutually conformal) interface is created that may be either a direct bond between the alumina and platinum materials that is hermetic; or, alternatively, that may develop an amorphous interfacial layer that is not susceptible to erosion by body fluids and can tolerate stress levels without losing hermeticity. As used herein, the terms binder burnout, binder bake out, and drying are synonymous and can be used interchangeably. Binder burnout, binder bake out or drying herein refer to the removal of the binder materials from the alumina and the conductive filled vias, which may be performed by waiting a period of time, heating at an elevated temperature and/or placing within a vacuum.

Regarding EMI, a terminal or feedthrough capacitor EMI filter may be disposed at, near or within a hermetic terminal or feedthrough resulting in a feedthrough filter capacitor which diverts high frequency electrical signals from lead conductors to the housing or case of an AIMD. Many different insulator structures and related mounting methods are known in the art for use of feedthrough capacitor EMI filters in AIMDs, wherein the insulative structure also provides a hermetic terminal or feedthrough to prevent entry of body fluids into the housing of an AIMD. In the prior art devices, the hermetic terminal subassembly has been combined in various ways with a ceramic feedthrough filter EMI capacitor to decouple interference signals to the housing of the medical device.

In a typical prior art unipolar construction (as described in U.S. Pat. No. 5,333,095 and herein incorporated by reference), a round/discoidal (or rectangular) ceramic feedthrough EMI filter capacitor is combined with a hermetic terminal pin assembly to suppress and decouple undesired interference or noise transmission along a terminal pin. The feedthrough capacitor is coaxial having two sets of electrode plates embedded in spaced relation within an insulative dielectric substrate or base, formed typically as a ceramic monolithic structure. One set of the electrode plates are electrically connected at an inner diameter cylindrical surface of the coaxial capacitor structure to the conductive terminal pin utilized to pass the desired electrical signal or signals. The other or second set of electrode plates are coupled at an outer diameter surface of the round/discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the coaxial capacitor. The outer feedthrough capacitor electrode plate sets (or "ground" plates) are coupled in parallel together by a metalized layer which is either fired, sputtered or plated onto the ceramic capacitor. This metalized band, in turn, is coupled to the ferrule by conductive adhesive, soldering, brazing, welding, or the like. The inner feedthrough capacitor electrode plate sets (or "active" plates) are coupled in parallel together by a metalized layer which is either glass frit fired or plated onto the ceramic capacitor. This metalized band, in turn, is mechanically and electrically coupled to the lead wire(s) by conductive adhesive, soldering, or the like. In operation, the coaxial capacitor permits passage of relatively low frequency biologic signals along the terminal pin, while shielding and decoupling/attenuating undesired interference signals of typically high frequency to the AIMD conductive housing. Feedthrough capacitors of this general type are available in unipolar (one), bipolar (two), tripolar (three), quadpolar (four), pentapolar (five), hexpolar (6) and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the ferrule of the hermetic terminal pin assembly which is in turn electrically coupled to the coaxial feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

Regarding MRI related issues, bandstop filters, such as those described in U.S. Pat. No. 6,008,980, which is herein incorporated by reference, reduce or eliminate the transmission of damaging frequencies along the leads while allowing the desired biologic frequencies to pass efficiently through.

Referring once again to feedthrough capacitor EMI filter assemblies, although these assemblies as described earlier have performed in a generally satisfactory manner, and notwithstanding that the associated manufacturing and assembly costs are unacceptably high in that the choice of the dielectric material for the capacitor has significant impacts on cost and final performance of the feedthrough filter capacitor, alumina ceramic has not been used in the past as the dielectric material for AIMD feedthrough capacitors. Alumina ceramic is structurally strong and biocompatible with body fluids but has a dielectric constant around 6 (less than 10). There are other more effective dielectric materials available for use in feedthrough filter capacitor designs. Relatively high dielectric constant materials (for example, barium titanate with a dielectric constant of over 2,000) are traditionally used to manufacture AIMD feedthrough capacitors for integrated ceramic capacitors and hermetic seals resulting in more effective capacitor designs. Yet ceramic dielectric materials such as barium titanate are not as strong as the alumina ceramic typically used to manufacture the hermetic seal subassembly in the prior art. Barium titanate is also not biocompatible with body fluids. Direct assembly of the ceramic capacitor can result in intolerable stress levels to the capacitor due to the mismatch in thermal coefficients of expansion between the titanium pacemaker housing (or other metallic structures) and the capacitor dielectric. Hence, particular care must be used to avoid cracking of the capacitor element. Accordingly, the use of dielectric materials with a low dielectric constant and a relatively high modulus of toughness are desirable yet still difficult to achieve for capacitance-efficient designs.

Therefore, it is very common in the prior art to construct a hermetic terminal subassembly with a feedthrough capacitor attached near the inside of the AIMD housing on the device side. The feedthrough capacitor does not have to be made from biocompatible materials because it is located on the device side inside the AIMD housing. The hermetic terminal subassembly allows leadwires to hermetically pass through the insulator in non-conductive relation with the ferrule or the AIMD housing. The leadwires also pass through the feedthrough capacitor to the inside of the AIMD housing. These leadwires are typically continuous and must be biocompatible and non-toxic. Generally, these leadwires are constructed of platinum or platinum-iridium, palladium or palladium-iridium, niobium or the like. Platinum-iridium is an ideal choice because it is biocompatible, non-toxic and is also mechanically very strong. The iridium is added to enhance material stiffness and to enable the hermetic terminal subassembly leadwire to sustain bending stresses. An issue with the use of platinum for leadwires is that platinum has become extremely expensive and may be subject to premature fracture under rigorous processing such as ultrasonic cleaning or application use/misuse, possibly unintentional damaging forces resulting from Twiddler's Syndrome.

Accordingly, what is needed is a filtered structure like a hermetic terminal or feedthrough, any subassembly made using same and any feedthrough filter EMI capacitor assembly which minimizes intolerable stress levels, allows use of preferred materials for AIMDS and eliminates high-priced, platinum, platinum-iridium or equivalent noble metal hermetic terminal subassembly leadwires. Also, what is needed is an efficient, simple and robust way to connect the leadwires in a header block to the novel hermetic terminal subassembly. Correspondingly, it is also needed to make a similar efficient, simple and robust electrical connection between the electronics on the device side of the AIMD to the feedthrough capacitor and hermetic terminal subassembly. The present invention fulfills these needs and provides other related advantages.

SUMMARY OF THE INVENTION

An exemplary embodiment of the present invention is for a method of manufacturing a feedthrough dielectric body for an active implantable medical device, the method comprising the steps of: a) forming a ceramic body (alumina substrate 188) in a green state (FIG. 88), or, stacking discrete layers of ceramic in a green state upon one another and laminating to form the ceramic body in the green state (FIG. 88), the ceramic body having a first side opposite a second side; b) forming at least one via hole straight through the ceramic body extending between the first and second sides; c) filling the at least one via hole with a conductive paste (comprising a platinum conductor 186); d) drying the ceramic body and the conductive paste; e) pressing (301 in FIG. 87) the ceramic body and the conductive paste; f) sintering the ceramic body and the conductive paste together to form the feedthrough dielectric body; and g) hermetically sealing (gold braze 140 in FIG. 84) the feedthrough dielectric body to a ferrule (122), the ferrule configured to be installed in an opening of a housing of the active implantable medical device. The first and second sides are also known by those skilled in the art as the body fluid side and device side, as the body fluid side is the side that eventually is exposed to body fluids and the device side is the side that is inside the AIMD housing.

In other exemplary embodiments thereof, the pressing step e) may comprise an isostatic pressing or may comprise a hot pressing, a cold pressing, a die pressing or a mechanical pressing.

The isostatic pressing may be greater than or equal to 1000 psi of pressure, and/or the isostatic pressing may be between 1000 psi and 50,000 psi of pressure. Furthermore, the isostatic pressing may be performed at a temperature equal to or above 55° C. and/or may be held at pressure for at least 5 minutes.

The hermetically sealing step g) may comprise adding an adhesion metallization and/or wetting metallization to an outside portion of the sintered ceramic body, where the adhesion layer may comprise titanium and the wetting layer may comprise molybdenum or niobium.

The hermetically sealing step g) may further comprise forming a gold braze between the adhesion and/or wetting metallization and the ferrule.

The conductive paste may comprise a substantially pure metal paste containing at least 90% metal by weight or by volume. The conductive paste may be a substantially pure platinum paste.

In step b) the forming may be a drilling, a punching, a machining or a waterjet cutting.

A gold braze (140) may be used in step g) for hermetically sealing the feedthrough dielectric body to the ferrule.

Between steps f) and step g) it may now include the step of removing a thin layer of material from either the first side and/or the second side by lapping, grinding, water-cutting, jetting processes or by grit-blasting.

In step d) the drying of the ceramic body and the conductive paste may be by waiting a period of time, heating at an elevated temperature and/or placing within a vacuum.

The step h) of attaching a conductive leadwire to the sintered conductive paste may be at either the first or second side. The attaching method may be selected from the group consisting of ultrasonic welding, thermal sonic bonding, laser welding, arc welding, gas welding, resistance welding, projection welding, butt welding, slash welding, upset welding, solid state welding, friction welding, fusion welding, inductive welding, percussion welding or electron beam welding.

The ferrule may be a separately manufactured component attached to the opening of the housing of the active implantable medical device or the ferrule may be formed as a part of the housing of the active implantable medical device.

The ceramic body may comprise at least 96% percent alumina by weight or by volume.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 53 is a perspective view of another embodiment of a wire bond pad with attachment fingers;

FIG. 53A is a perspective view of the embodiment of wire bond pad similar to FIG. 53;

FIG. 54 is an enlarged sectional view of another embodiment of a wire bond pad with a pin co-fired into the platinum filled via;

DETAILED DESCRIPTION OF THE PREFERRED EMBODIMENTS

Figure 1:
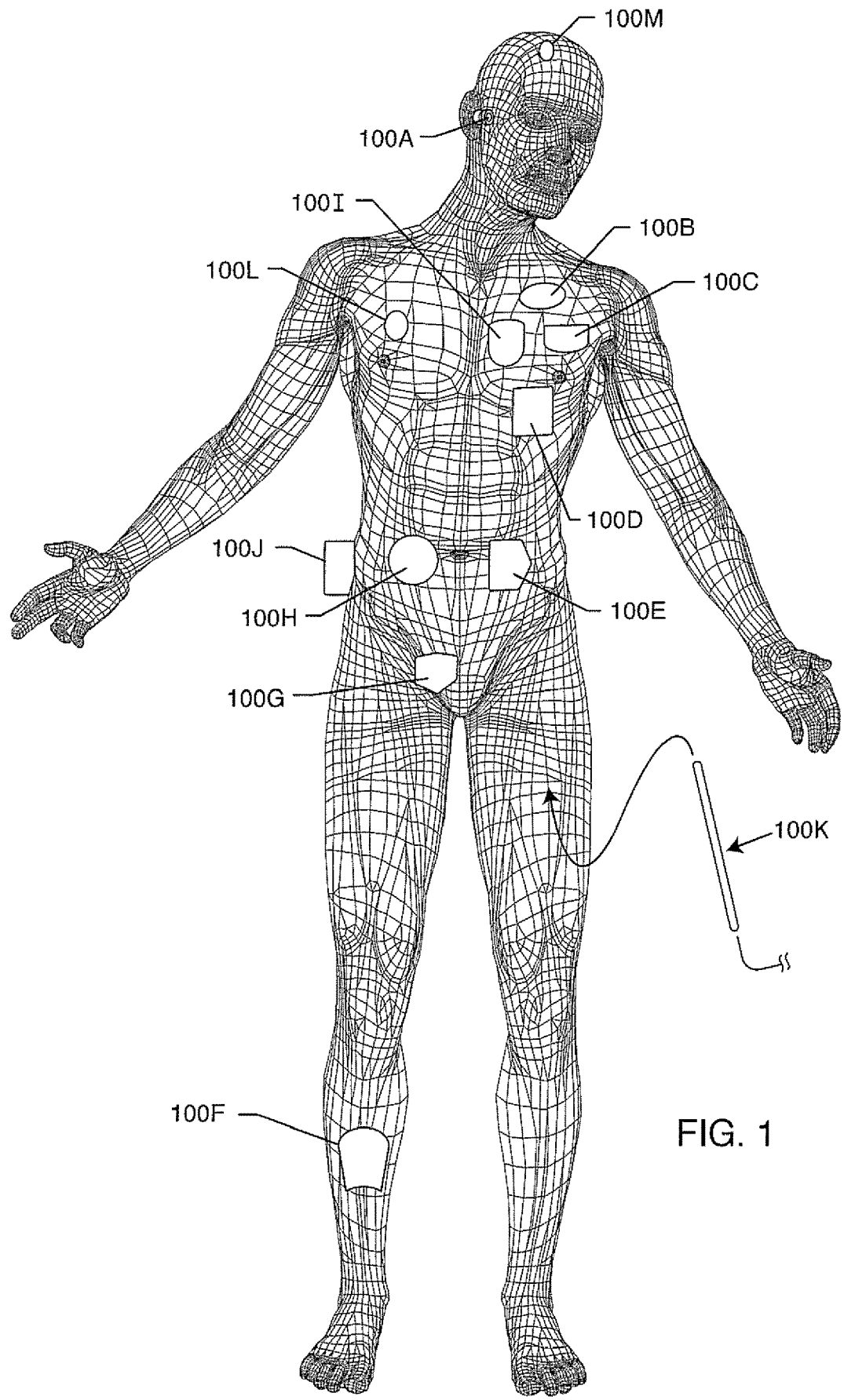
FIG. 1 is a wire-formed diagram of a generic human body showing a number of exemplary implantable medical devices.

FIG. 1 illustrates various types of active implantable and external medical devices 100 that are currently in use. FIG. 1 is a wire formed diagram of a generic human body showing a number of implanted medical devices. Medical device 100A is a family of external and implantable hearing devices which can include the group of hearing aids, cochlear implants, piezoelectric sound bridge transducers and the like. Medical device 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The lead wires that come from a deep brain stimulator are often placed using real time imaging. Most commonly such lead wires are placed during real time MRI. Medical device 100C shows a cardiac pacemaker which is well-known in the art. Medical device 100D includes the family of left ventricular assist devices (LVAD's), and artificial hearts, including the recently introduced artificial heart known as the Abiocor. Medical device 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. Medical device 100F includes a variety of external or implantable bone growth stimulators for rapid healing of fractures. Medical device 100G includes urinary incontinence devices. Medical device 100H includes the family of pain relief spinal cord stimulators and anti-tremor stimulators. Medical device 100H also includes an entire family of other types of neurostimulators used to block pain. Medical device 100I includes a family of implantable cardioverter defibrillators (ICD) devices and also includes the family of congestive heart failure devices (CHF). This is also known in the art as cardio resynchronization therapy devices, otherwise known as CRT devices. Medical device 100J illustrates an externally worn pack. This pack could be an external insulin pump, an external drug pump, an external neurostimulator, a Holter monitor with skin electrodes or even a ventricular assist device power pack. Medical device 100K illustrates the insertion of an external probe or catheter. These probes can be inserted into the femoral artery, for example, or in any other number of locations in the human body.

Figure 2:
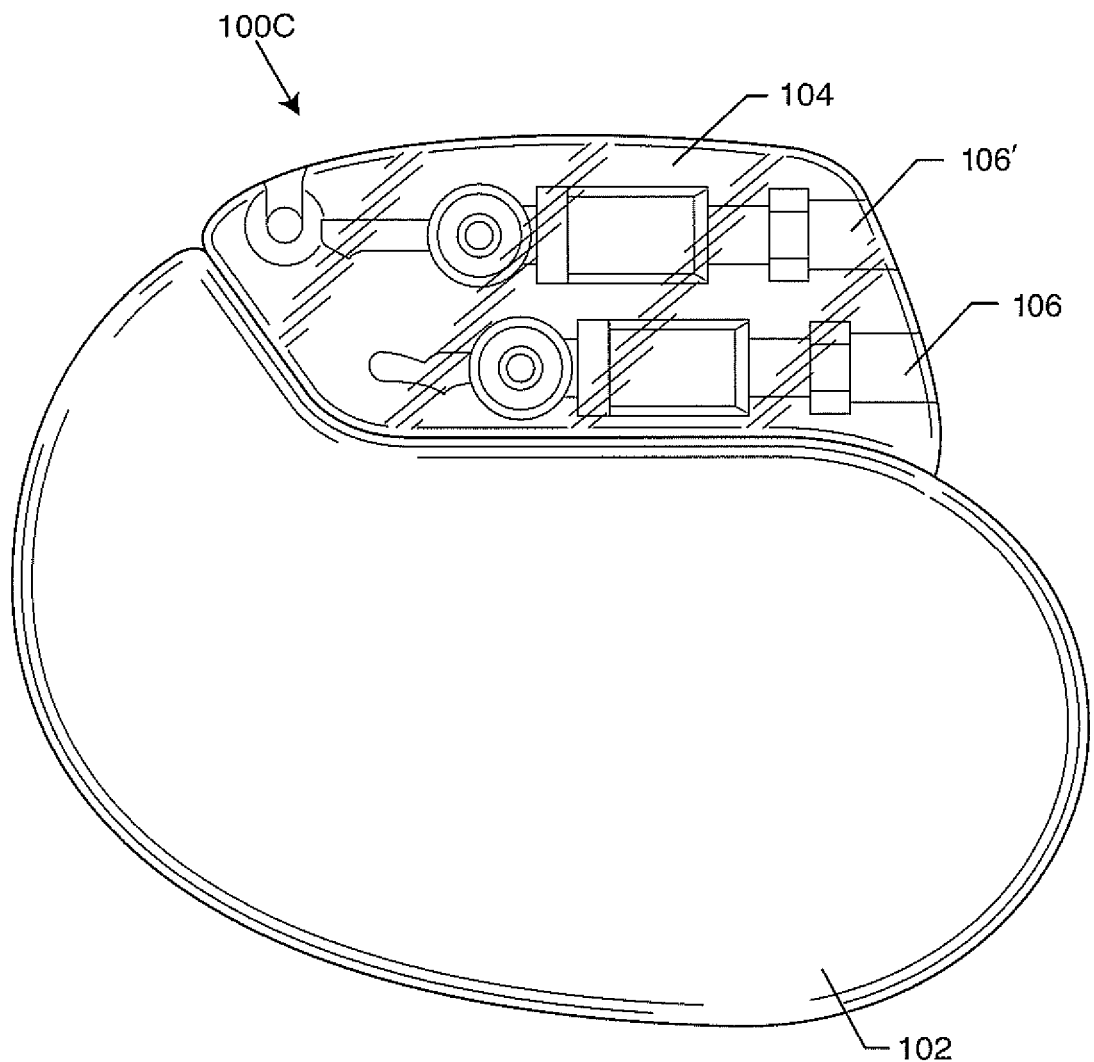
FIG. 2 is a side view of a prior art cardiac pacemaker.

FIG. 2 illustrates a prior art medical device, particularly a cardiac pacemaker 100C showing a side view. The pacemaker electronics are housed in a hermetically sealed and conductive AIMD housing 102 serving as an electromagnetic shield (typically titanium). There is a header block connector assembly 104 generally made of thermal-setting non-conductive plastic, such as Techothane. This header block connector assembly 104 houses one or more header block connector port assemblies generally in accordance with ISO Standards IS-1, IS-2, or more modern standards, such as IS4 or DF4. These header block connector port assemblies are shown as 106 and 106'. Implantable leadwires (not shown) have proximal plugs and are designed to insert into and mate with these header block connector port assemblies 106 and 106', or, in devices that do not have header block assemblies, in cavities built directly into the pulse generator itself.

As used herein, the term "lead" refers to an implantable lead containing a lead body and one or more internal lead conductors. A "lead conductor" refers to the conductor that is inside of an implanted lead body. As used herein, the term "leadwire" refers to wiring that is either inside of the active implantable medical device (AIMD) housing or inside of the AIMD header block assembly or both. As used herein, the term header block is the biocompatible material that attaches between the AIMD housing and the lead. The term header block connector assembly refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as pulse generators.

Figure 3:
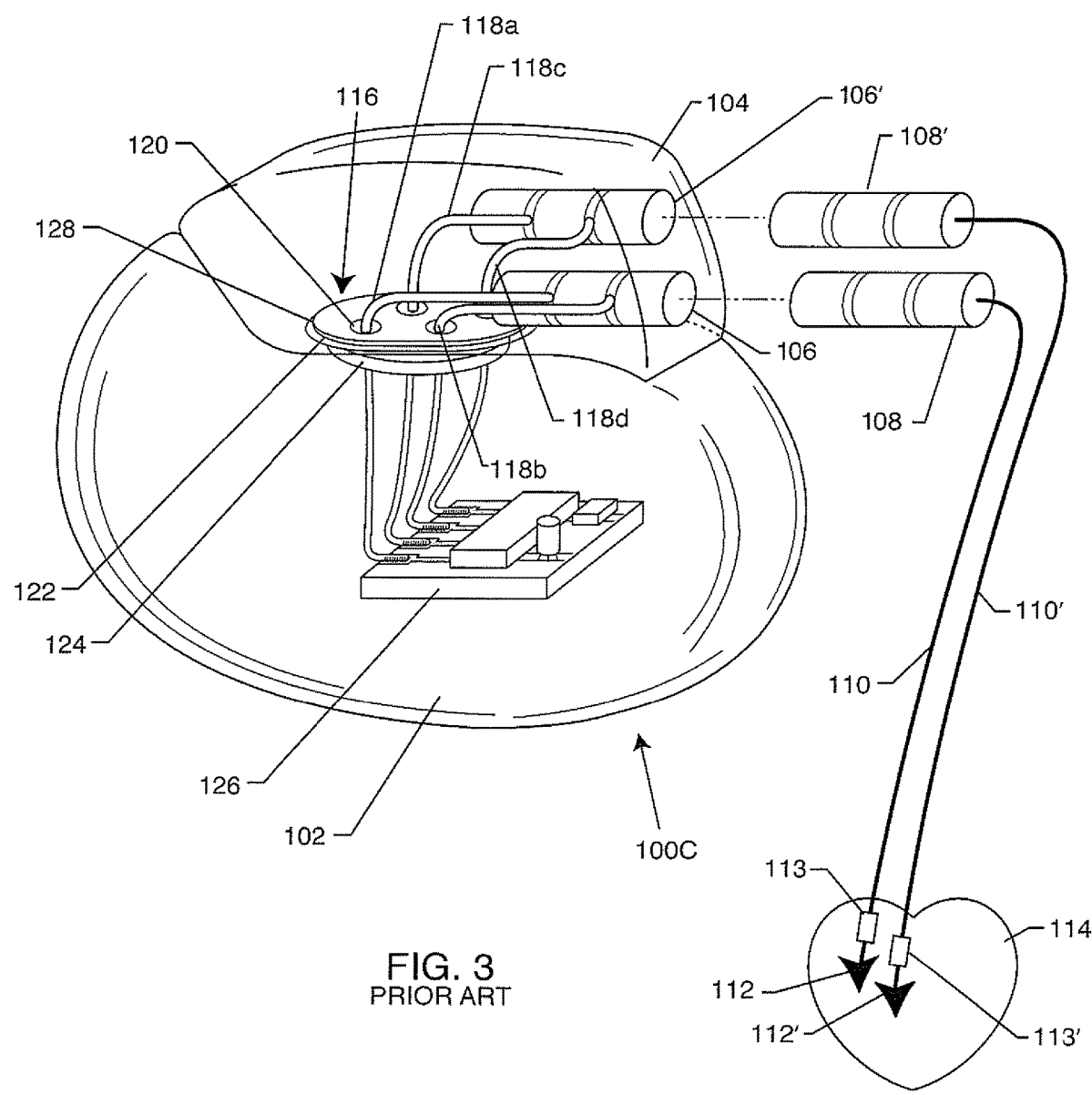
FIG. 3 is a perspective view of a prior art cardiac pacemaker.

FIG. 3 is a prior art medical device, particularly a cardiac pacemaker 100C similar to that previously illustrated in FIG. 2 except that additional interior and exterior details are illustrated. Referring to FIG. 3, one can see implantable leads 110 and 110' which may have one or more internal lead conductors (not shown). In the present case, these are bipolar leads, meaning that each implantable lead 110 and 110' has two internal lead conductors. One of these lead conductors is connected to a distal tip electrode 112 or 112'. The second lead conductor is mounted to a ring electrode 113 or 113' as illustrated. For a typical dual chamber bipolar cardiac pacemaker, one bipolar electrode will be placed into the right ventricle and the other bipolar electrode will be placed into the right atrium of the human heart 114. For example, distal tip electrode 112' could be placed in the right ventricular apex and 113' would be a bipolar electrode placed adjacent to the distal tip electrode 112'. In a similar manner, distal tip electrode 112 could be placed in the right atrial apex and ring electrode 113 would be placed adjacent to the distal electrode 112 to provide bipolar sensing in the right atrium of the heart 114. The proximal ends of the leads terminate in proximal connector plugs 108 and 108'. These proximal connector plugs are designed to be inserted into header block connector port assemblies 106 and 106' of the medical device shown as a cardiac pacemaker 100C header block connector assembly 104 or, for devices without header block assemblies (not shown), into connector cavities within the pulse generator itself. The proximal connectors are firmly held in place in the connector cavities with set screws and the like (also not shown). In this embodiment, the header block connector port assemblies 106 and 106' are in the header block connector assembly 104 and have a total of four leadwires (118a through 118d) associated with them. These leadwires are routed through a hermetic terminal subassembly 116. Each of the four leadwires is routed from the body fluid side (the header block connector assembly 104) to the inside of the cardiac pacemaker (inside the hermetically sealed AIMD housing 102) by passing through the hermetic terminal subassembly 116. Each of the leadwires 118 pass through a ferrule 122 of the hermetic terminal subassembly 116 in non-conductive relationship. The non-conductive relationship is imparted by a single insulator 120 between each of the four leadwires 118 placed in the vias of the insulator 120. It is understood by those skilled in the art that the four hermetically sealed leadwires 118 could be replaced by a single hermetically sealed leadwire comprising four individual conductors or by four separate leadwires 118 each with their own insulator and ferrule assembly. Furthermore, those skilled in the art will appreciate that a hermetic terminal subassembly may be constructed with any number of hermetically sealed leadwires in one or more large insulators having one or more vias.

The ferrule 122 of the hermetic terminal subassembly 116 is generally mechanically and hermetically attached to the AIMD housing 102 by laser welding 128 processes or the like. Attached directly on or adjacent to the hermetic terminal subassembly 116 is a feedthrough capacitor 124 which is used to decouple unwanted electromagnetic interference (EMI) signals that may couple to the implantable leads 110 and 110'. The feedthrough capacitor filter prevents such undesirable EMI signals from entering into the interior of the (pacemaker) AIMD housing 102. It is particularly adverse for high frequency EMI signals to enter into the inside of the AIMD housing 102 because once high frequency noise is inside, it can cross-couple or re-radiate to sensitive pacemaker circuits thereby disrupting proper operation of the device. For example, it has been documented in numerous technical papers that EMI can be falsely interpreted by a cardiac pacemaker as a normal heartbeat. Modern pacemakers are demand-type devices to save battery energy. That is, in the presence of a normal heartbeat, they will turn off to save battery energy. If EMI is improperly sensed as a cardiac signal, and the device turns off (inhibits) this becomes immediately life-threatening to a pacemaker dependent patient as, in this particular case, the patient's heart will not function without the pacemaker. In this particular case, the patient's heart stops beating altogether because the pacemaker has stopped providing the electrical pulses the heart needs to pump blood and sustain life. Once the leadwires 118a, 118b, 118c and 118d pass through the feedthrough capacitor, the high frequency electromagnetic noise has been largely eliminated and therefore the signals coming to the circuit board 126 will be relatively clean and be comprised primarily of low frequency biologic signals and/or pacing pulses. It is understood by those skilled in the art that circuit board 126 inside the AIMD can also be electronic circuits, electronics, circuits, flex circuits or other various electrical devices.

Figure 3A:
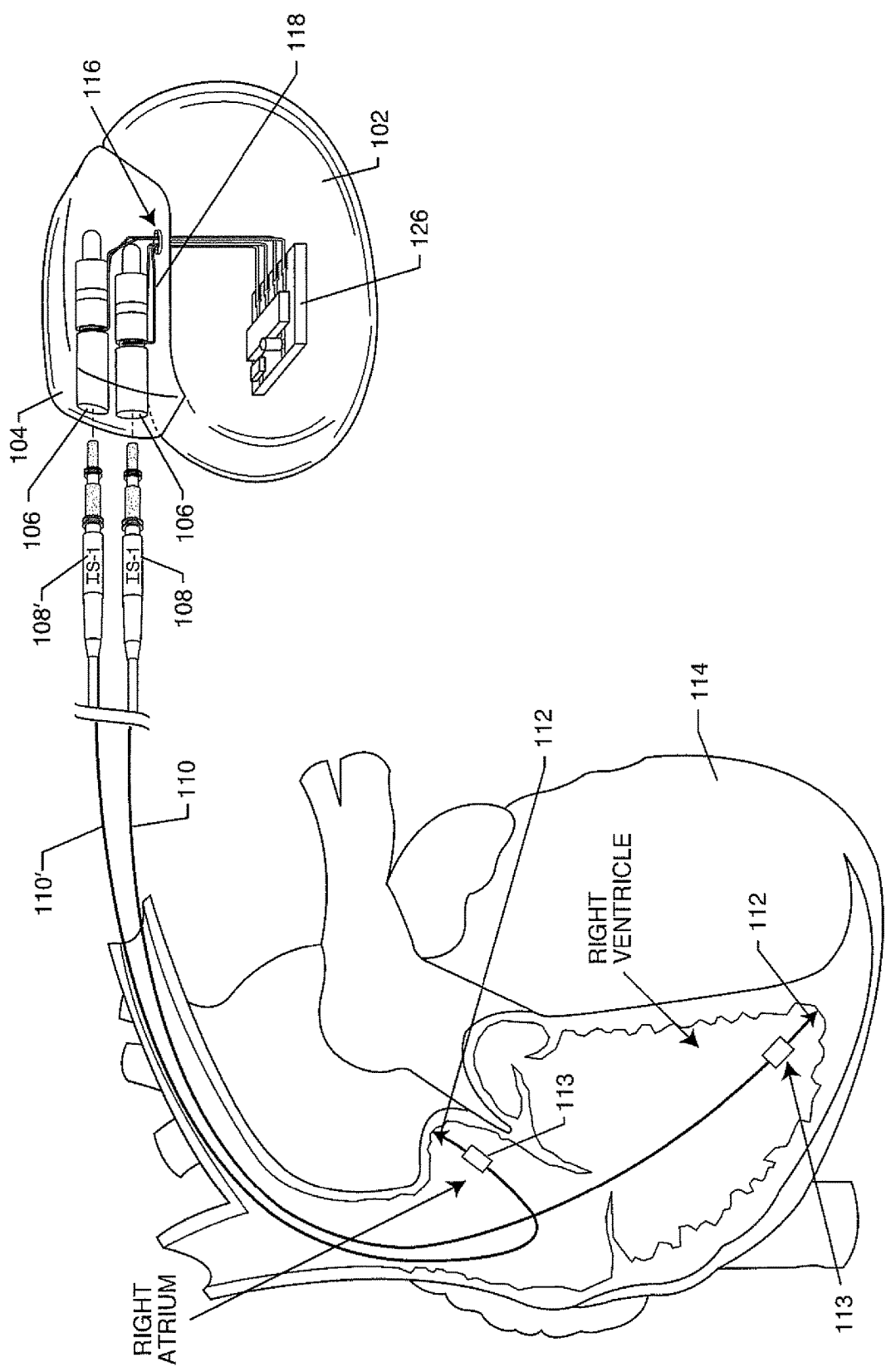
FIG. 3A is a perspective view of the prior art cardiac pacemaker of FIG. 3 now showing placements of the leads into the heart.

FIG. 3A is the same dual chamber cardiac pacemaker system previously illustrated in FIG. 3. It shows the detail of the placement of a distal tip electrode 112 into the right ventricular apex and its associated ring electrode 113. Also illustrated is the placement of a distal tip electrode 112 into the right atrial apex along with its associated ring electrode 113.

Figure 4:
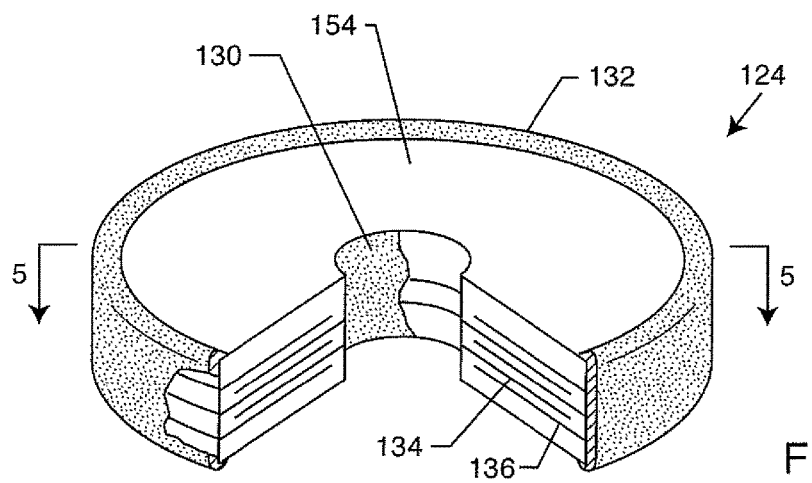
FIG. 4 is a perspective view of a prior art feedthrough capacitor.

FIG. 4 illustrates a prior art feedthrough capacitor 124 similar to the quad polar feedthrough capacitor 124 previously illustrated in FIG. 3. However, in FIG. 4, the feedthrough capacitor is unipolar for simplicity in describing its construction. In the prior art, these feedthrough capacitors are known as multilayer monolithic ceramic feedthrough capacitors. They are three-terminal devices as opposed to simple multilayer chip capacitors (MLCC), which are two-terminal devices. Two-terminal devices have considerable internal inductance and self-resonate before they reach high frequencies. For this reason, they do not make very effective broadband EMI filters. In contrast, the three-terminal devices, also known as feedthrough capacitors, are exceptional broadband devices that work from the low kilohertz frequency range through to and beyond 10 GHz. Referring once again to FIG. 4, one can see that there are alternating stacks of active electrode plates 134 interspersed with ground electrode plates 136. These are all fired in a dielectric medium 154. In general, feedthrough capacitor dielectrics are of barium titanate, strontium titanate or the like. This makes for a highly volumetrically efficient capacitor since these dielectric constants are, in general, 100 to 5000 times more efficient than an air capacitor. In order to make contact with all of the ground electrode plates 136, an external metallization 132 is applied. This can be a plated metallization, or it could be a silver or palladium silver glass frit which forms the metallization layer when fired at elevated temperature. This has the effect of placing all the ground electrode plates 136 in parallel and also provides a surface on which to make a convenient electrical connection to the ground electrode plates. There is an internal metallization 130 that is applied to the inside diameter hole of feedthrough capacitor 124. This internal metallization 130 makes contact with the active electrode plates 134.

Figure 5:
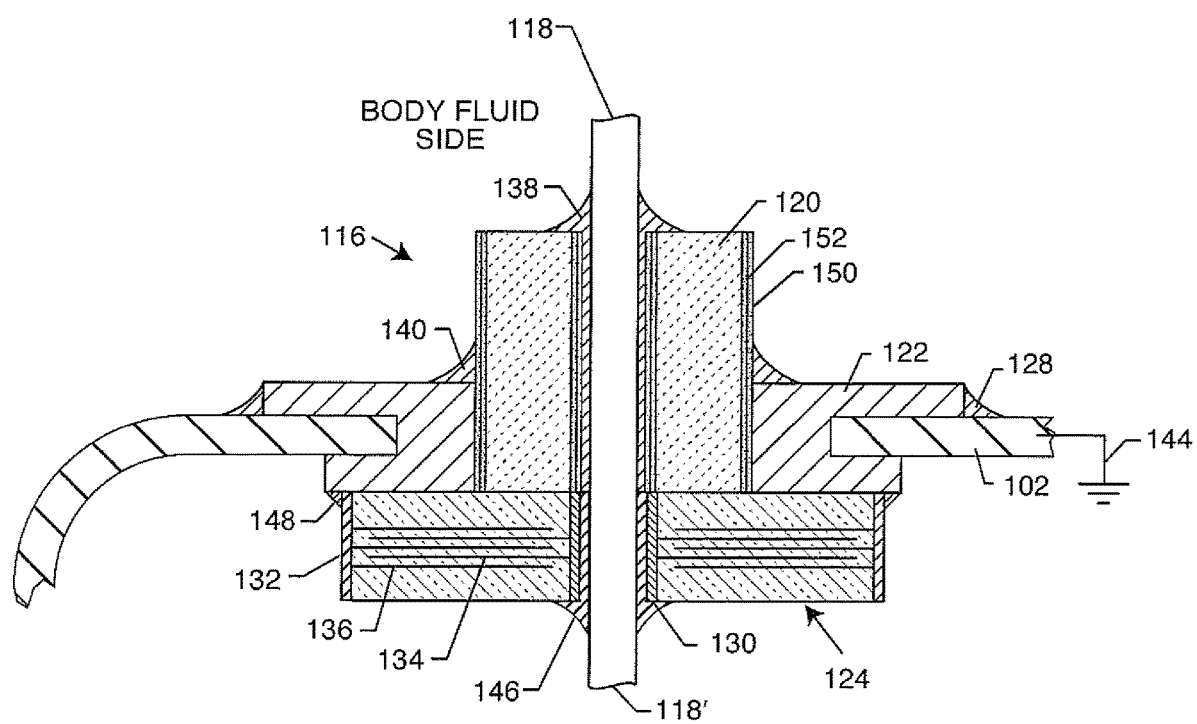
FIG. 5 is a sectional view of the prior art feedthrough capacitor of FIG. 4 mounted to a hermetic terminal subassembly.

FIG. 5 is a cross-sectional view of the unipolar capacitor of FIG. 4 shown mounted to a hermetic terminal subassembly 116 which is, in turn, installed into the metallic AIMD housing 102 of the (medical device) 100. In FIG. 5, the active electrode plates 134 and ground electrode plates 136 are visible. In this case, there is a leadwire 118 which passes all the way through an insulator 120 and also through the center hole of the feedthrough capacitor 124. The insulator 120 is shown which is typical of alumina ceramic, glass or other similar insulative material. In this example, the leadwire 118 is gold brazed 138 to the alumina ceramic insulator 120. The alumina ceramic insulator 120 is of ceramic material and requires metallization for wetting of the gold braze and ultimately hermetically sealing to the ceramic. Accordingly, it is important that surface preparations such as metallization be completed prior to the gold brazing operation. Adhesion layer 152 is a sputtered layer, typically titanium. Sputtered over this is a wetting layer 150 which would typically be of molybdenum, niobium or the like, to which a gold braze will readily wet and form a hermetic seal. Both the outside diameter and the inside diameter of the insulator 120 is thus metalized in preparation for gold brazing operation. A similar gold braze 140 is formed between the outside diameter of the insulator 120 and the ferrule 122. Sputtered layers for fabricating hermetic terminal subassemblies 116 could be metals other than the typical titanium, niobium and molybdenum examples provided herein.

The feedthrough capacitor 124 is generally bonded at or adjacent to the hermetic terminal subassembly 116. The reason for this is it is very important to intercept and decouple electromagnetic signals before they can enter into the interior space of the AIMD housing. EMI engineers call this the "genie in the bottle" effect. In other words, once the genie (i.e., EMI) is inside the AIMD housing 102, it can wreak havoc with electronic circuit functions by cross-coupling and re-radiating all over and anywhere within the bottle (i.e., the pulse generator). Consequently, it is very important that the feedthrough capacitor filter element be disposed at the point of leadwire ingress/egress where it can attenuate and/or filter high frequency electromagnetic noise before it becomes detrimental to the intended therapy delivery of the AIMD, and potentially life threatening to the patient. Accordingly, the feedthrough capacitor 124 has an electrical connection material 146 connecting the internal metallization 130 to the terminal pin or leadwire 118. There is a similar electrical connection material 148 connecting the external metallization 132 to the ferrule 122 of the hermetic seal housing. In this particular connection, an added performance reliability benefit is realized. In general, having an electrical connection material 148 connecting directly to a titanium surface is contraindicated. This is because titanium forms oxides which tend to be resistive, particularly at high frequency. By way of the present invention, connection is always made to a non-oxidized surface, such as to a gold bond pad or gold braze 140. In the case of the latter, one is referred to U.S. Pat. No. 6,765,779, which illustrates such gold bond pad connections, the contents of which are herein incorporated by reference. The ferrule 122 of the hermetic terminal subassembly is generally laser welded 128 to the titanium AIMD housing 102. The AIMD housing 102 forms a complete and hermetically sealed chamber, but also forms an overall electromagnetic shield. This is also known as an equipotential surface or ground. The ground 144 illustrated in FIG. 5 represents that this is indeed a shielded equipotential surface.

Figure 6:
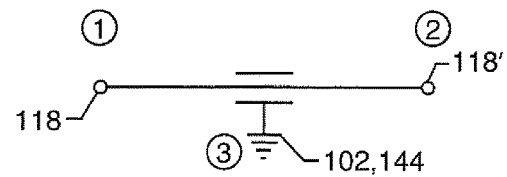
FIG. 6 is an electrical schematic diagram of the capacitor of FIG. 5.

FIG. 6 is a schematic diagram taken from FIG. 5 illustrating the unipolar feedthrough capacitor 124. This is known in the industry as a three-terminal device. It has an end of the terminal pin or leadwire 118 disposed toward body fluids and then the leadwire passes through the feedthrough capacitor electrode plates to an internal end of the terminal pin or internal leadwire 118' inside the AIMD. The capacitor ground electrode plates are electrically grounded to the AIMD housing 102 with ground 144. This yields three distinct terminal locations, namely the leadwire 118, the internal leadwire 118' and the ground 144. Substantial signal attenuation occurs at high frequency from the terminal one end of the leadwire 118 to the terminal two end of the internal leadwire 118'. In this way, terminal end one of leadwire 118 and terminal end two of internal leadwire 118' along with the ground 144 form a feedthrough capacitor known in the art as a three-terminal device.

Figure 7:
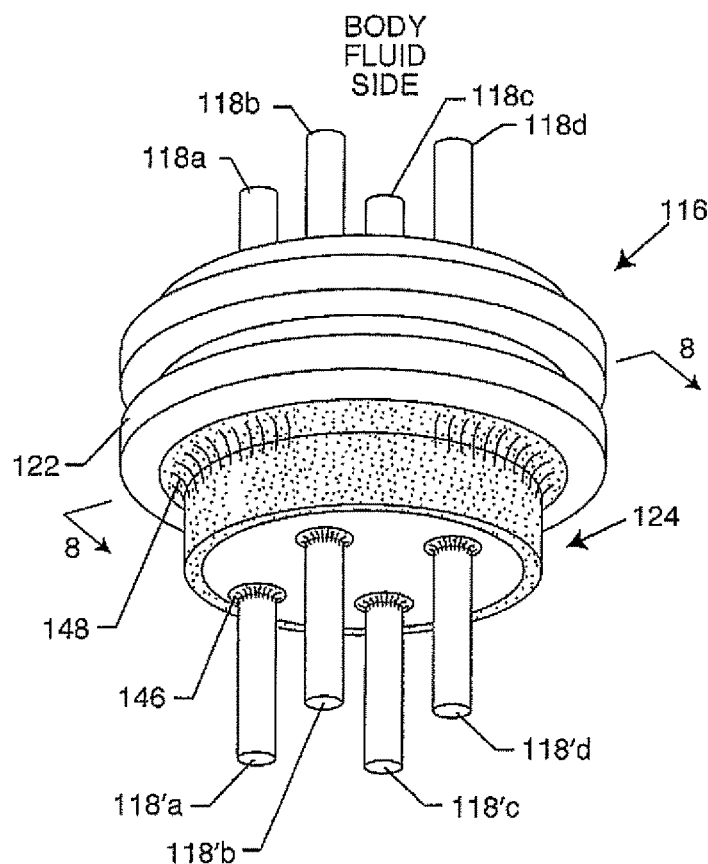
FIG. 7 is a perspective view of the quad polar feedthrough capacitor and hermetic terminal assembly of FIG. 3.

FIG. 7 illustrates the quad polar feedthrough capacitor and hermetic terminal subassembly 116 previously illustrated in FIG. 3. It is very similar to the unipolar capacitor illustrated in FIGS. 4, 5 and 6 except in this case it has four leadwires 118a-118d and four feedthrough holes (quad polar). It has a ferrule 122 generally of titanium which is ready for laser welding into the AIMD housing 102 (not shown).

Figure 8:
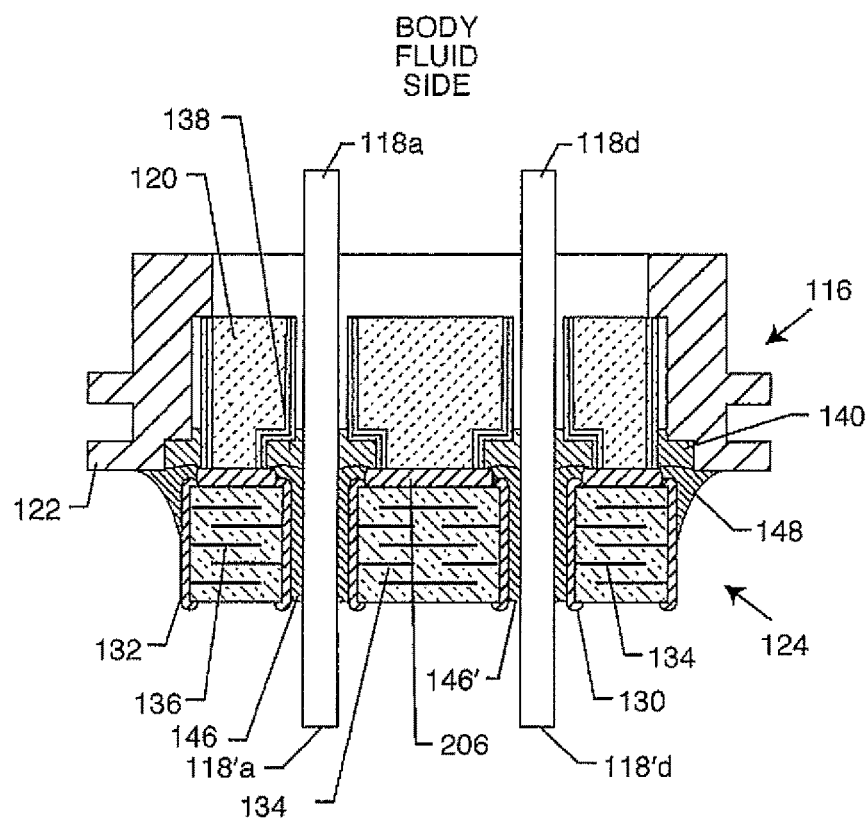
FIG. 8 is a sectional view of the feedthrough and hermetic terminal assembly of FIG. 7.

FIG. 8 is a prior art sectional view taken generally from section 8-8 from FIG. 7. This illustrates the hermetic terminal subassembly leadwires 118a-d passing through the insulator 120 in non-conductive relationship and also through the feedthrough capacitor 124 wherein the active electrode plates 134 are electrically connected to the hermetic terminal subassembly leadwire 118 using electrical connection material 146 and wherein the feedthrough capacitor ground electrode plates 136 are electrically connected to the ferrule 122 and gold braze 140 using an electrical connection material 148. Referring once again to FIGS. 3, 5, 7 and 8, in each case it is seen that the hermetic terminal subassembly leadwires 118a-d pass all the way through the entire structure, namely, the hermetic terminal subassembly 116 and the feedthrough capacitor 124. In general, these hermetic terminal subassembly leadwires 118a-d are continuous and pass through from the body fluid side to the inside of the medical device 100 AIMD housing 102. Because the hermetic terminal subassembly leadwires 118a-d pass through from the body fluid side to the inside of the device by way of header block connector assembly or the like, it is very important that these hermetic terminal subassembly leadwire 118 materials be both biocompatible and non-toxic. Generally, in the prior art, these hermetic terminal subassembly leadwires are constructed of platinum or platinum-iridium, palladium or palladium-iridium, niobium or the like. Platinum-iridium is an ideal choice because it is biocompatible, non-toxic and is also mechanically very strong. The iridium is added to enhance material stiffness and to enable the hermetic terminal subassembly leadwire to sustain bending stresses.

An issue with the use of platinum for hermetic terminal subassembly leadwires 118a-d is that platinum has become extremely expensive and may be subject to premature fracture under rigorous processing such as ultrasonic cleaning or application use/misuse, possibly unintentional damaging forces resulting from Twiddler's Syndrome. Accordingly, what is needed is a filtered structure like a feedthrough 116 and a feedthrough capacitor 124 assembly which eliminates these high-priced, platinum, platinum-iridium or equivalent noble metal hermetic terminal subassembly leadwires 118. For additional examples of hermetic terminal subassemblies with feedthrough capacitors that employ leadwires 118, one is referred to U.S. Pat. Nos. 5,333,095, 5,896,267, 5,751,539, 5,905,627, 5,959,829, 5,973,906, 6,008,980, 6,159,560, 6,275,379, 6,456,481, 6,529,103, 6,566,978, 6,567,259, 6,643,903, 6,765,779, 6,765,780, 6,888,715, 6,985,347, 6,987,660, 6,999,818, 7,012,192, 7,035,076, 7,038,900, 7,113,387, 7,136,273, 7,199,995. 7,310,216, 7,327,553, 7,489,495, 7,535,693, 7,551,963, 7,623,335, 7,797,048, 7,957,806, 8,095,224, 8,179,658 the contents of all of which are incorporated herein by reference.

As discussed earlier, for ceramic based hermetic terminals or feedthroughs, the most critical feature in its design is the metal/ceramic interface. Also, as indicated above, one method for limiting residual stress is to select combinations of materials whose thermal contractions after bonding are matched. Alternatively, materials with different CTEs can be coupled through braze materials whose high creep rate and low yield strength reduce the stresses generated by the differential contraction. Given the challenge associated with CTE matching, it is the intent of the present invention to deliberately generate hermetic structures with residual stress levels such that either matched hermetic structures or structures that have protectively compressive stresses from the ceramic part to the filled via material at the bonding interface are created, thereby creating a hermetic seal. As given above, usually this is accomplished by selecting components with different CTEs, however, the intent of the present invention is to deliberately create the desired level of residual stresses by judiciously selecting the ceramic and via fill materials and prescribing a firing process that results in the ceramic material shrinking more than that of the via fill material. Additionally, the intent of the present invention is to deliberately create a mutually conformal interface (tortuous, intimate knitline) between the ceramic and the via fill materials. Further, the intent of the present invention is to also deliberately create an interface bond between the ceramic and the via fill material that is tolerant of stress and of CTE mismatch between the ceramic and the via fill materials and is not susceptible to erosion by body fluids so as to achieve sustainable hermeticity over service life. The term "knitline" is defined herein as the interfacial boundary between the alumina and the platinum. The knitline may form a meandering or undulating path that provides sufficient tortuosity such that it inhibits crack initiation, and more importantly, crack propagation, and additionally, because of the intimacy of the knitline, impairs leakage of fluids. As used herein, the word tortuous or tortuosity refers to the roughened, complex, or undulating knitline that is formed at the interfacial boundary between the alumina and the platinum. This tortuous interface is characterized by hills and valleys which is topographically three dimensional and forms a very strong and reliable hermetic bond.

In part, the critical aspect of the metal/ceramic interface is related to the intimacy and tortuosity of the knitline formed when the metal surface mates with the ceramic surface (i.e., post sintering, the metal surface should mirror the image of the ceramic surface and intimately, or tightly, mate with each other), the type of bond between the ceramic and the metal (certain glass phased interfaces are contraindicated due to their susceptibility to erosion by body fluids, and hence, subsequent separation and loss of hermeticity at these interfaces), and the sensitivity of the bond strength to a tensile stress field (residual stresses in the final structure should be sufficiently less than the possible failure stresses of the structure). Any broken symmetry, aberrant dimensionality due to poor process control, unfavorable design aspect ratios, design aspects wherein intolerable stress concentrations or fields develop, atomic relaxation is inhibited and intermixing of atoms at their boundaries that can substantially negatively modify the deformational tolerance of the final structure must be considered when creating interfaces between ceramic oxides and conductive metal vias within those ceramic oxides to preserve intentional immediate and sustainable functional behavior such as hermeticity.

There are a number of patents that disclose alternatives for platinum leadwires 118 in hermetic terminal subassemblies. Among these are a few that discuss hermetic terminals manufactured by a co-fire process and based on an alumina ceramic with platinum paste filled vias. Some of the more prominent concepts are disclosed in U.S. Pat. No. 5,782,891 to Hassler et al., U.S. Pat. No. 6,146,743 to Haq et al., U.S. Pat. No. 6,414,835 to Wolf et al., U.S. Pat. No. 8,000,804 to Wessendorf et al., U.S. Pat. No. 8,043,454 to Jiang et al., and US Published Applications 2007/0236861 to Burdon et al., 2007/00609969 to Burdon at al., 2011/0102967 to Munns et al., and 2011/0248184 to Shah. None of the prior art concepts, however, including the prominent concepts noted above, teaches a structure that has a mutually conformal interface, also called a tortuous, intimate knitline, that results in sustainable hermeticity for an AIMD. Further, none of the prior art, including the prominent concepts noted above, teach a structure, or the manufacture of such a structure, having residual stress levels such that either matched hermetic structures or structures that have protectively compressive stresses from the ceramic part to the filled via at the bonding interface are created.

Briefly discussing each of the prominent concepts provided above, U.S. Pat. No. 5,782,891 to Hassler et al. is directed to an implantable ceramic enclosure which has a hermetically sealed substrate through which vias pass. While Hassler teaches a ceramic substrate feedthrough that is co-fired with metallic conductive interconnects, these interconnects are either staggered or are straight with a broad conductor (see Hassler FIG. 8). It is the staggering of the vias alone or in conjunction with a broad conductor that imparts hermeticity of the vias in this structure, and not a mutually conformal interface or tortuous, intimate knitline for a single straight via. Additionally, Hassler teaches selection of materials to avoid shrinkage mismatch and not structures wherein shrinkage of the ceramic is greater than shrinkage of the filled via material. Further Hassler does not teach a terminal or feedthrough having residual stress levels such that matched hermetic structures or structures that have protectively compressive stresses from the ceramic part to the filled via material at the bonding interface are created.

Figure 11:
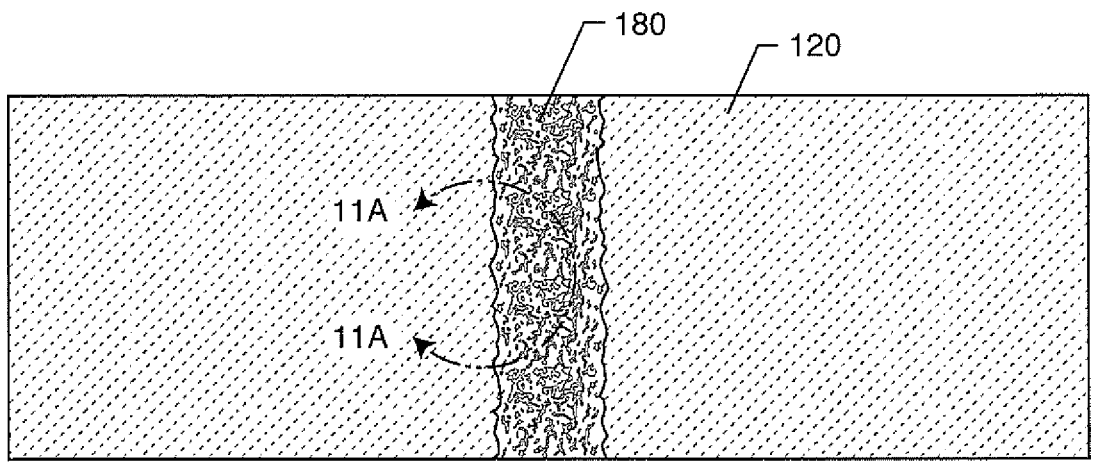
FIG. 11 is a sectional view of a prior art hermetic insulator with a metallic paste filled via.
Figure 11A:
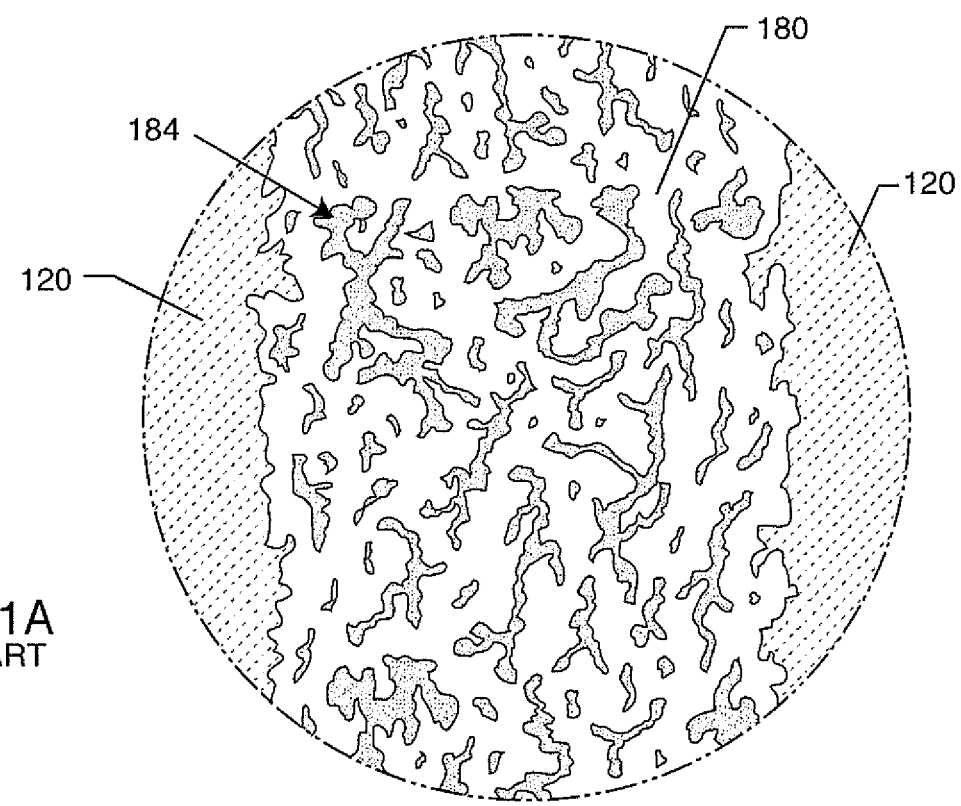
FIG. 11A is an enlarged view of the structure of FIG. 11 now showing irregular glass filled structures.

U.S. Pat. No. 6,146,743 to Haq et al. teaches hermetically sealed multilayer substrates with vias. One is directed to Haq FIG. 16, which has been reproduced herein as FIG. 11. FIG. 11 shows the cross section of via fill after sintering. Haq discloses that the in this structure the "ceramic powder component also improves the degree of adhesion between the ceramic forming the substrate itself and external via 66, thereby ensuring the formation of a hermetic seal in ceramic substrate 50. This hermetic seal inhibits or prevents internal metallization layers 64 from becoming oxidized when substrate 50 is air-fired during one method of the present invention." FIG. 11A is taken from section 11A-11A from FIG. 11 and shows a blow-up of the internal micro-structure of the Haq post-sintered via hole 180. One is directed to Haq column 21, lines 32-43. Towards the end of that paragraph it states, "As the unfired green tape material emerges from the casting tape machine, it is coated with a castable dielectric composition that upon firing at high temperatures forms a glass." It is the external via that imparts hermeticity of the internal vias in this structure, and not a mutually conformal interface or tortuous, intimate knitline for a single straight via. Regarding shrinkage, Haq teaches matching shrinkages between ceramic and filled via material. Haq does not teach a structure wherein shrinkage of the ceramic is greater than shrinkage of the filled via material. Further Haq does not teach a terminal or feedthrough having residual stress levels such that matched hermetic structures or structures that have protectively compressive stresses from the ceramic part to the filled via material at the bonding interface are created.

U.S. Pat. No. 6,414,835 to Wolf et al. discloses "hermetically sealing the common substrate edge to the ferrule inner wall within the centrally disposed ferrule opening and electrically coupling the plurality of substrate ground paths to the ferrule", and claims a "plurality of substrate conductive paths extending through the co-fired metal-ceramic substrate between the internally and externally facing layer surfaces and electrically isolated from one another further comprise a plurality of electrically conductive vias extending through via holes of the plurality of layer thicknesses and a plurality of electrically conductive traces formed on certain of the internally or externally facing layer surfaces such that the conductive traces join the conductive vias to form each substrate conductive path." FIG. 5 of Wolf et al. illustrates this as staggered vias. Further the vias in FIG. 5 of Wolf are subsequently covered with biocompatible end caps 70 and biocompatible gold brazes 80 on the body fluid side. It is the staggering of the vias in conjunction with the end caps that imparts hermeticity of the vias in this structure, and not a mutually conformal interface or tortuous, intimate knitline for a single straight via. Wolf teaches trimming laminated ceramic layers to account for shrinkage and also compression of the co-fired substrate by the ferrule. Wolf, however, does not teach structures wherein shrinkage of the ceramic is greater than shrinkage of the filled via material. Further Wolf does not teach a terminal or feedthrough having residual stress levels such that matched hermetic structures or structures that have protectively compressive stresses from the ceramic part to the filled via material at the bonding interface are created.

U.S. Pat. No. 8,000,804 to Wessendorf et al. illustrates an electrode array for a neurostimulator. The Wessendorf patent teaches "a plurality of electrodes arranged in a two-dimensional array and extending through the ceramic base between the first and second major surfaces; a ceramic lid having a plurality of electrical connections extending therethrough, with the ceramic lid being attachable to the ceramic base to form a hermetically-sealed interior region; and an electronic circuit (e.g. a demultiplexer circuit) located within the hermetically-sealed interior region." Hermeticity in this case is imparted by "a two-part ceramic package which can be hermetically sealed" and not by a mutually conformal interface or tortuous, intimate knitline for each single straight via. Wessendorf teaches matching CTEs for ceramic and via fill materials, however, Wessendorf does not teach structures wherein shrinkage of the ceramic is greater than shrinkage of the filled via material. Further Wessendorf does not teach a terminal or feedthrough having residual stress levels such that matched hermetic structures or structures that have protectively compressive stresses from the ceramic part to the filled via material at the bonding interface are created.

U.S. Pat. No. 8,043,454 to Jiang et al. describes a method of making a hermetic via in a ceramic substrate that is composed of a noble metal powder in a glass-free paste that contains alumina and a mixture of niobium pentoxide. The addition of the niobium pentoxide to the pre-sintered paste prevents shrinkage of the paste during thermal processing and binds to both the ceramic and the noble metal particulates in the via, thus maintaining a hermetic seal around the via. Hence, hermeticity in this case is imparted by niobium pentoxide and not a mutually conformal interface or tortuous, intimate knitline for a single straight via. Jiang teaches avoiding GTE mismatches for feedthroughs and compression seals formed by metal tubing on ceramic insulators, however, Jiang does not teach structures wherein shrinkage of the ceramic is greater than shrinkage of the filled via material. Further Jiang does not teach a terminal or feedthrough having residual stress levels such that matched hermetic structures or structures that have protectively compressive stresses from the ceramic part to the filled via material at the bonding interface are created.

U.S. Patent Pub. Nos. 2007/0236861 and 2007/0060969, both to Burdon et al., disclose hermetic interconnects for implantable medical devices. One embodiment includes a conductive material introduced to a via in a single layer. Also disclosed are alumina ceramic with vias in which the conductive material may be platinum. Both publications discuss terminal assemblies comprising staggered vias only. Hermeticity in these structures is imparted by the staggered vias and not by a mutually conformal interface or tortuous, intimate knitline for a single straight via. Neither application teaches structures wherein shrinkage of the ceramic is greater than shrinkage of the filled via material. Further neither application discusses or teaches a terminal or feedthrough having residual stress levels such that matched hermetic structures or structures that have protectively compressive stresses from the ceramic part to the filled via material at the bonding interface are created.

U.S. Pub. No. 2011/0102967 to Munn et al. discloses a multilayered feedthrough for an implantable medical device that includes a substrate having a first edge, a second edge, and a substrate length. A plurality of traces is formed on the substrate and extends along the substrate length. The plurality of traces extends to the first and second edges of the substrate. An insulator layer is formed on the substrate and the plurality of traces. A ground plane layer is formed on the insulator layer. Munn FIG. 7 shows the individual vias of this structured captive within these substrates which in turn imparts hermeticity to this structure and not by a mutually conformal interface or tortuous, intimate knitline for a single straight via. Munn does not discuss or teach structures wherein shrinkage of the ceramic is greater than shrinkage of the filled via material. Further Munn does not discuss or teach a terminal or feedthrough having residual stress levels such that matched hermetic structures or structures that have protectively compressive stresses from the ceramic part to the filled via material at the bonding interface are created.

U.S. Pub. No. 2011/0248184 to Shah reveals a sensor substrate with via holes. At least one of the via holes is hermetically sealed with an optically transmissive material and not by a mutually conformal interface or tortuous, intimate knitline for a single straight via. Shah does not discuss or teach structures wherein shrinkage of the ceramic is greater than shrinkage of the filled via material. Further Shah does not discuss or teach a terminal or feedthrough having residual stress levels such that matched hermetic structures or structures that have protectively compressive stresses from the ceramic part to the filled via material at the bonding interface are created.

In summary, none of the prior art concepts teach a structure that has a mutually conformal interface or tortuous, intimate knitline that results in sustainable hermeticity for an AIMD, has higher shrinkage of the ceramic than of via fill material, or possesses residual stress levels such that matched hermetic structures or structures that have protectively compressive stresses from the ceramic part to the filled via material at the bonding interface are created.

It is understood that "vias" are defined as holes, apertures, conduits, or voids created in either insulators or capacitors. A via can also be filled with a conductive material or bore-coated with a conductive material such that the inside surface is metalized and conductively coated. A via in a capacitor will generally be referred to as a capacitor via. A via in an insulator will generally be referred to as an insulator via. Accordingly, the terms filled or bore-coated can also be applied to either capacitor vias or insulator vias.

Figure 9:
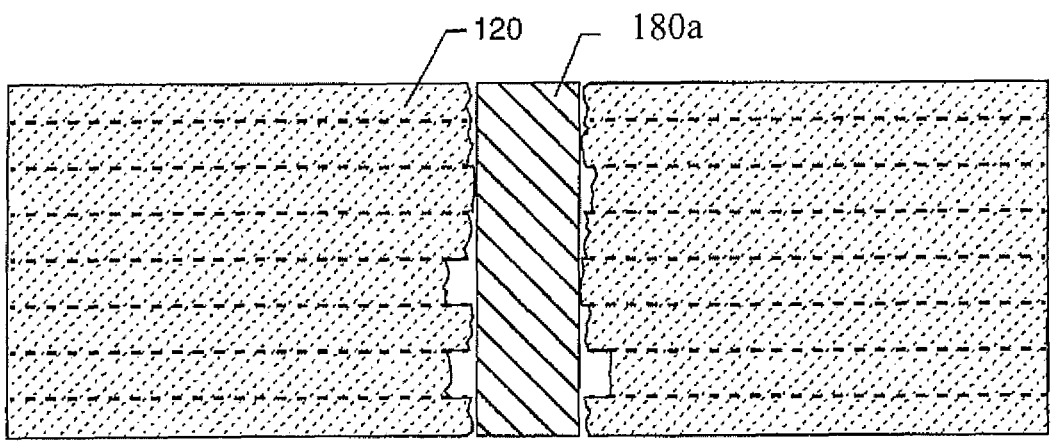
FIG. 9 is a sectional view of a prior art hermetic insulator with a solid metallic filled via in a green state.
Figure 10:
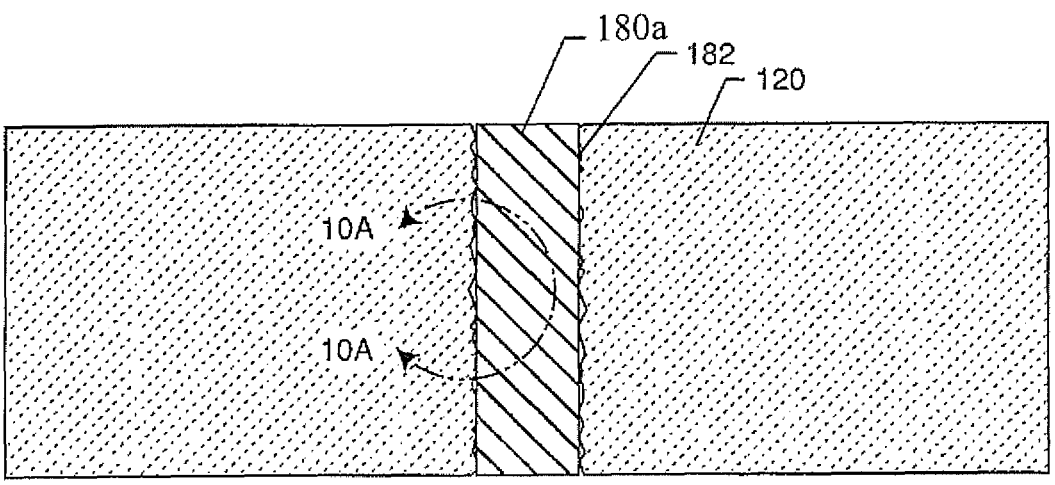
FIG. 10 is a sectional view of the structure of FIG. 9 now after sintering.
Figure 10A:
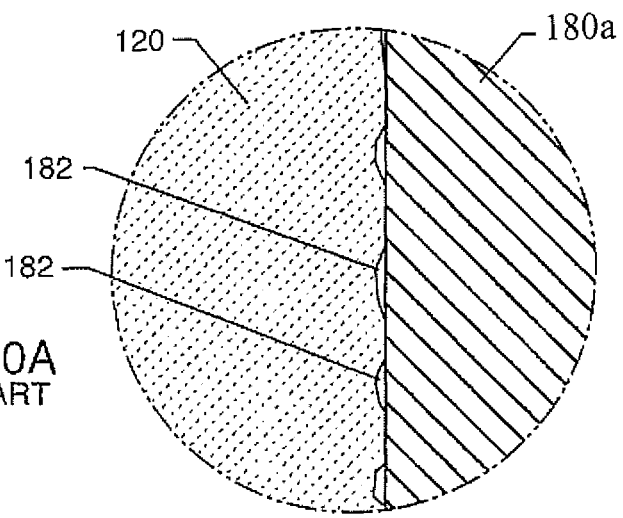
FIG. 10A is an enlarged view taken from FIG. 10 along lines 10A-10A now showing gaps between the solid metallic leadwire and the insulator.

FIG. 9 illustrates a prior art cross-section of a different type of insulator 120 via fill. The insulator 120 is a ceramic substrate formed by roll compaction. After compaction, the leadwire 180A is placed within the insulator via. In this case, the insulator via is filled with a solid platinum leadwire 180A. One is referred to U.S. Pat. Nos. 7,480,988; 7,989,080; and 8,163,397. These three patents share a common priority chain and are directed to a method and apparatus for providing a hermetic electrical feedthrough. All three of these patents were assigned to Second Sight Medical Products, Inc. and will hereinafter be referred to as the "Second Sight" patents. FIG. 3 of the Second Sight patents is a flow process that starts with drilling blind holes in a green ceramic sheet. Then lengths of platinum leadwire 180A are cut and inserted into the sheet holes in step 39. The ceramic wire assembly is then fired at 1600° C. in step 44. Second Sight discloses that "during the firing and subsequent cooling, the ceramic expands shrinking the holes around the wires 38 to form a compression seal. The shrinkage is believed to occur, at least in part, as a consequence of polymer binder burnout. The fine aluminum oxide suspension permits uniform and continuous sealing around the surface of the wire. Additionally, at the maximum firing temperature, e.g., 1600° C., the solid platinum wires being squeezed by the ceramic exhibit sufficient plasticity to enable the platinum to flow and fill any crevices. This action produces a hermetic metal/ceramic interface." Further, Second Sight discusses that "After lapping, the feedthrough assembly comprised of the finished ceramic sheet and feedthrough wires, is subjected to a hermeticity test, e.g., frequently a helium leak test as represented by block 56 in FIG. 3." While Second Sight discusses forming a compression seal and platinum flow to fill any crevices, creation of mutually conformal interface or tortuous, intimate knitline between the alumina and the platinum wire is not taught.

In addition, latent hermetic failures in device feedthrough terminals have been known to occur due to susceptibility of the glass phased interface between these mating materials to erosion by body fluids. This outcome is particularly prevalent for interfaces comprising silicate glasses that are often a result of the additives to ceramic slurries forming the tapes and via fill materials that are used to build multilayer ceramic feedthrough structures. Dissolution of silicate glasses is composition dependent. In particular, erosion of silicate glasses in the body typically occurs when the silica content is lower than about 60%. Silica glasses, as suggested by the name, are based on a tetrahedral network of atoms comprising silicon and oxygen covalently bonded to each other. Heat treatment during the assembly process of the feedthrough structure provides the means by which other elements, such as alkali and/or alkaline ions, can be introduced into the silica atomic network. When the glass composition formed at the interface is more than 60% silica, the atomic network within the glass structure typically becomes resistant to reaction with body fluids due to the dense nature of the atomic network structure. However, when the glass composition formed at the interface is less than about 60%, the glass structure is more susceptible to atomic structural degradation.

Degradation is generally due to the disruption of the silica atomic network within the glass structure by other elements, such as alkali and/or alkaline ions, introduced during binder bake out and sintering. These other elements are typically introduced into the feedthrough structure from additives used within the green alumina tape or the via fill materials, such as the platinum paste, or both. For example, if the additives in either material make available alkali-metal atoms for exchange with silicon atoms within the silica atomic network, and if the result is an interface having a silica weight percent below about 60%, then rapid ion exchange of the alkali-metal cations with hydrogen ions from body fluid typically occurs. This results in the formation of functional hydroxyl, or —OH, groups that are highly reactive in the body, breaking down and weakening the atomic network structure of the glass phased interface thus increasing the likelihood of a breach in the hermeticity of the feedthrough terminal. Hence, hermetic structures created by mating alumina and platinum are not obvious and any inherency in the bond developed between these two materials does not necessarily result in a biocompatible final structure that can sustain hermeticity over the service life of an AIMD.

Once again referring to U.S. Pat. No. 8,043,454 to Jiang et al., in sharp contrast to the present invention, Jiang adds between 1-10 percent by weight of niobium pentoxide. Another way to look at this is in the present invention, organic binders and solvents are used as opposed to inorganic additives. Referring once again to FIG. 11A, additives to the platinum-filled via hole 180 such as disclosed by Haq may result in unfavorable functionality. For example, the elongate channel-like structures 184 that are actually a result of additives like ceramic powder can lower electrical conductivity if the conductivities of these phases are significantly different from the primary densified material formed. This is discussed in some of the prior art cited. It is very important for human implant applications that the resistivity of the filled via holes be as low as possible. The inventors have found that adding any ceramic powder to the platinum paste substantially increases the electrical resistivity of the post sintered via hole. This is a major reason why the inventors have been working over a number of years to develop a pure platinum sintered via hole. This is particularly important for AIMDs, such as implantable cardioverter defibrillators. An implantable cardioverter defibrillator not only senses electrical activity, but it must be able to deliver a very high voltage and high current shock in order to defibrillate the patient. This means that the entire system, including the lead conductors, the hermetic terminal subassembly via holes, and associated internal circuitry must have very low resistance and low impedance so that a high current can be effectively delivered. Furthermore, and as noted above, the creation of a glassy-phased channel-like structure 184 bonded has the potential problem of latent hermetic leaks when exposed to body fluid. The present invention resolves this issue.

In the present invention, a post sintered essentially high purity alumina substrate 188 with one or more via holes 180 that pass from an outside surface of the alumina substrate 188 to an inside surface of the alumina substrate 188 is provided wherein, the platinum conductors 186 comprise a non-toxic and biocompatible post sintered essentially pure platinum fill. There are several differences between the present invention and the prior art in addition to those specifically discussed in the brief overview of specific art cited. In the prior art, typically various additives are used to modify the alumina ceramic and/or the platinum paste. In the prior art, at times, it is not even a pure platinum paste that is used (see Wessendorf column 5, line 29), but rather one containing other refractory type materials, such as tungsten or the like. These additives are used to match the CTE during fabrication. In other words, these prior art systems go to a lot of effort to match the ceramic and metal parts of the system so that cracking or loss of hermeticity between the alumina substrate 188 and platinum conductor 186 in the via hole 180 does not occur over time. Additionally, much of the prior art processes lay down a thin layer of ceramic tape, then use thick-film screen printing or other methods to deposit circuit traces and filler for the previously fabricated via holes 180. These fillers include tungsten inks and the like. Then, these individual layers are dried, stacked up and pressed (laminated) into a bar. There are often registration errors and stair-stepping is visible in the cross-sections of such via holes 180.

In the present invention, via holes are not formed in individual tape layers before stack-up. Instead, the alumina ceramic slurry can be thick-cast into tape and then laid down in layers or it may be injected, molded, powder pressed or the like to form a single monolithic structure. In this state, the alumina ceramic is still in the green and very pliable due to the organic binders and solvents that have been temporarily added to the system. It is at this point that via holes 180 are drilled therethrough from the outer surface (body fluid side) to an inner surface (AIMD electronic side) of the alumina substrate 188. Because the holes are drilled after formation of the pre-sintered ceramic alumina substrate 188, there is no requirement for registration with the consequential "stair-stepping" (due to misregistration) that is visible in cross sections of some prior art structures, for example those described in the Second Sight patents.

After via holes are formed, the pure platinum paste composition is injected under pressure or via vacuum into the via holes 180. The pressure or vacuum is carefully controlled in the present invention so that the platinum paste is driven intimately along the surface of the inside of the via such that the paste conforms to and creates a mirror image of the inner surface of the via in the alumina ceramic and, in so doing, interconnect with the already tortuous members prevalent in ceramic/particulate formation. A mutually conforming interface 191 is thereby formed between the platinum fill and the inside diameter of the via hole in the ceramic. Drilling is a preferred method of forming the via hole, but these via holes may also be formed by punching, laser drilling, water cutting or any other equivalent process.

As used herein, the term "essentially high purity alumina" means alumina ceramic with the chemical formula $Al_2O_3$. "Essentially pure" means that the post-sintered ceramic is at least 96% alumina. In a preferred embodiment, the post-sintered ceramic is at least 99% high purity alumina. Prior to sintering, the alumina may be a paste, a slurry or green state, and can contain organic solvents and binders. Once these organic solvents and binders are baked out, the alumina is sintered becoming essentially high purity alumina. Similarly, prior to sintering, the platinum paste also contains binders and solvents. The drilled vias of the ceramic insulator are filled with the platinum paste. It is after the binders and solvents are baked out at elevated temperature and then sintered that they are substantially removed and an essentially pure platinum via hole is created.

Figure 12:
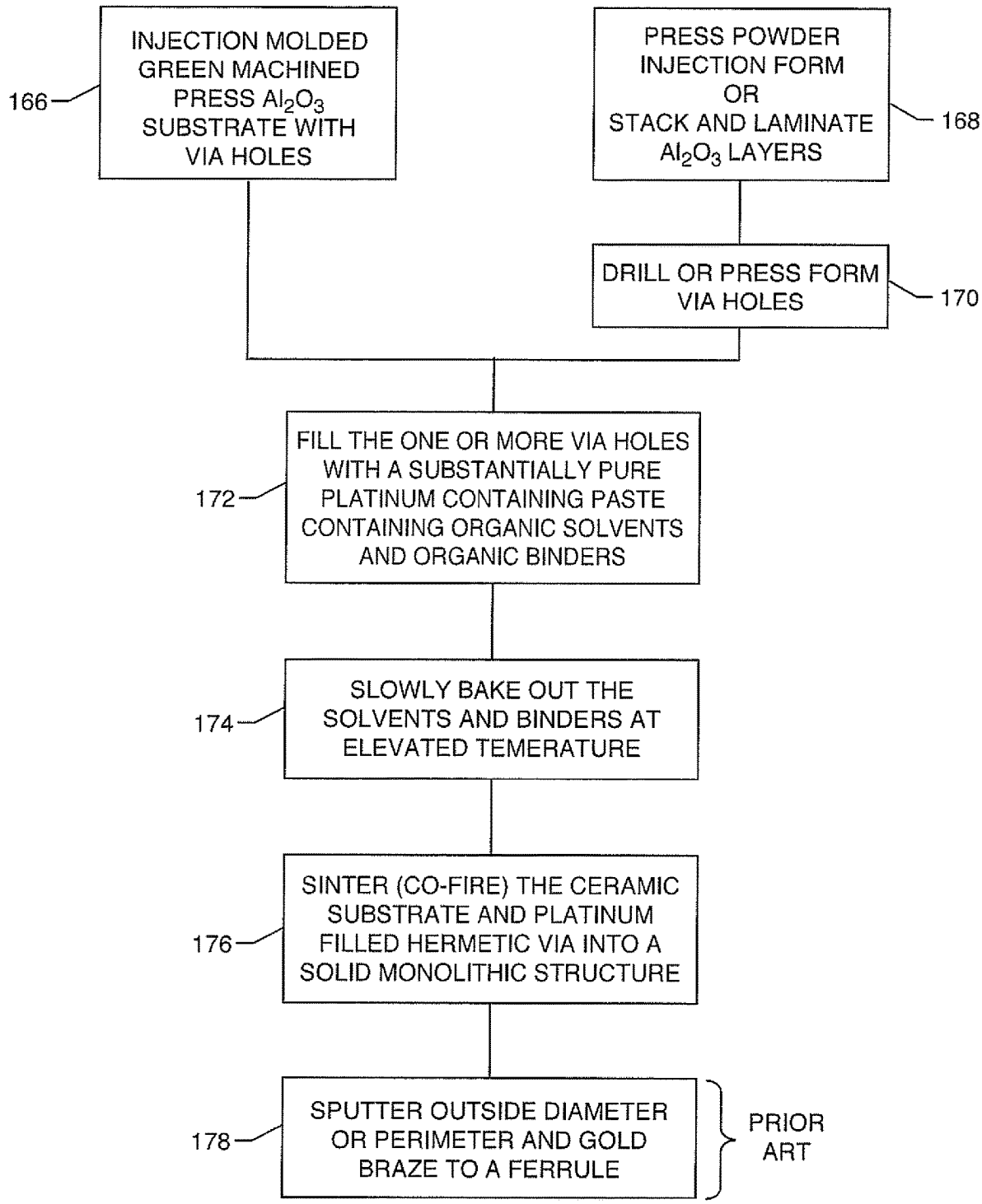
FIG. 12 is a flow chart illustrating the main steps of one embodiment of the process of the present invention.

One is referred to FIG. 12 which is a flow chart illustrating the main steps of the process of the present invention. First, an essentially high purity alumina substrate is formed. The essentially high purity alumina can be formed either through injection molding, green machining, powder pressing 166, by pressing powder into an injection die, or by tape casting and then stacking and laminating individual layers, under a pressure ranging from about 1,000 psi to about 5,000 psi at a temperature ranging from about 55-60° C. to about 85° C. or greater for about 5 minutes to about 15 minutes into a bar 168. After formation of the bar in step 168, the via holes are formed preferably by drilling through the structure, however punching, pressing, laser or waterjet operations may also be used to form the holes 170. All of the via holes would be filled in step 172 with an essentially pure platinum paste containing organic solvents and organic binders. It should be noted that organic solvents and binders also make up a percentage of the green essentially high purity alumina substrate. A further clarification is required here. As used herein, "essentially pure" means essentially pure post-sintering once the bulk of the binders and solvents have been baked out in step 174 and/or sintered in step 176, both at elevated temperature. Once the binders and solvents have been driven out of the system and sintering 176 has occurred, the result is a solid monolithic high purity alumina substrate 188 with one or more pure platinum-filled via holes 180 extending from an alumina substrate 188 outer surface to an inner surface. The outside diameter or the perimeter of the alumina substrate can now be prepared for attaching a ferrule 122 as previously illustrated in FIGS. 5, 7 and 8. In the present invention, the ferrule 122 is attached using conventional prior art techniques. That is, the outside diameter or perimeter of the sintered alumina substrate 188 is metalized (sputtered). The metallization would typically be in two layers with a first layer being an adhesion layer and the second layer being a wetting layer 150. Then the ferrule is attached to these metalized ceramic layers through a gold brazing process (step 178) wherein, pure gold is reflowed such that it wets the titanium ferrule and also wets to the metallized surfaces that were previously sputtered onto the alumina ceramic. Again, this ferrule attachment method is very common in the prior art.

The present invention centers around three enabling areas: (1) via packing with a high solids loading in the paste, (2) compression by the ceramic of the metal paste during binder bake out and sintering, and (3) a controlled cool down rate in combination with interfacial bonding sufficient to tolerate coefficient of thermal expansion (CTE) mismatch.

Metal/ceramic compatibility is an important factor in manufacturing hermetic terminals. The difference in CTEs of the metal and ceramic is recognized as a major parameter in predicting compatibility. The thermal expansion of metal is generally considerably greater than those of ceramics. For example, at a bakeout temperature of 500° C., the CTE of alumina is $7.8\times10^{-6}$/K and of platinum is $9.6\times10^{-6}$/K. Historically, CTE differences within 0.5 to $1.0\times10^{-6}$/K between the mating metal and ceramic materials are adequate to sustain hermetic bonding between these materials. However, it is believed differences beyond these limits provided at the bake out temperature for the alumina/platinum pair may produce sufficient tensile stresses at the interface during cool down to cause spontaneous bonding failure. Hence, given the significant difference in CTEs, even at a relatively low temperature of 500° C., achieving a hermetic seal between the platinum metal and alumina ceramic would not be expected if the difference in CTE between the sintered alumina and the platinum metal exceeds 0.5 to $1.0\times10^{-6}$/K. Rather, the present invention achieves a hermetic feedthrough structure through the controlled fabrication process parameters of the platinum metal particle solids loading within the paste, controlled packing of the platinum paste within the via, and the controlled shrinkage of the alumina substrate and platinum via paste through a prescribed co-fire heating profile.

In addition, a highly irregular surface at the material interface between the alumina substrate and the platinum metal particles within the via provides a mechanical contribution to adherence and robustness of the hermetic seal. A surface roughness produced by drill bits, sandblasting, grit-blasting or chemical etching of the metal substrate can increase the surface area and, in so doing, provide for a stronger mechanical attachment along the mutually conformal interface. Applying this concept to the alumina/platinum interface therein provides for another novel aspect of the present invention. Examples of sandblasting and grit-blasting media include sand, sodium bicarbonate, walnut shells, alumina particles or other equivalent media.

In the present invention, to achieve sustainable hermeticity, the following is required. Because the CTE of platinum is sufficiently higher than the CTE of alumina, it is not theoretically possible for alumina to provide compressive forces on a platinum body in a via. Hence, to overcome the CTE differences between these two materials, the platinum body in the via must be formed using a paste, a slurry or the like, having a minimum of 80% solids loading. In a preferred embodiment, the solids loading of the platinum particles within the paste is 90%. In a more preferred embodiment, the solids loading of the platinum particles within the paste is 95%. In addition, the via must be packed with the platinum paste to occupy at least 90% of the available space within each via opening. In a preferred embodiment, the platinum paste is packed within the via opening to occupy 95% of the space. In a more preferred embodiment, the platinum paste is packed to occupy 99% of the via opening. The shrinkage of the alumina must be no greater than 20% of that of the platinum fill in the via. In a preferred embodiment, shrinkage is 14%. In a more preferred embodiment, shrinkage is 16%.

Furthermore, the assembly is exposed to a controlled co-firing heating profile in ambient air that comprises a binder bakeout portion, a sintering portion and a cool down portion. In an embodiment, the binder bakeout portion is performed at a temperature of between 400° C. to 700° C. for a minimum of 4 hours. A preferred binder bakeout is at a temperature of between 550° C. to 650° C. A more preferred binder bakeout is at a temperature of between 500° C. to 600° C. The sintering profile portion is preferably performed at a temperature ranging from 1,400° C. to 1,900° C. for up to 6 hours. A preferred sintering profile has a temperature between 1,500° C. to 1,800° C. A more preferred sintering temperature is between 1,600° C. to 1,700° C. The cool down portion occurs either by turning off the heating chamber and allowing the chamber to equalize to room temperature or, preferably by setting the cool down portion at a rate of up to 5° C./min from the hold temperature cooled down to about 1,000° C. At 1,000° C., the chamber is allowed to naturally equalize to room temperature. A more preferred cool down is at a rate of 1° C./min from the hold temperature to about 1,000° C. and then allowing the heating chamber to naturally equalize to room temperature. In so doing, the desired outcome of achieving a robust hermetic seal is achieved between the mating materials of the alumina and platinum. It is noted that these materials have a CTE mismatch beyond the limits heretofore recognized as adequate for sustained bonding.

During processing of the platinum fill densities and additionally during the densification phase, compression is imparted by the alumina around the platinum within the via due to the shrinkage of the alumina being greater than that of the platinum. Furthermore, the platinum is sufficiently malleable at this phase to favorably deform by the compressive forces being applied by the alumina. The combination of the platinum solids loading, the platinum packing in the via and the shrinkage of the alumina being greater than the platinum fill results in the platinum taking the shape of the mating alumina surface. The amount of platinum solids loading, its packing percentage within the via and the malleability of the platinum material all contribute to formation of a hermetic seal between the platinum and alumina. In addition, the compressive forces that result from the greater shrinkage of the alumina substrate than that of the platinum within the via limit expansion of the platinum and force the platinum to deform such that it forms a hermetic seal. Thus, an interface between the alumina and platinum materials that conforms to the respective interface surfaces and results in a nearly exact mirror image of the interfacing surfaces is formed, thereby creating a hermetic bond therebetween. This mutually conformal interface is critical, particularly as researchers studying bonding between alumina and platinum believe that any strength in the bonding between the alumina and platinum is physical.

As noted earlier, strong bonding between the alumina and the platinum is the most important factor in achieving sustainable hermeticity in feedthrough terminals for AIMDs. The inventors have learned that the co-fire parameters used to form the hermetic terminals of the present invention provide unanticipated, but novel benefit of leveraging the catalytic nature of platinum, that is, platinum's affinity for certain elements, which enables either direct bonding or formation of an interfacial layer between the two materials. Analysis of the interface between the alumina and the platinum of this invention disclosed not only the creation of an intimate knitline, but, in the case of the interfacial layer, a hermetic structure that exhibits an amorphous layer at the knitline comprising the elements platinum, aluminum, carbon and oxygen that appears to impart resistance to erosion by body fluids. Both these bonding mechanisms, direct bonding and an amorphous interfacial layer, offer additional tolerance to the GTE mismatch between these two materials.

Figure 13:
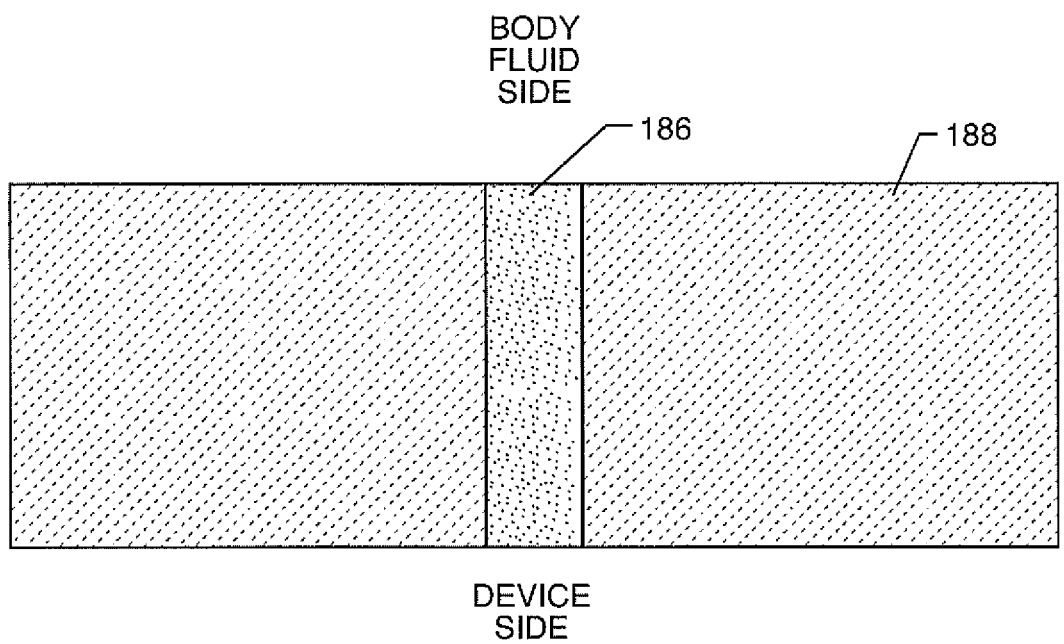
FIG. 13 is a sectional view of a hermetic terminal assembly of the present invention comprising a high purity alumina ceramic and a pure platinum filled via hole in a green state.
Figure 14:
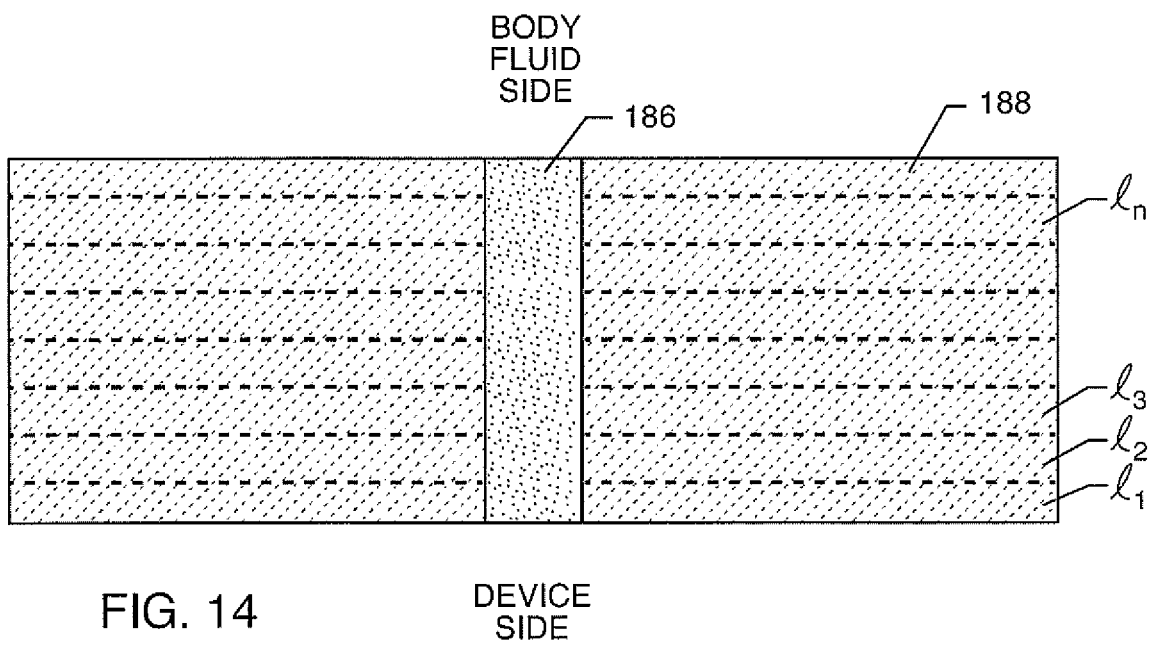
FIG. 14 is another sectional view of a hermetic terminal assembly of the present invention now showing stacking build up from individual tape layers in a green state.

FIGS. 13 and 14 are simplified unipolar cross-sectional views (without ferrules) showing the essentially high purity alumina substrate 188 of the present invention with a pure platinum conductor 186 in via hole 180. The ceramic in FIG. 13 has been formed from a single monolithic body, either through injection molding or green machining or the like. In contrast, FIG. 14 illustrates that the alumina substrate 188 has been formed by stacking up individual tape layers L1, L2, L3 . . . Ln. In both cases, the platinum conductor 186 as a paste is injected into the via hole in such a way that it compacts and fills every ridge and valley of the inside diameter of the via hole itself imparting symmetry, intimacy and preserving tortuosity. This symmetry, intimacy and tortuosity, in turn, impart tolerance to shearing and/or tensile stresses that might develop during cool down and/or during service. Tolerance to these stresses, in turn, imparts sustainable hermeticity over the service life of an AIMD. For simplicity, in FIGS. 13 and 14, the two side walls of the via hole are shown as straight lines. In reality, these via holes have an irregular edge with high spots, low spots, little ridges and so on, imparted by the bound particulate materials used for the mating materials.

Figure 15:
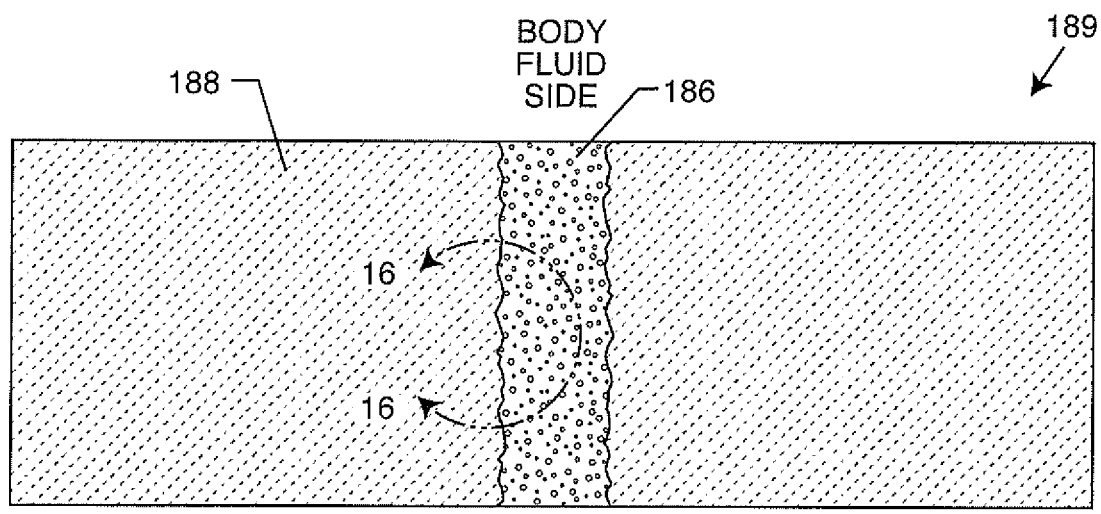
FIG. 15 is a sectional view of the hermetic terminal assembly of FIGS. 13-14 after a co-firing process.

FIG. 15 illustrates a co-fired high purity alumina hermetic terminal subassembly with a pure platinum conductor 186 of the present invention. The pure platinum conductor 186 forms a tortuous, intimate and mutually conformal interface 191 between the alumina substrate 188 and the platinum conductor 186.

Figure 16:
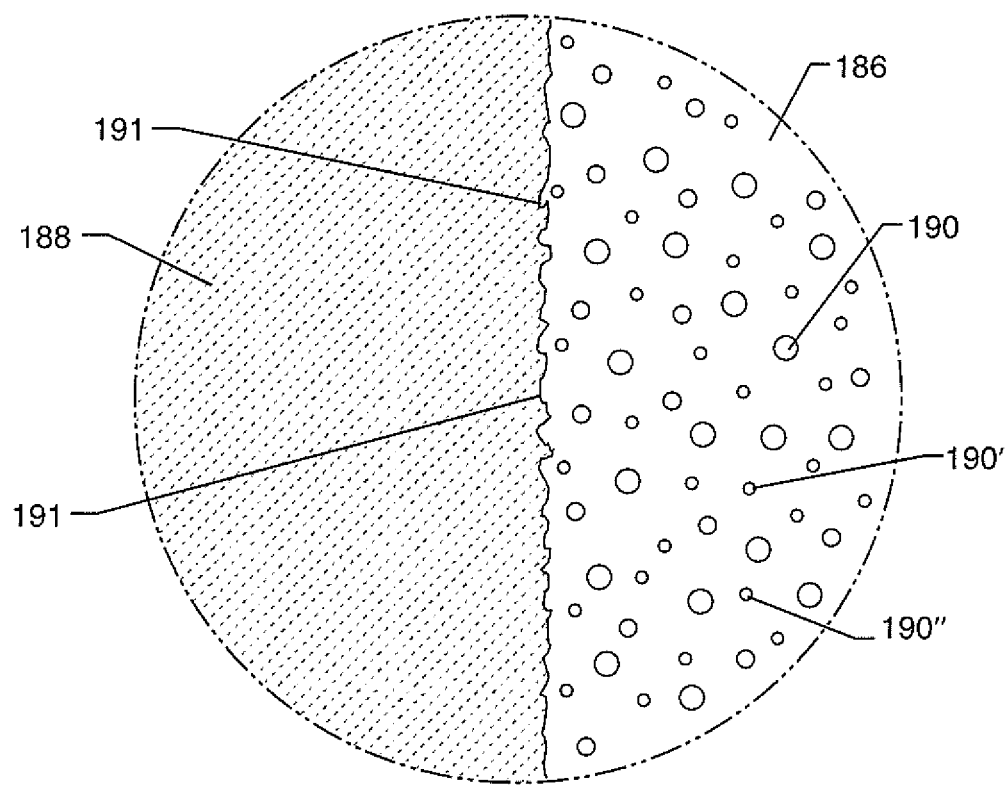
FIG. 16 is an enlarged view of the structure of FIG. 15 now showing a mutually conformal interface (or tortuous, intimate knitline)

FIG. 16 is taken from section 16-16 from FIG. 15 and shows the post-sintered condition wherein the platinum conductor 186 and the alumina substrate 188 form a tortuous, intimate, mutually conformal interface 191. The peaks and valleys of this tortuous surface are very important in the present invention as it increases the surface area of the mating surfaces which offers interfacial intimacy that imparts tolerance for mismatch in the CTE between the high purity alumina substrate 188 and the sintered pure platinum conductor 186. During thermal excursion, stresses can develop at the interface between the alumina substrate 188 and the pure platinum conductor 186 as shown in FIG. 16. This is where the tortuous surface becomes very important. The ridges and valleys that exist between the two surfaces of the mutually conformal interface 191 form an intimate structure capable of withstanding compressive, tensile and sheer stresses. This is a result of a greatly increased contact surface area between the sintered alumina substrate material and the sintered pure platinum conductor 186. This greatly increased contact surface area improves the overall strength and helps sustain hermeticity of the pure platinum-filled via hole. Helium leak rates of no greater than $1\times10^{-7}$ std cc He/sec are readily achieved using this novel process. In preferred embodiments, the helium leak rate would be no greater than $1\times10^{-8}$, $1\times10^{-9}$, $1\times10^{-10}$, $1\times10^{-11}$ or even $1\times10^{-12}$ std cc He/sec.

Another important feature of the present invention is closed cell porosity 190 as shown in FIG. 15 in the pure platinum conductor 186. This closed cell porosity 190, 190', 190" is best illustrated in FIG. 16, which is a sectional view taken from section 16-16 from FIG. 15. Referring back again to FIG. 16, one can see there are a number of closed cell porosity 190, 190', 190" and the like. First of all, in the present invention, there are no ceramic powders, glasses or other additives (other than temporary binders and solvents) to the paste comprising the platinum conductor 186. Further, the platinum fill paste comprises at least 80% solids. Accordingly, when the present invention is sintered, a dense filled via with carefully controlled, well distributed, closed cell porosity 190 forms. The presence of these pores is not contiguous, and hence does not compromise the hermeticity of the overall structure of the platinum conductor 186. Also, given that a dense filled via forms, these pores are relatively few in number, so they have minimal, if any, effect on the overall resistivity of the via hole from one end to the other.

Figure 17:
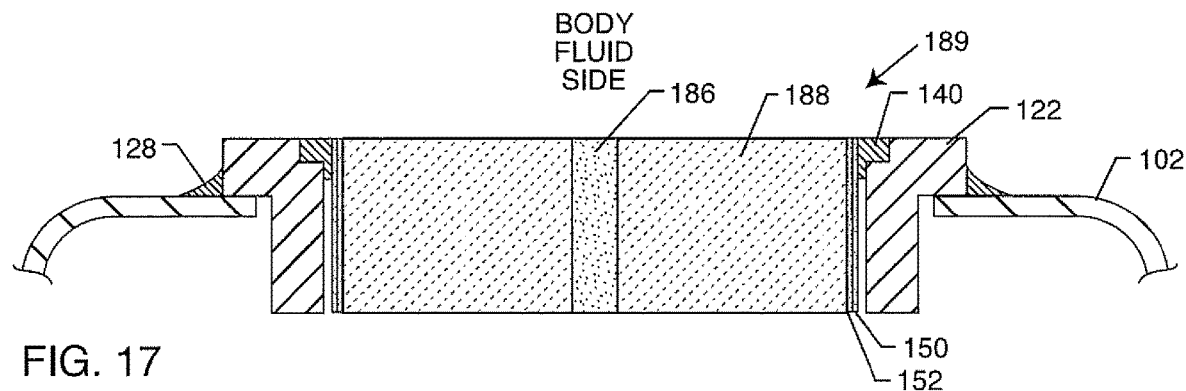
FIG. 17 is a sectional view of an embodiment of a novel hermetic terminal subassembly of the present invention installed in a housing of an AIMD.

FIG. 17 is a novel hermetic seal of the present invention. It has some features in common with prior art hermetic seals, particularly those illustrated in FIGS. 3, 5 and 8. The outside diameter of the alumina substrate 188 has metalized surfaces comprising wetting and adhesion layers 150 and 152 so that gold braze 140 can be melted and hermetically bonded to the alumina substrate 188 and the ferrule 122 of the hermetic terminal subassembly 189. As in the previous drawings, the ferrule 122 may be installed into the AIMD housing 102 by laser welding 128, or the like. As previously mentioned, it is a major goal of the present invention to eliminate the highly expensive biocompatible and noble leadwires 118, as previously illustrated in FIGS. 3, 5 and 8. Referring once again to FIG. 17, it is apparent that instead of a feedthrough leadwire, the present invention comprises a pure platinum conductor 186. It is a novel feature of the present invention that this platinum conductor 186 be of essentially pure platinum that is co-fired with the essentially high purity alumina substrate 188.

Figure 17A:
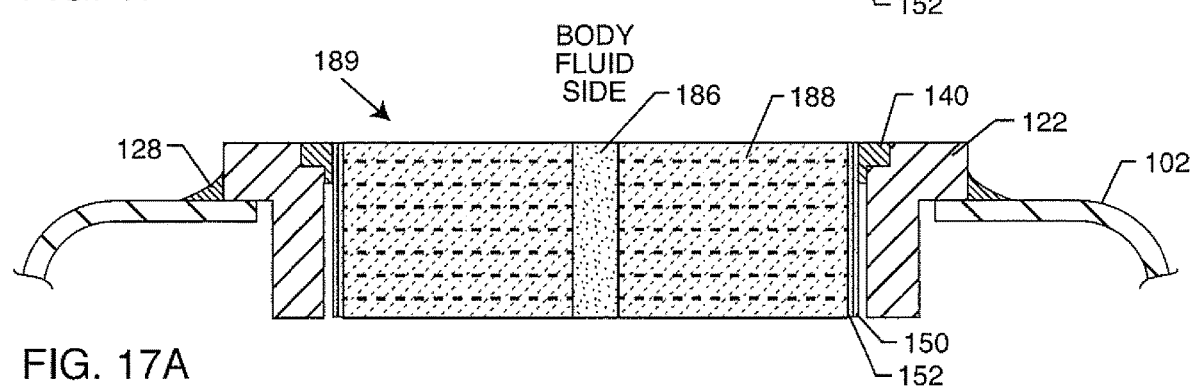
FIG. 17A is a sectional view similar to FIG. 17 showing individual tape layers comprising the insulator.

FIG. 17A is similar to FIG. 17 except that the alumina substrate 188 has been laid down in individual tape layers. After sintering, these individual layers form a monolithic structure and are very difficult, if not impossible, to discern.

Figure 17B:
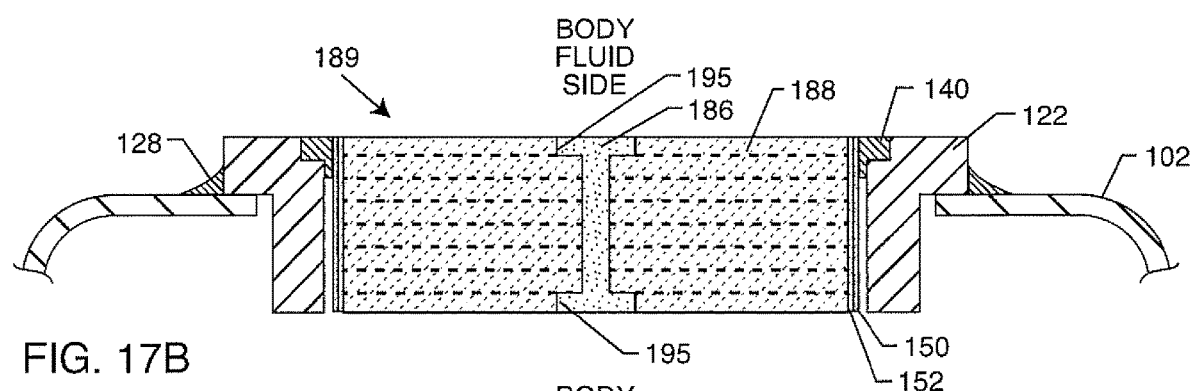
FIG. 17B is a sectional view similar to FIGS. 17 and 17A now showing the platinum filled via with a smaller diameter center section as compared to the ends of the platinum filled via.

FIG. 17B is very similar to FIGS. 17 and 17A except that the novel platinum conductor 186 has counter-bores 195 shown on both ends. It will be obvious to those skilled in the art that these counter-bores 195 could be counter-sinks, counter-bores or any shape and they could be at both the top and the bottom of the substrate surfaces as shown. They could also be just on one side of the substrate (not shown). This permits use of a very thin diameter via hole which saves on the amount and expense of pure platinum while at the same time provides a large surface area for a ball grid array attachment, for example, of a feedthrough capacitor as will be described in subsequent drawings.

Figure 18:
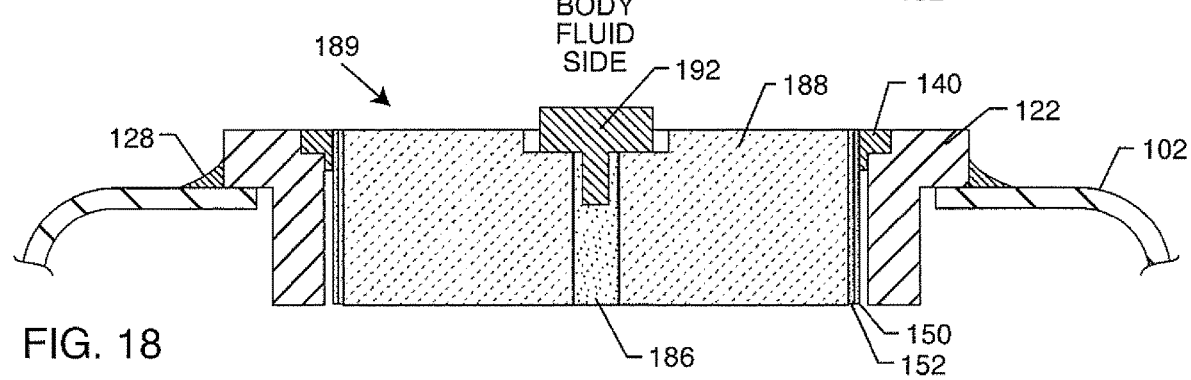
FIG. 18 is a sectional view similar to FIGS. 17, 17A and 17B now showing a wire bond cap co-fired into the platinum filled via.

FIG. 18 is very similar to FIGS. 17 and 17B except that a novel wire bond pad 192 has been placed on top of the platinum conductor 186. In a preferred embodiment, this wire bond pad 192 could be of similar compatible metal, like pure platinum, such that it could be co-fired, to electrically and mechanically connect to the platinum conductor 186. This wire bond pad 192 can be placed on the top side as shown, or the bottom side, not shown, or both sides depending on the application and how wires would be routed to an implanted lead, an AIMD connector-header block, or the like. Referring once again to FIG. 18, the novel wire bond pad 192 can be set into a counter-bore hole as shown or it can be set flush or proud on the top surface of the alumina substrate 188, or any variation thereof. Referring once again to FIG. 18, an implantable lead conductor could be connected to a wire bond pad 192 located on the body fluid side. In general, the implantable lead conductor or header block leadwire 118 would have a distal electrode in contact with biological cells.

It has been demonstrated that in a normal patient environment, a patient can be exposed to EMI. This EMI can take many forms, such as that from cellular telephones, airport radars, microwave ovens, and the like. A new international standard ISO 14117 has evolved, which includes tests standards to which cardiac pacemakers and implantable defibrillators must be exposed in order to be qualified by the FDA. There are similar specifications for cochlear implants and neurostimulators. Accordingly, it is important to provide EMI filtering at the point of lead conductor ingress into the interior of the AIMD. It is best to decouple high frequency interference before it gets inside of the AIMD housing 102. Once inside an AIMD housing 102, as illustrated in FIG. 3, the EMI can undesirably cross-couple or re-radiate to sensitive circuits where it can disrupt the proper functioning of the AIMD. In extreme cases, pacemaker inhibition has been documented which is immediately life-threatening for a pacemaker dependent patient. Accordingly, there is a need in the present invention, to provide for EMI filtering at the point of implanted lead ingress into the implanted (medical device) AIMD housing 102.

Figure 19A:
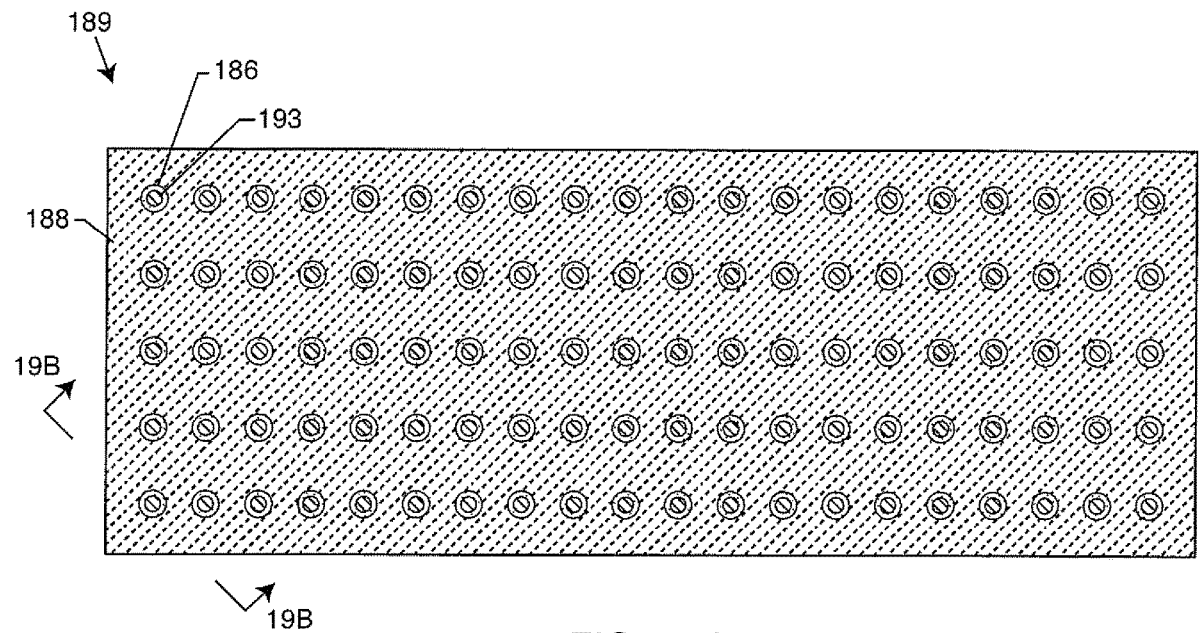
FIG. 19A is a top view of an exemplary embodiment of a hermetic terminal subassembly now showing a plurality of filled vias.

FIG. 19A is a top view of the novel co-fired high purity alumina ($Al_2O_3$) hermetic terminal subassembly 189 with one or more pure platinum conductors 186 of the present invention. This configuration illustrates that the present invention is capable of very large-scale integration. That is, a hundred or even a thousand novel platinum conductors 186 can be placed in a high purity alumina substrate 188. In addition, these platinum conductors 186 on the body fluid side may have a metal protrusion 193 which is co-fired into the platinum conductor 186. For example, the metal protrusion 193 may be used to form a nerve stimulation electrode. This configuration would be ideal, for example, in a retinol stimulation application.

Figure 19B:
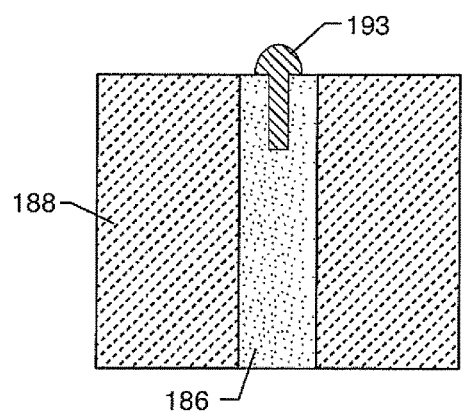
FIG. 19B is a sectional view taken from lines 19B-19B of FIG. 19A now showing a neuro-electrode co-fired into the platinum filled via.

FIG. 19B is a sectional view taken from section 19B-19B of FIG. 19A illustrating a high purity alumina substrate 188 which is co-fired with the pure platinum conductor 186. A neuro-electrode as a metal protrusion 193 is shown co-fired into the platinum conductor 186. In a preferred embodiment, the metal protrusion 193 would be of platinum so it has a CTE identical to the platinum via material. The metal protrusion 193 can also comprise titanium, iridium, niobium, rhodium, and/or palladium.

Figure 19C:
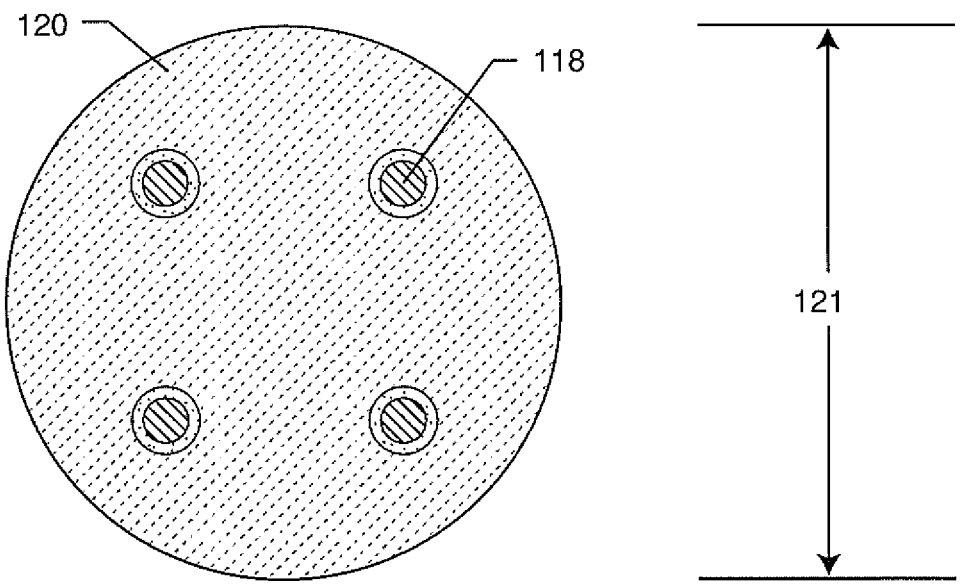
FIG. 19C is a top view of a prior art quad polar hermetic feedthrough.

FIG. 19C is a top view of a prior art quad polar hermetic feedthrough using traditional leadwires 118 and gold braze techniques. This is within a diameter 121, which is typically between 0.100 and 0.140 inches.

Figure 19D:
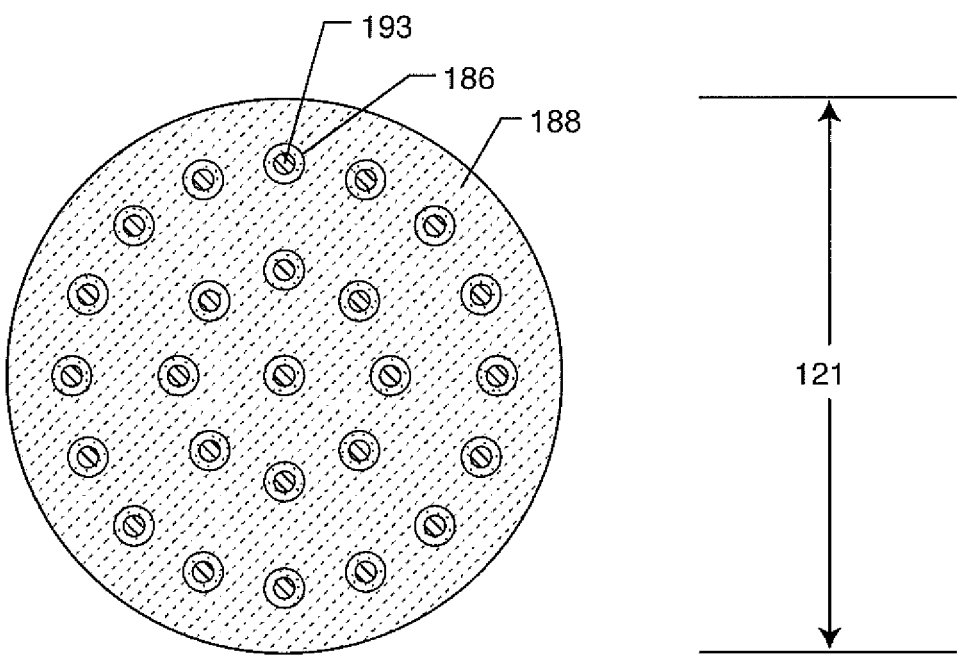
FIG. 19D is a top view of the novel hermetic terminal subassembly showing the increased number of leadwires possible as compared to FIG. 19C.

FIG. 19D is a top view very similar to FIG. 19C and is within the same exact diameter 121 as previously described in FIG. 19C. FIG. 19D is a dramatic illustration of the very large-scale integration that can be accomplished by the solid pure platinum via hole filling of the present invention. In this case, there are 25 via holes in the same space previously occupied by the four vias illustrated in FIG. 19C.

Figure 20:
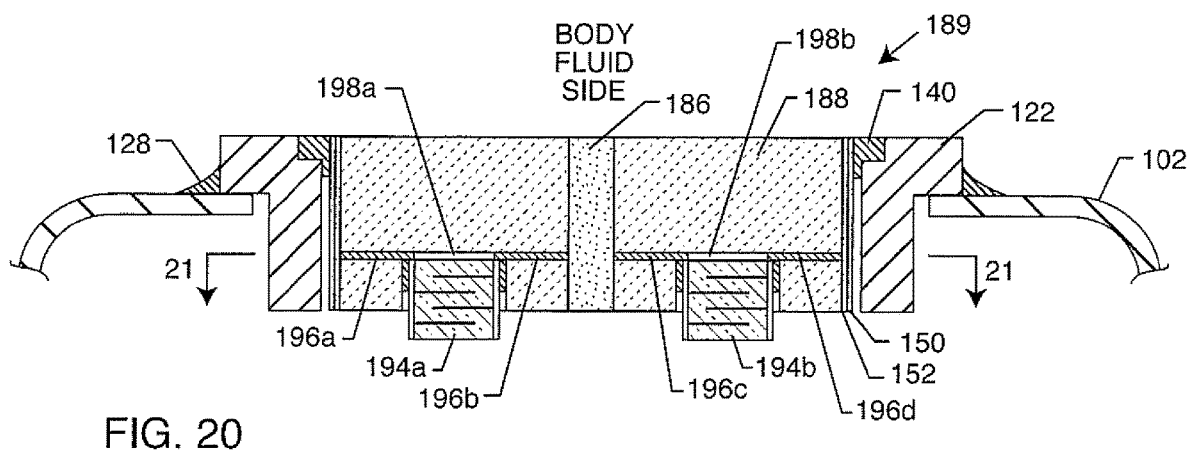
FIG. 20 is a sectional view of an exemplary embodiment of a hermetic terminal subassembly of the present invention now showing castellations with MLCCs.

FIG. 20 illustrates the present invention wherein, two castellation cavities 198a and 198b have been formed for convenient insertion of MLCCs 194a and 194b. Internal ground circuit trace 196a is provided at 194a which connect to the ground metallization adjacent the ferrule 122. On the opposite side of the MLCC 194a, there is an internal active circuit trace 196b. Active circuit traces 196b and 196c are connected to the platinum conductor 186. In this way, the two capacitors 194a and 194b are electrically connected to the center platinum conductor 186 and at their opposite ends they are also electrically connected to ground through vias with a metallization comprising wetting and adhesion layers 150 and 152 to gold braze 140 and, in turn, to the ferrule 122. Importantly, the ferrule 122 is connected to the overall equipotential electromagnetic shield surface of the AIMD housing 102. This equipotential surface of the AIMD housing 102 is herein defined as a ground. It will be obvious to those skilled in the art that one MLCC 194a may be used or a multiplicity of capacitors and individual castellation holes could be used. In some applications, it would be useful to use staggered values of MLCCs so that they are self-resonant at different frequencies. This allows them to filter over a much broader range of EMI frequencies. One is directed to U.S. Pat. Nos. 5,650,759 and 5,896,627 which show MLCCs adjacent to a hermetic terminal subassembly for human implant. The contents of these two patents are incorporated herein by reference. One is also directed to U.S. Pat. Nos. 5,959,829 and 5,973,906 which show the advantage of staggering chip capacitors and using specially formed chip capacitors. The contents of these two patents are also incorporated herein by reference.

Figure 21:
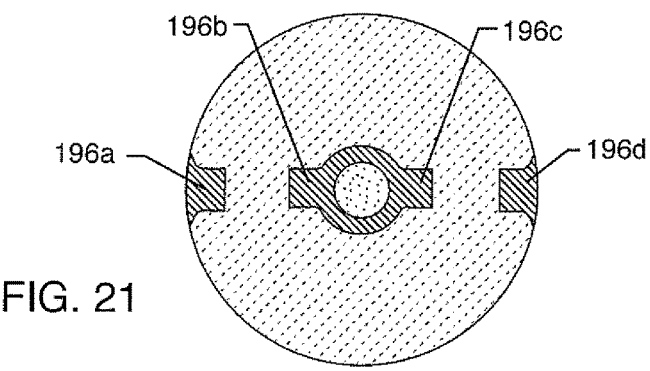
FIG. 21 is a sectional view taken from FIG. 20 along lines 21-21 now showing internal circuit traces.

Referring to FIGS. 20 and 21, it will be obvious to those skilled in the art that the MLCCs have terminations on each end, which connect to internal electrode plates of opposite polarity. One set of ground electrode plates will be electrically connected to the ground circuit trace 196a (electrical connection material not shown). The other end of the MLCC 194a will be connected to the active circuit trace 196b. A similar construction applies to the second MLCC 194b. Its ground electrodes are connected to ground circuit trace 196d and its active electrodes are connected to active circuit trace 196c. One can see that very short length circuit traces 196 are obtained wherein the MLCCs 194 act as variable frequency diverters. That is, at high frequencies, such as undesirable EMI frequencies, the capacitors will present a low impedance and thereby divert unwanted or even dangerous EMI coupled to the implanted lead(s). This EMI RF energy will be diverted through capacitors 194a and 194b to the ferrule 122 and then harmlessly to the overall electromagnetic shield of the AIMD housing 102. As a side note, it would not work very well to place these two MLCCs at some distance down on a circuit board inside of the AIMD housing 102. The problem with this is that EMI is drawn inside the AIMD housing where it can cross-couple and re-radiate and cause numerous problems.

Figure 22:
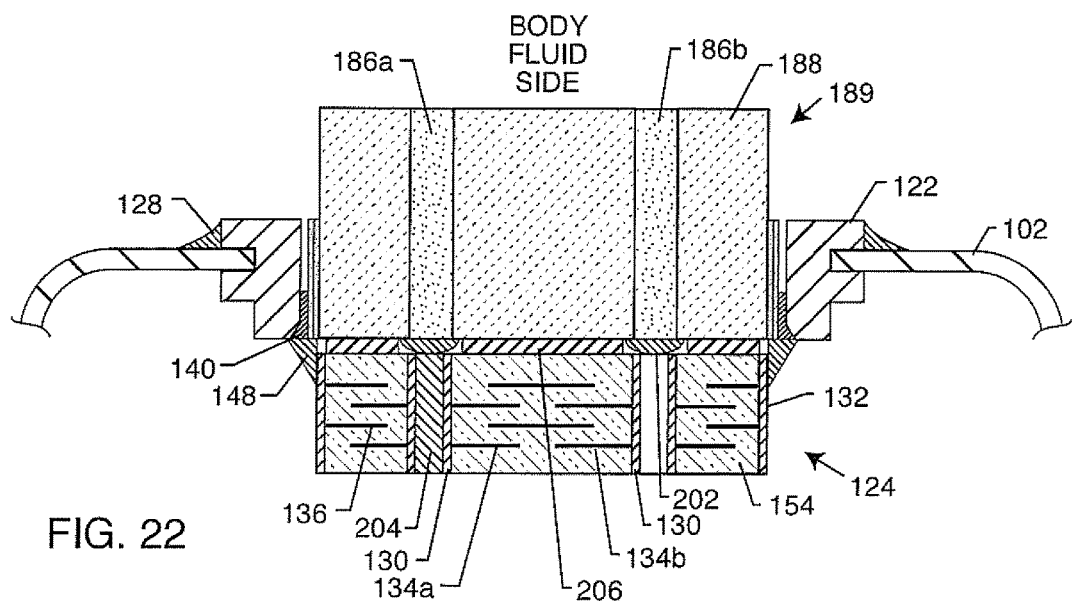
FIG. 22 is a sectional view of an exemplary embodiment of a hermetic terminal subassembly now showing a capacitor with a filled and a bore-coated via.

FIG. 22 is a cross-sectional view very similar to the quad polar hermetic terminal subassembly 116 and feedthrough capacitor 124 previously illustrated in FIGS. 7 and 8. One is directed to U.S. Pat. No. 8,179,658, which is incorporated herein by this reference, which shows a capacitor via within internal metallization electrically connected to a solid feedthrough leadwire. In the present invention, feedthrough capacitor 124 has been mounted directly to the surface of the co-fired high purity alumina ($Al_2O_3$) hermetic terminal subassembly 189 with one or more pure platinum conductors 186. The feedthrough capacitor 124 is first placed on the bottom surface of the co-fired high purity alumina ($Al_2O_3$) hermetic terminal subassembly 189 with one or more pure platinum conductors 186. In a preferred embodiment, an adhesively backed insulator washer 206 is used to affix the feedthrough capacitor 124 onto the surface of the alumina substrate 188. The insulator washer 206 has four stamped holes which align with the platinum conductors 186a through 186d and corresponding feedthrough holes of the feedthrough capacitor 124. There are two different methods of electrical attachment to the feedthrough capacitor illustrated. In the left-hand hole, we have a solid fill of a solder, braze or thermal-setting conductive material 204. A simplified electrical attachment is shown on the right side wherein, a solder bump or ball grid array (BGA) 202 is first dispensed and then the capacitor is aligned and placed over it. Then, temperature is applied to reflow the solder into place as shown. The solder makes electrical contact with the platinum conductor 186 and also with the internal metallization 130. The way this hermetic terminal subassembly 189 makes connection with implanted lead conductor or the leadwires 118 in a header block connector assembly or internal circuit connections will be shown in subsequent drawings. In accordance with good EMC principles, the feedthrough capacitor 124 is disposed immediately at the point of EMI ingress into the inside of the AIMD housing 102. In this way, high frequency EMI can be decoupled and diverted to the AIMD housing 102 without adversely effecting AIMD sensitive electronic circuits. Feedthrough capacitor 124 active electrode plates 134a and 134b are both connected to the internal metallization 130. The capacitor ground electrode plates 136 make contact with the capacitor outside diameter or external metallization 132. An electrical connection material 148 connects from the external metallization 132 to the gold braze 140 of ferrule 122. This makes a low impedance oxide free electrical connection which is superior for high frequency performance.

In comparison to the prior art leadwires 118 previously illustrated in FIGS. 7 and 8, the structure illustrated in FIG. 22 is ideal for robotic assembly. The problem has been one of the "forest of the trees." When one has a hermetic seal with say, eight to a dozen long platinum leadwires running through it, it becomes impossible with a production robot to insert a feedthrough capacitor down over all of those wires at once. This takes a human hand a considerable amount of time to thread each one of those leadwires through and finally then snug the capacitor up against the hermetic terminal subassembly 189. It will be apparent to one skilled in the art that the co-fired high purity alumina ($Al_2O_3$) hermetic terminal subassembly 189 with one or more pure platinum conductors 186 can be inverted and put into a robotic fixture holder. Then, BGA (ball grid array bumps) 202 can be formed and even the epoxy comprising the insulator washer 206 can be robotically formed or dispensed. The capacitor may be picked up by a pick and place robot with a vacuum head and perfectly aligned in place and then the entire assembly is heated to the point where the solder connections are made. This requires almost no human labor to accomplish compared to the highly intensive human labor of prior art assemblies. For example, referring back to FIG. 8 in the prior art, it is labor intensive to dispense sufficient quantities of electrical connection material 146 and 146'. First the capacitor has to be seated in place against the hermetic terminal subassembly. This is done against an insulator washer 206. It is very important that this be done under temperature and pressure such as there are no gaps or voids. Then, one can invert the assembly and using micro syringes, inject the thermal-setting electrical connection material 146 and 146' as best they can between the lead and the hole in the feedthrough capacitor. In order to get this material to drop into place, one must put the entire assembly into a centrifuge for a few minutes. Centrifuging drives the silver-filled thermally conductive adhesive down into place (partially fills the hole around the leadwire 118). This material is then pre-cured and then an abrasive microblast procedure is used to remove excess material that has gotten on top. This process is usually repeated from three to five times iteratively until the fill is void free and meets product requirements. Each time one fills one must do a pre-cure of the thermal-setting conductive adhesive and then an abrasive microblast followed by a multiple cleaning steps to remove any residual grit blast media, all of which involves a tremendous amount of labor and production yield issues. In contrast, the present invention of FIG. 22 is accomplished in seconds with no need for centrifuging or excessive cleaning steps (or even any cleaning steps).

Figure 22A:
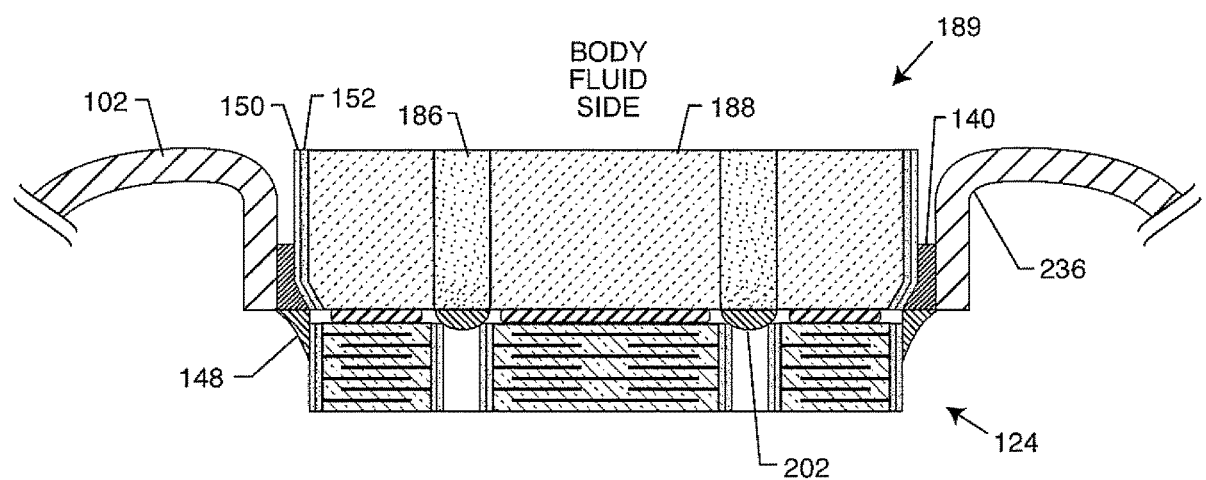
FIG. 22A is a sectional view similar to the structure of FIG. 22 now showing an exemplary embodiment without a ferrule where the insulator is attached to the AIMD housing.

FIG. 22A is similar to FIG. 22 except that the ferrule 122 has been completely eliminated. The ferrule 122 tends to be very expensive because it is machined from pure titanium. Accordingly, elimination of the ferrule 122 substantially reduces expense. In FIG. 22A, there is a direct gold braze 140 between the AIMD housing 102 and the metallization comprising wetting and adhesion layers 150 and 152 that are sputtered or plated on the co-fired high purity alumina ($Al_2O_3$) hermetic terminal subassembly 189 with one or more pure platinum conductors 186. In this case, the AIMD housing 102 has been stamped to form an L-bend 236. This L-bend 236 provides strength and stiffness in the area of the penetration through the AIMD housing 102 for mounting of the co-fired high purity alumina ($Al_2O_3$) hermetic terminal subassembly with one or more pure platinum conductors 186. It will be obvious to those skilled in the art that shapes other than the L-bend 236 could also be stamped to add strength.

Figure 23:
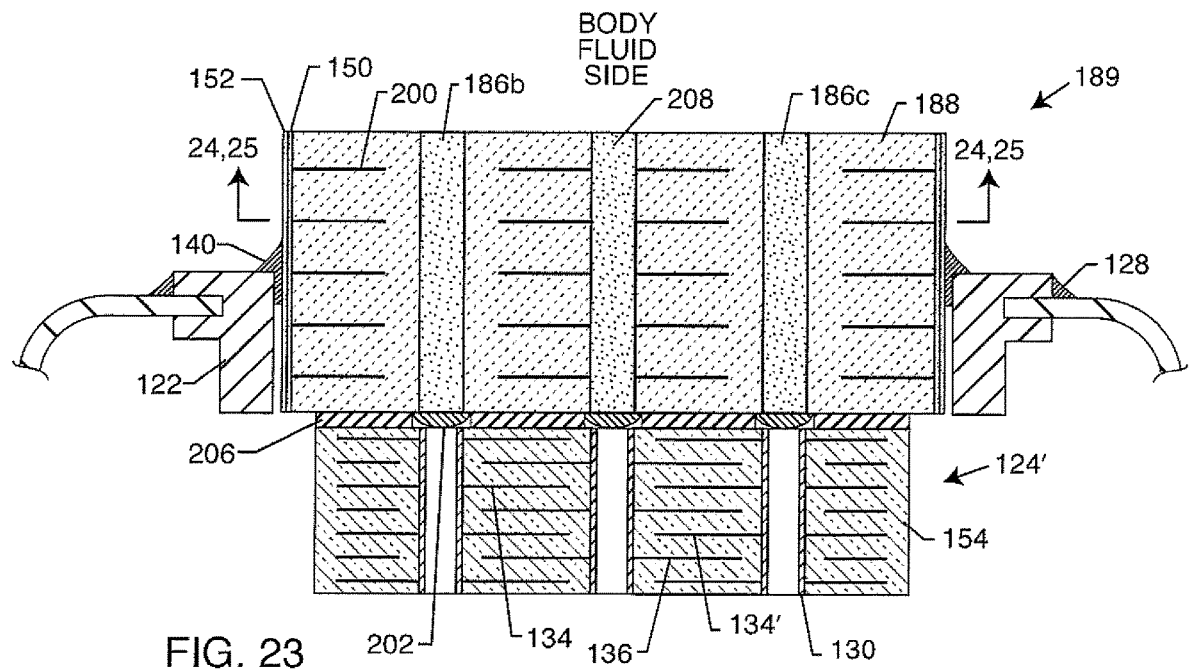
FIG. 23 is a sectional view of an exemplary embodiment of a hermetic terminal subassembly now showing a capacitor with an internal ground and an insulator with ground plates.

FIG. 23 is a very similar structure to FIG. 22 in that it is a quad polar feedthrough capacitor similar in function to what was previously described in FIGS. 7 and 8. In this case, the outside diameter or external metallization 132 of the feedthrough capacitor has been completely eliminated. This also eliminates the need to use an electrical connection material 148 around the perimeter or diameter of the feedthrough capacitor to the ferrule 122 and in turn, to a case ground provided by the AIMD housing 102. The reason for this is that ground electrode plates 200 have been formed in the co-fired high purity alumina ($Al_2O_3$) hermetic terminal subassembly 189 with one or more pure platinum conductors 186*b, c* of the present invention. One can see that the center via hole 208, which is filled with pure platinum, is also electrically connected to a plurality of ground electrode plates 200. These electrodes become grounded by means of being electrically connected to the wetting and adhesion layers 150 and 152. It is to these layers that the gold braze 140 makes an electrical and a hermetic connection between the ferrule 122 and the wetting layer 150. It is through this electrical connection that the ground electrode plates 200 inside of the co-fired high purity alumina ($Al_2O_3$) hermetic terminal subassembly 189 with one or more pure platinum conductors 186 are formed. An internally grounded feedthrough capacitor 124' is co-bonded to the co-fired high purity alumina ($Al_2O_3$) hermetic terminal subassembly 189 with one or more pure platinum conductors 186. Internally grounded hermetic insulators, such as insulator co-fired high purity alumina ($Al_2O_3$) hermetic terminal subassembly 189 with one or more pure platinum conductors 186 shown in FIG. 23, are further described in U.S. Pat. No. 7,035,076, the contents of which are incorporated herein by reference. Internally grounded feedthrough capacitors 124' are described in U.S. Pat. Nos. 5,905,627, 6,529,103, 6, 765,779 and 6,765,780, the contents all of which are incorporated herein by reference. The solid platinum conductors 186 of the co-fired high purity alumina ($Al_2O_3$) hermetic terminal subassembly 189 enable the BGA 202 dispensing and rapid or robotic assembly of the internally grounded feedthrough capacitor 124' to the overall hermetic terminal subassembly 189.

Figure 23A:
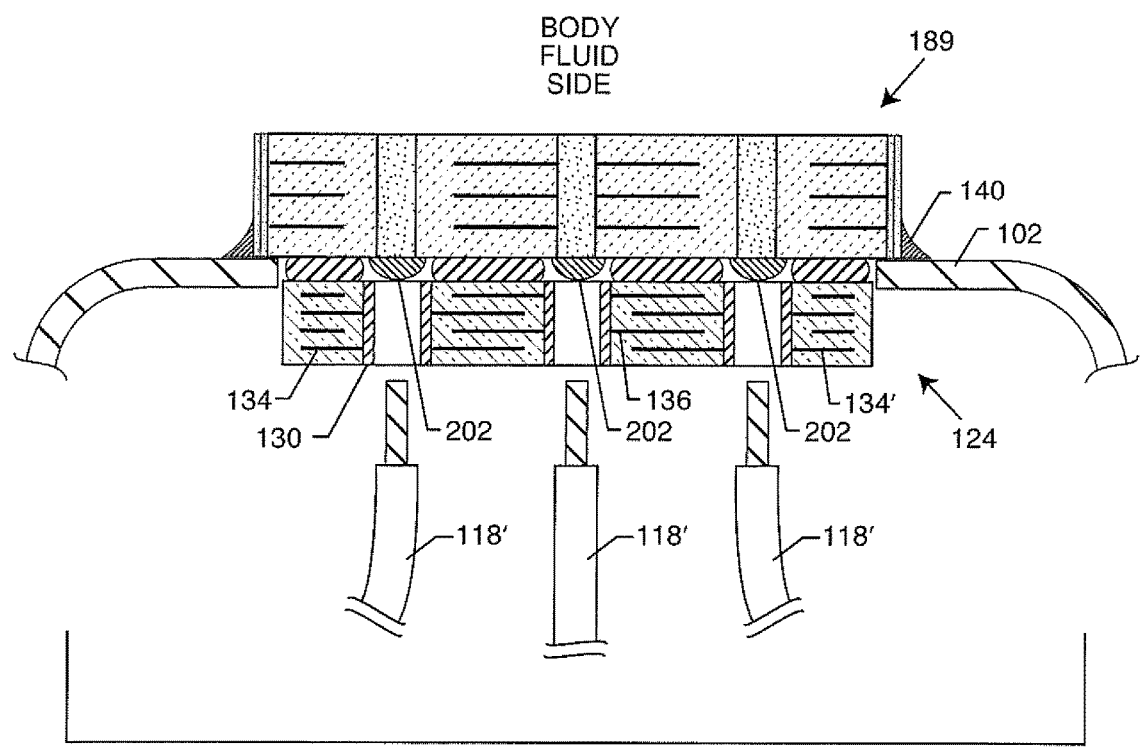
FIG. 23A is a sectional view similar to the structure of FIG. 23 now showing an exemplary embodiment without a ferrule where the insulator is attached to the AIMD housing.

FIG. 23A is similar to FIG. 23 except that the ferrule 122 has been eliminated. This is similar to the elimination of the ferrule 122 previously described in FIG. 22A except that in this case, the sides of the AIMD housing 102 do not have the L-shape previously described in FIG. 22A. Again, it will be obvious to those skilled in the art that when the ferrule 122 is eliminated, a direct braze 140 to the AIMD housing 102 can be accomplished by pre-forming the housing into a number of different shapes or even planar as illustrated in FIG. 23A.

Figure 24:
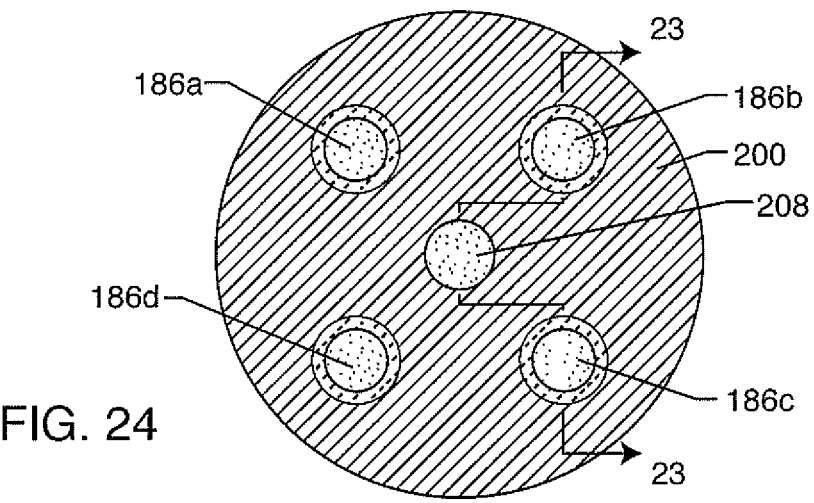
FIG. 24 is a sectional view of the ground plate of FIG. 23 taken along lines 24-24.

FIG. 24 illustrates the internal ground plate of the co-fired high purity alumina ($Al_2O_3$) hermetic terminal subassembly 189 with one or more pure platinum conductors 186 taken from section 24-24 of FIG. 23. Again, this is a quad polar structure in that there are four active platinum conductors 186*a*, 186*b*, 186*c* and 186*d* that are in contact with distal electrodes and biological cells. The central ground 208 does not have to come all the way to the body fluid surface. It could be in a blind hole (not shown). Referring to FIG. 24, the ground electrode plate 200 is preferably made of pure platinum or equivalent circuit trace material. The ground plate material may also comprise tungsten, iridium, rhodium and/or palladium.

Figure 25:
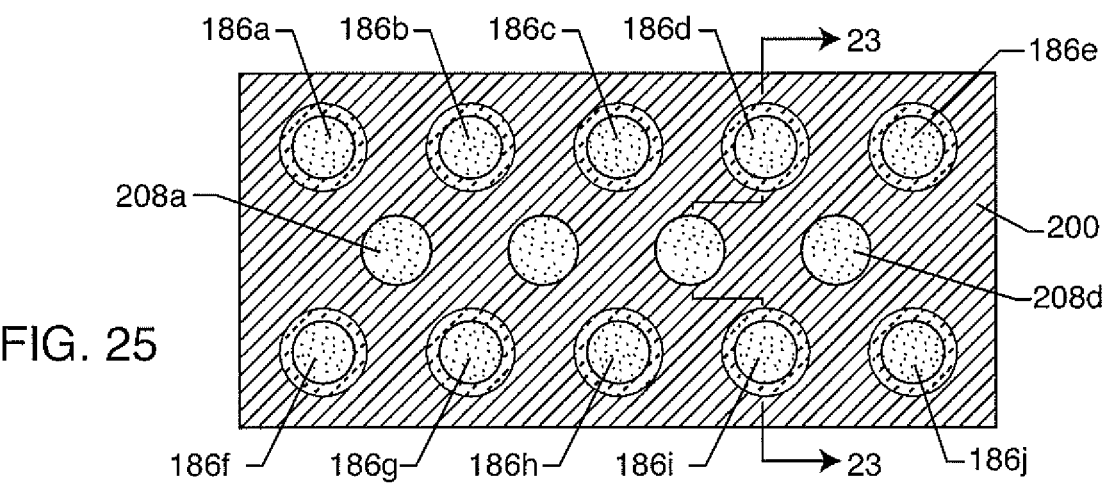
FIG. 25 is a sectional view of the ground plate of FIG. 23 taken along lines 25-25 now showing a ten leadwire configuration.

FIG. 25 is taken from section 25-25 of FIG. 23. Obviously, the isometric view of the device no longer conforms with FIG. 7 or 8 as it is no longer quad polar. Referring back to FIG. 25, ten active poles or platinum conductors 186*a* through 186*j* are illustrated. In this case, there are four grounded vias 208*a* through 208*d*. These grounded vias are symmetrically located and placed adjacent the active platinum conductors 186*a* through 186*j*. For example, referring to ground via 208*a*, it is exactly centered between active platinum conductors 186*a*, 186*b*, 186*f* and 186*g*. This is very important so that a low inductance and low impedance exists across the entire ground electrode plate 200 serving as a ground plane. As an extreme example, let's imagine for a minute that there was only one ground via in FIG. 25 and that was ground via 208*a*. In other words, imagine removing the ground vias 208*b*, 208*c* and 208*d*. This means that good EMI filtering would occur for the platinum conductors 186*a*, 186*b*, 186*f* and 186*g* as they are not very distant from the ground via 208*a*. However, a far different situation would occur for platinum conductors 186*e* and 186*j*. These would now be a long distance from the nearest ground via 208*a* and substantial inductance and resistance would result across the ground electrode plate 200. Therefore, there would not be nearly as effective EMI attenuation on these distant active platinum conductors 186*e* and 186*j*. The use of solid platinum filled vias is conducive for very large-scale integration. Literally, hundreds, if not thousands of through vias can be placed in a small footprint, which makes this an excellent application for neurostimulation, retinal stimulation, and the like.

Figure 26:
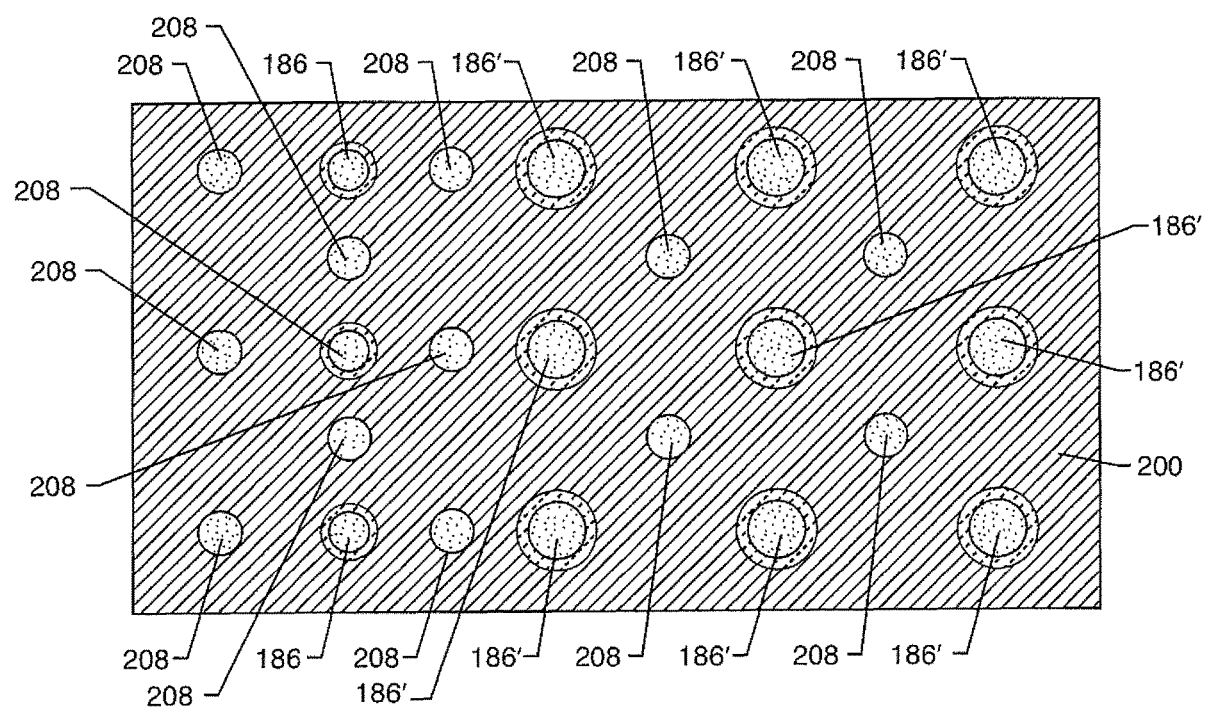
FIG. 26 is a sectional view similar to FIGS. 24-25 now showing extra ground vias to improve EMI filter attenuation.

FIG. 26 is similar to FIG. 25, but in this case, it shows a number of advantages of the present invention that are not immediately obvious. First of all, there are a multiplicity of ground vias 208 which assure that each one of the active platinum conductors 186 is a short distance in the ground electrode plate 200 from a grounded via 208. Also shown is that if one has a particularly sensitive circuit, such as a cardiac pacemaker sense circuit, one could place extra grounded vias 208 in close proximity to the active vias to further improve EMI filter attenuation. For example, platinum conductors 186 might connect to pacemaker sense circuits and these are placed in very close proximity to ground vias 208 on both sides. Vias also do not have to be the same diameter. Platinum conductors 186' are active circuit traces but are shown larger than platinum conductors 186. This might be necessary when large therapeutic pacing pulses are required, or in particular, for delivery of high currents during a high voltage shock from an implantable cardioverter defibrillator. FIG. 26 is only an example of one type of very large-scale integration. With the solid platinum-filled via technology of the present invention, it is possible to have hundreds if not thousands of vias in a very small footprint. This makes the present invention ideal for neurostimulators, retinal stimulators and the like.

Figure 27:
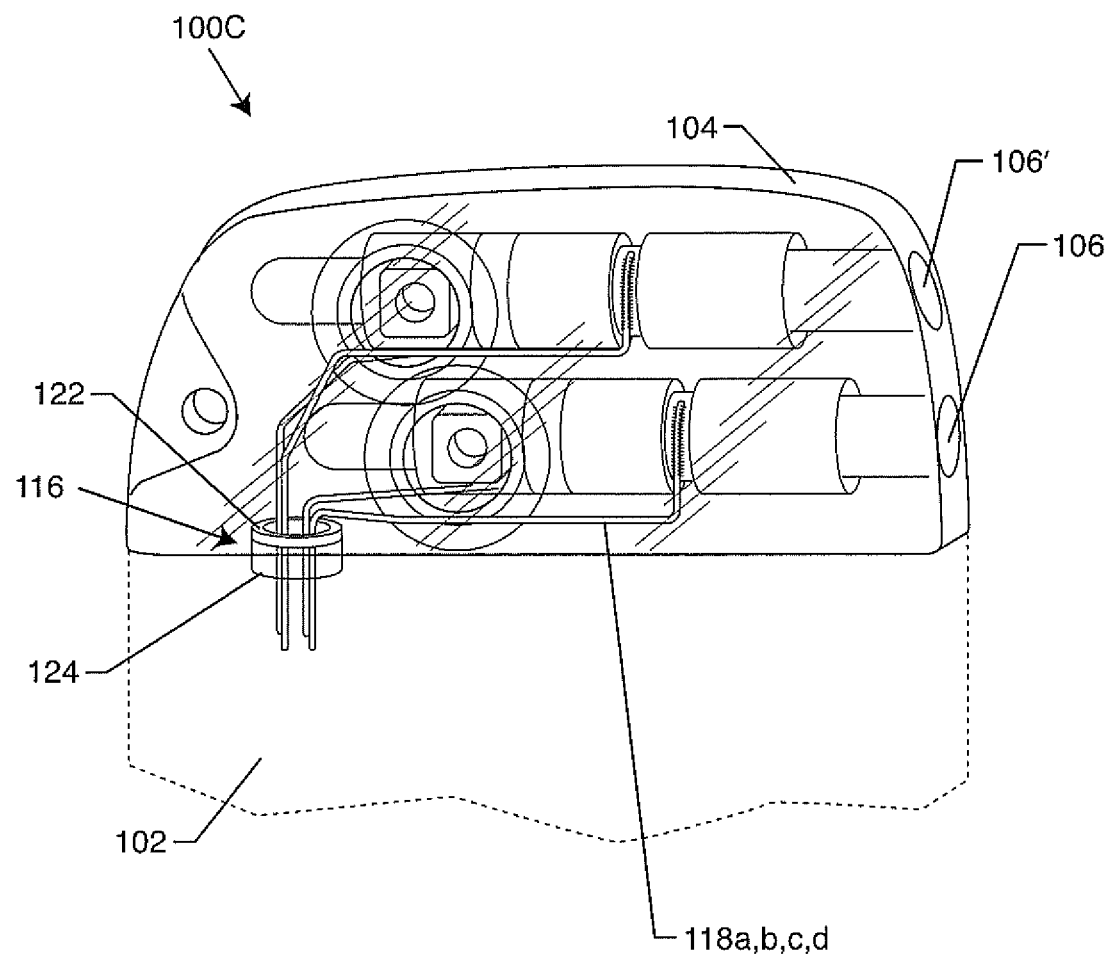
FIG. 27 is a perspective view of a prior art header block connector assembly.

FIG. 27 is similar to FIG. 2 in that it shows a prior art AIMD with a header block connector assembly 104. In this case, the medical device 100C is a cardiac pacemaker and the header block connector ports assemblies 106, 106' are IS-1 or DF-1 ISO Standard connector cavities. These are designed to receive the proximal plug of implanted leads 108, as previously illustrated in FIG. 3. Leadwires 118*a*, 118*b*, 118*c* and 118*d* within the header block connector assembly that are routed to the hermetic terminal subassembly 116, which has a ferrule 122 that has been laser welded into the AIMD housing 102. In general, the header block connector assembly 104 is not metallic. Most prior art header block connector assemblies are some sort of polymer material, such as Techothane, or the like. A prior art feedthrough capacitor 124, which was previously illustrated in FIG. 3, is also shown. The routing of the leadwires 118*a*, 118*b*, 118*c* and 118*d* in the header block connector assembly is a difficult operation. In most cases, jigs and fixtures are used to hold all the components of the header block connector port assemblies 106 and 106' in place while laser welding and attaching at the appropriate electrical contact points of the leadwires 118 takes place. In a prior art EMI hermetic terminal subassembly 116, these leadwires are typically quite long and of a biocompatible material, such as platinum iridium. In this configuration, it is required to preassemble all of the components, including the leadwires and then cast the Techothane in place. This is a difficult process because the Techothane must be cosmetically pleasing and completely free from any voids or air bubbles. Accordingly, an improved method of header block connector assembly construction and attachment is needed.

Figure 28:
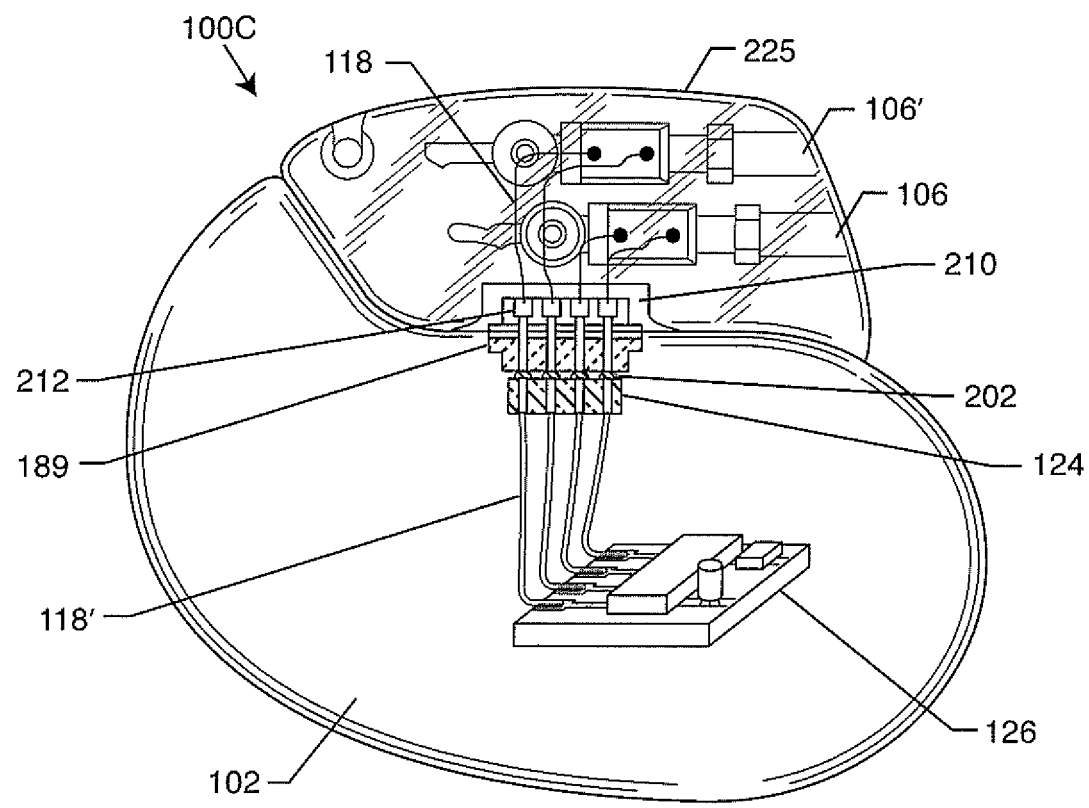
FIG. 28 is a side view of an exemplary embodiment of a novel side window in a header block of an AIMD.

FIG. 28 illustrates a novel header block connector assembly 225 of the present invention, which incorporates a side window 210. This construction allows the header block connector port assemblies 106 and 106' and their associated leadwires 118 to all be preassembled and then pre-molded in a separate operation. This allows the header block connector assembly 225 to be completely preassembled and pre-inspected and then later attached to the (pacemaker) AIMD housing 102. The leadwires 118 are routed and designed to hang down into the side window 210 where they can be attached later by laser welding, or the like, to wire bond pads 212 which are on the co-fired high purity alumina ($Al_2O_3$) hermetic terminal subassembly with one or more pure platinum conductors 186 of the present invention. One will also see that there is a novel ball grid array attached feedthrough capacitor 124. The ball grid array (BGA) attachments are shown as 202.

Referring once again to FIG. 28, illustrated are internal leadwires 118' which are routed from the novel feedthrough capacitor 124 to circuit board 126. The feedthrough capacitor 124 is novel due to a unique method of inexpensive leadwire attach during the ball grid array 202 attachment. Referring once again to FIG. 28, it will be appreciated that one is looking at the side view of two IS-1/DF-1 style header block connector port assemblies 106, 106'. There are actually four connectors in the medical device 100C, but in the side view, one can only see two header block connector port assemblies 106 and 106'. This makes for a total of eight leadwires 118. Again, for simplicity, only four leadwires 118 are shown in the FIG. 28 side view, but one skilled in the art recognizes any number of leadwires may be used with the present invention.

Figure 29:
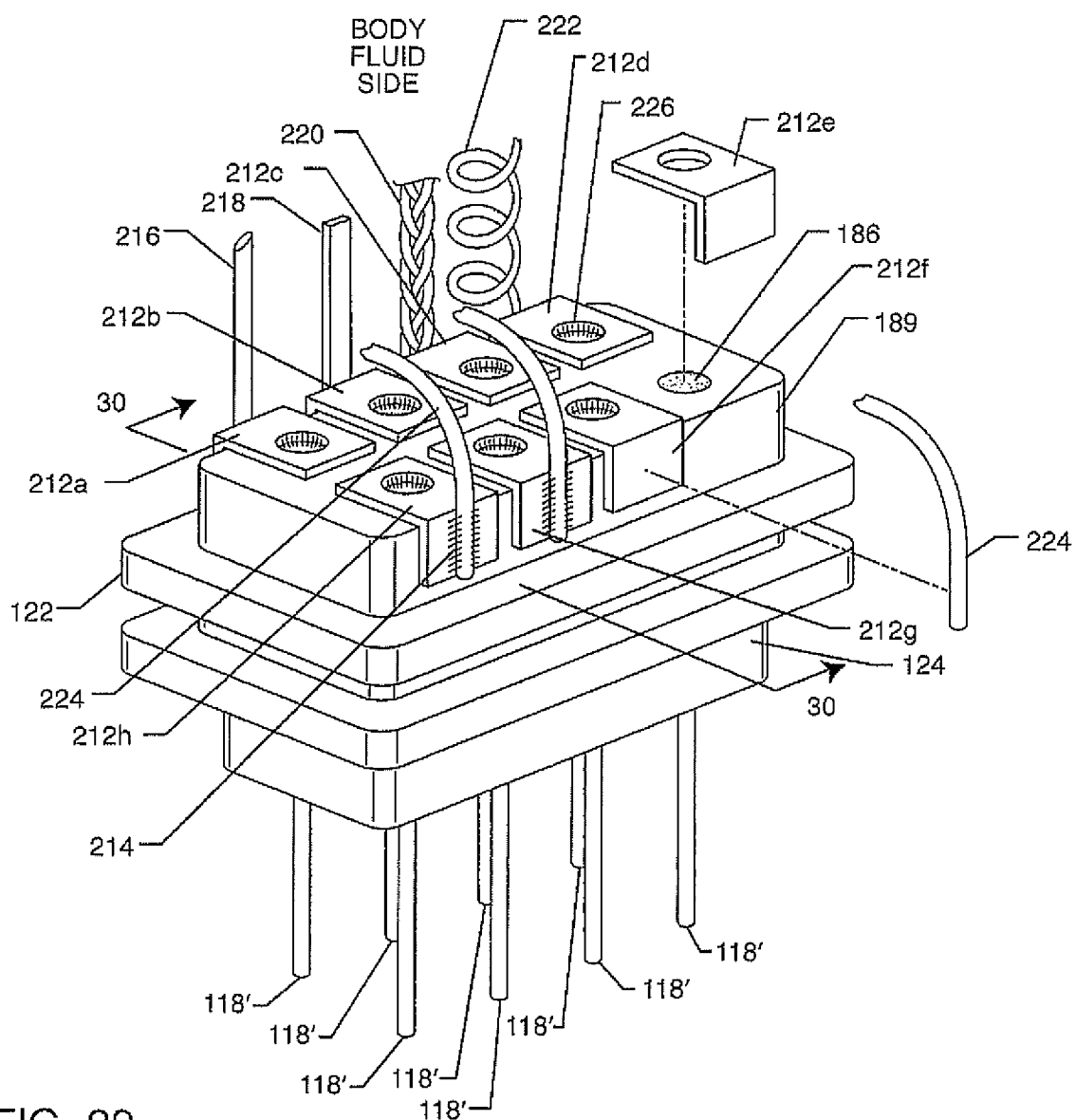
FIG. 29 is a perspective and enlarged view of a hermetic terminal assembly with various novel side attachment configurations accessible through the novel header block side window.

FIG. 29 is an exploded view of the novel co-fired high purity alumina ($Al_2O_3$) hermetic terminal subassembly 189 with one or more pure platinum conductors 186. First of all, FIG. 29 shows a very novel way to attach a wire bond pad 212 to the novel pure platinum conductor 186 in the via holes 180 of the present invention. Wire bond pad 212e is shown exploded away from the co-fired high purity alumina ($Al_2O_3$) hermetic terminal subassembly 189 with one or more pure platinum conductors 186 in the via holes 180. It is L-shaped to facilitate wire bonding in the novel side window 210 of the header block connector assembly 225 as previously illustrated in FIG. 28. Attachment of these L-shaped wire bond pads 212 is done by an electrical connection material 226. Since this is on the body fluid side of the invention, it is important that this electrical attachment material be non-toxic and biocompatible. This can be a laser weld, a gold braze, a thermal-setting conductive adhesive, or the like. Long term biocompatible thermal-setting conductive adhesive would usually be loaded with a pure platinum, gold, or silver flake material.

Referring once again to FIG. 29, one can see that the side mounted wire bond pad 212 is suitable for attachment of a variety of types, shapes and sizes of leadwires which would be extending down into the header block connector assembly side window 210. For example, leadwires 216, 118 could be oval, leadwires 218,118 could be a flat ribbon wire, leadwires 220, 118 could be a braided or stranded wire, leadwires 222, 118 could be a coiled wire and of course, leadwires 224, 118 could be a simple round wire. Internal leadwires 118' for an AIMD are shown as they exit the feedthrough capacitor 124 and are directed to AIMD internal circuits, for example, to circuit board 126 previously illustrated in FIG. 28. The various leadwires 216 through 224 are attached to the wire bond pads 212 using an electrical attachment material 214. In a preferred embodiment, the electrical attachment would be done by laser welding. Referring once again to FIG. 28, the side window 210 is left open for easy access by laser welders or resistance wire bonders, or the like. The header block connector assembly 225 side window 210 is left open until the leadwires are attached to the associated wire bond pads 212. In a preferred embodiment, a silicone or similar adhesive would be back-filled into the hole to prevent the ingress of body fluids and the like.

Figures 29A, 29B:
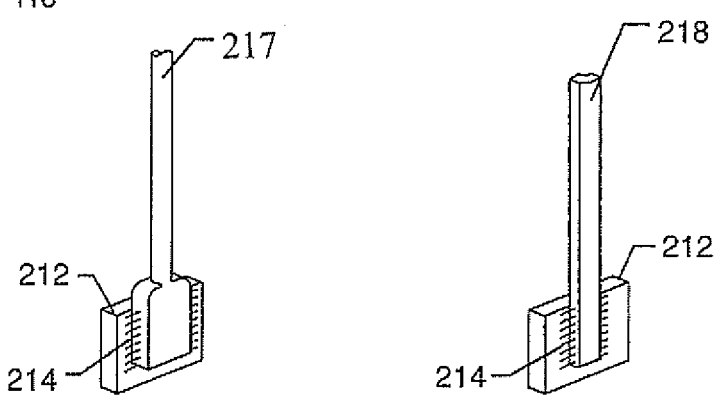
FIG. 29A is a perspective view of a paddle lead.
FIG. 29B is a perspective view of a ribbon lead.

FIG. 29a illustrates a paddle lead 217 electrically attached to header block wire bond pad 212 using electrical attachment material 214 as previously illustrated in FIG. 29.

FIG. 29b illustrates the rectangular or ribbon-shaped leadwire 218 electrical connection to header block connector assembly wire bond pad 212 using electrical attachment material 214 as previously illustrated as leadwire 218 in FIG. 29.

Figure 30:
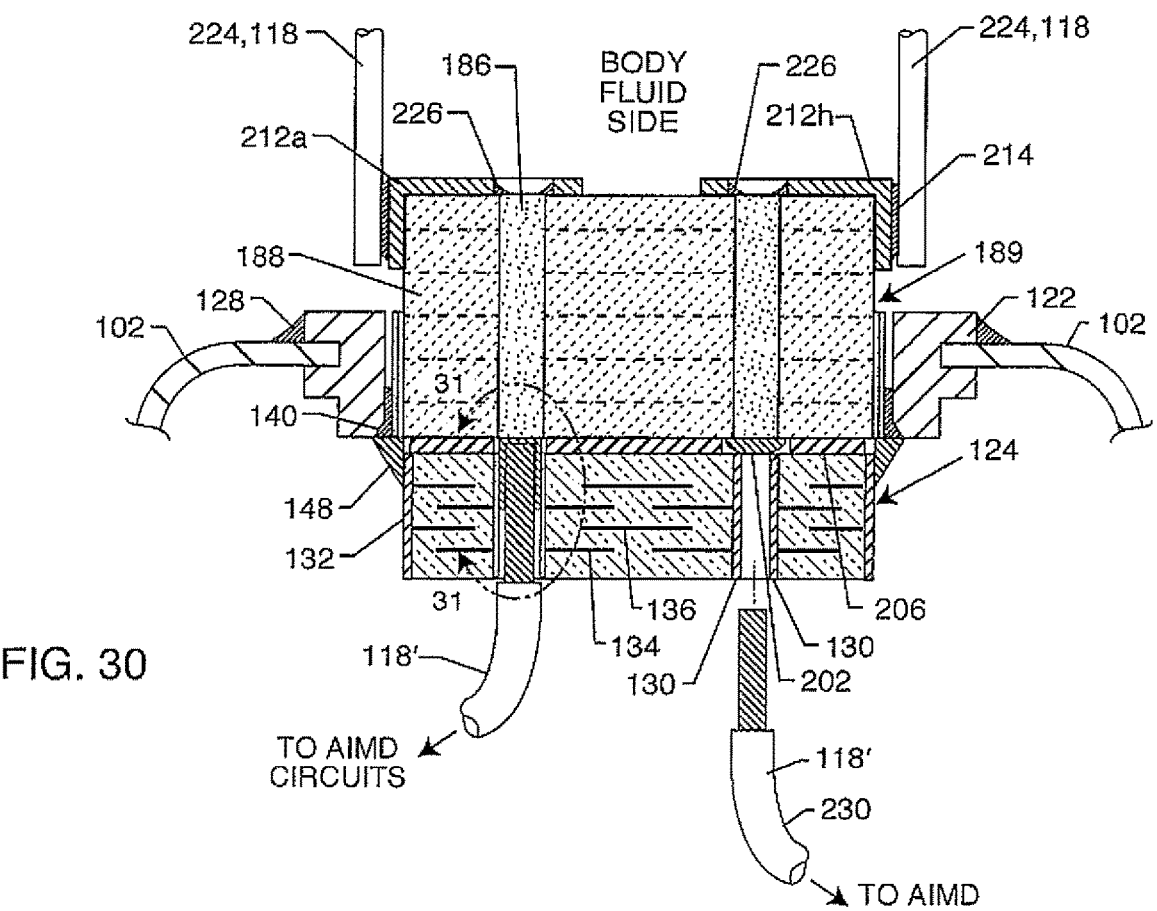
FIG. 30 is a sectional view taken from the structure of FIG. 29 along lines 30-30.
Figure 31:
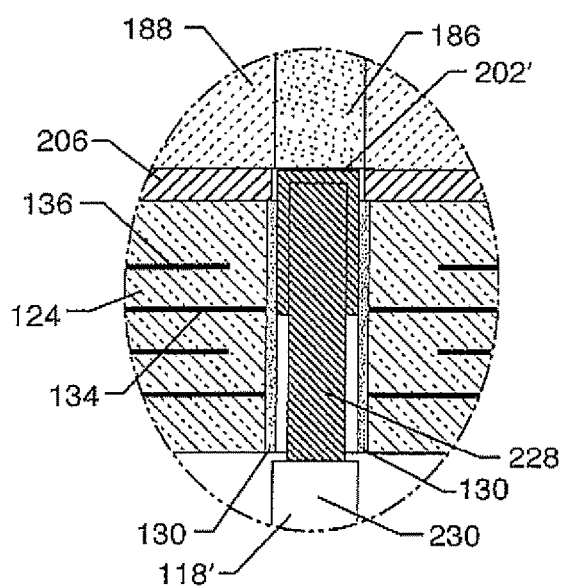
FIG. 31 is an enlarged view taken from FIG. 30 along lines 31-31.

FIG. 30 is taken generally from section 30-30 from FIG. 29 and shows the co-fired high purity alumina ($Al_2O_3$) hermetic terminal subassembly 189 with one or more pure platinum conductors 186 of the present invention in sectional view along with the BGA 202 mounted feedthrough capacitor 124. The L-shape wire bond pads 212 and their electrical attachment to the platinum conductor 186 has already been described as electrical connection material 226. FIG. 30 illustrates two novel internal leadwires 118' which are internal to the AIMD. On the right-hand side, the leadwire is shown not yet inserted into the hole of the feedthrough capacitor 124. A major advantage of this internal leadwire 118' is that it does not need to be non-toxic or biocompatible. The reason for this is that internal leadwires and circuits are inside the hermetically sealed AIMD housing 102 of the medical device 100. In a preferred embodiment, internal leadwires 118' would be either bare or insulated 230 copper leadwire. As shown in FIG. 30, a portion of the insulation 230 has been removed. Again, in a preferred embodiment, the exposed tip 228 of the leadwire would either be tinned, or solder dipped. This is better understood by referring to FIG. 31, which is a blow-up view taken from section 31-31 of FIG. 30. Shown is an internal leadwire 118' with insulation 230. It also shows the bare and solder-coated exposed tip 228. When the entire assembly is heated such that the BGA 202 is reflowed, the solder comprising the BGA 202 flows not only to the platinum conductor 186, but also reflows with the solder coating on the exposed tip 228 of leadwire 118' thereby completing an electrical circuit. This has a major advantage over all of the prior art, in that, the expensive platinum iridium or equivalent leadwire has been completely eliminated and replaced by a very inexpensive internal leadwire 118'.

Figure 32:
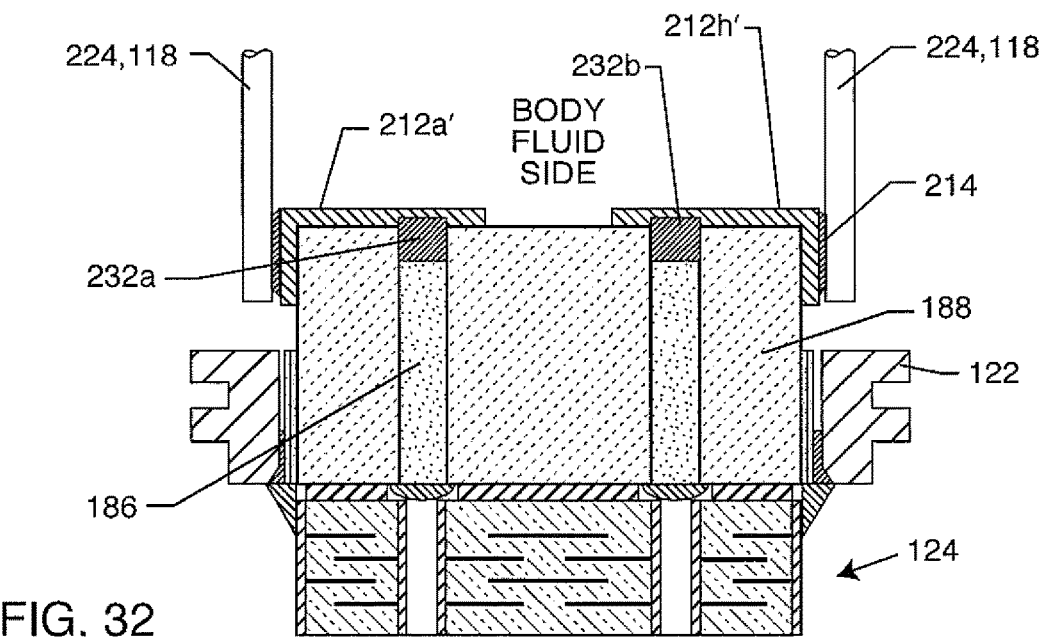
FIG. 32 is a sectional view of another exemplary embodiment similar to FIG. 30 now showing a gold braze perform connecting the side mounted wire bond pad and the platinum fill.

FIG. 32 is similar to FIG. 30 except that, in this case, the L-shape wire bond pads 212a' and 212h' no longer have a hole in the top. In other words, there is no place for electrical connection material 226. Instead, there is a gold braze or equivalent 232a which is captured underneath the wire bond pad 212 and is disposed adjacent the platinum conductor 186 of the co-fired high purity alumina ($Al_2O_3$) hermetic terminal subassembly.

Figure 33:
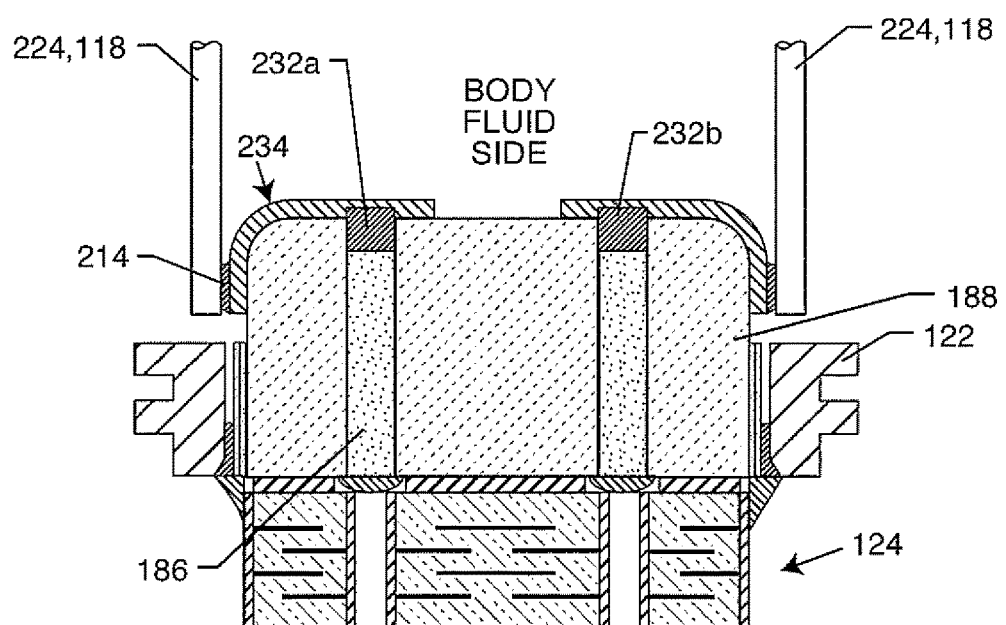
FIG. 33 is a sectional view similar to FIG. 32 now showing a curved radius insulator.

FIG. 33 is similar to FIGS. 30 and 32 except that a radius 234 has been added to the corner of the co-fired high purity alumina ($Al_2O_3$) hermetic terminal subassembly with one or more pure platinum conductors 186. This radius corner is important to eliminate stress risers which could lead to fracturing in the corner during laser weld of the electrical attachment material 214 of leadwires 224, 118.

Figure 34:
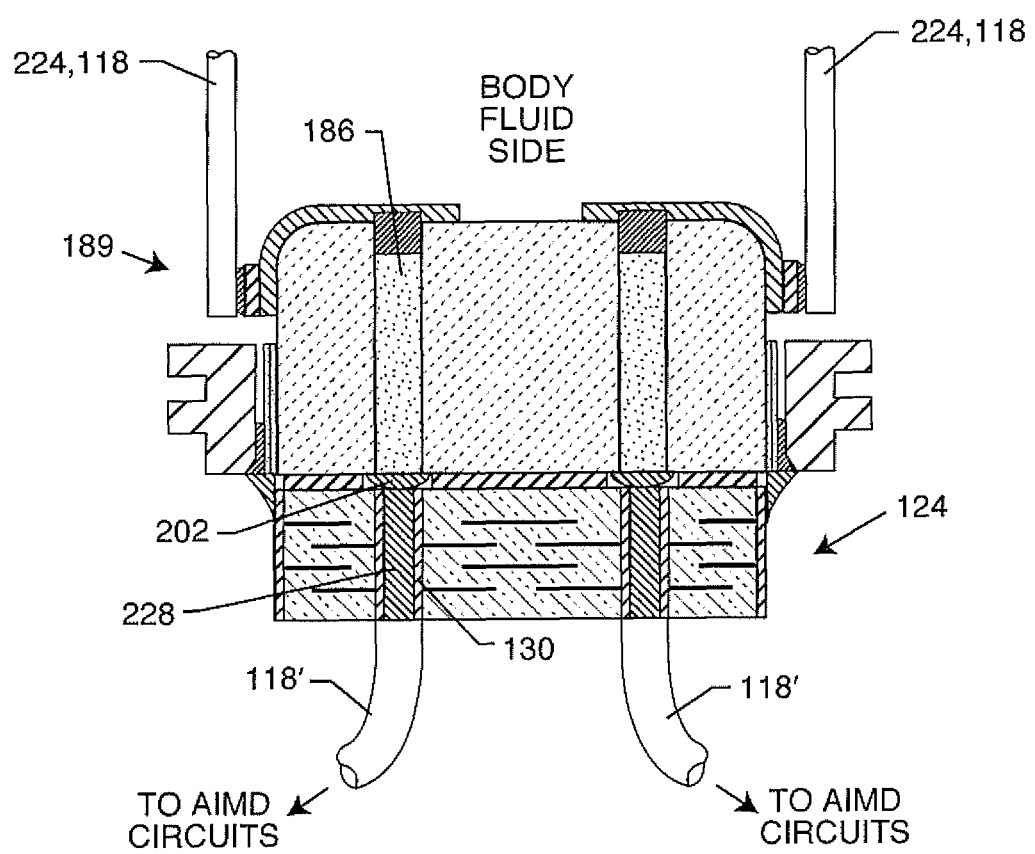
FIG. 34 is a sectional view similar to FIG. 33 now showing a three-way connection between the internal AIMD leadwires, the capacitor active plates through the bore-coated metallization and the platinum fill of the insulator.

FIG. 34 is similar to FIG. 32 and simply illustrates that in any of the embodiments described herein, internal leadwires 118' are part of a solder reflow process wherein, an attachment is made from the platinum conductor 186, to the active electrode plates of the feedthrough capacitor 124 and in turn, to the internal leadwires 118'. In other words, the BGA 202 accomplishes three very important functions. During high temperature reflow of the solder comprising the BGA 202, a connection is made between the platinum conductor 186, the internal metallization 130, and to the exposed tip 228 of the leadwire 118'.

Figure 35:
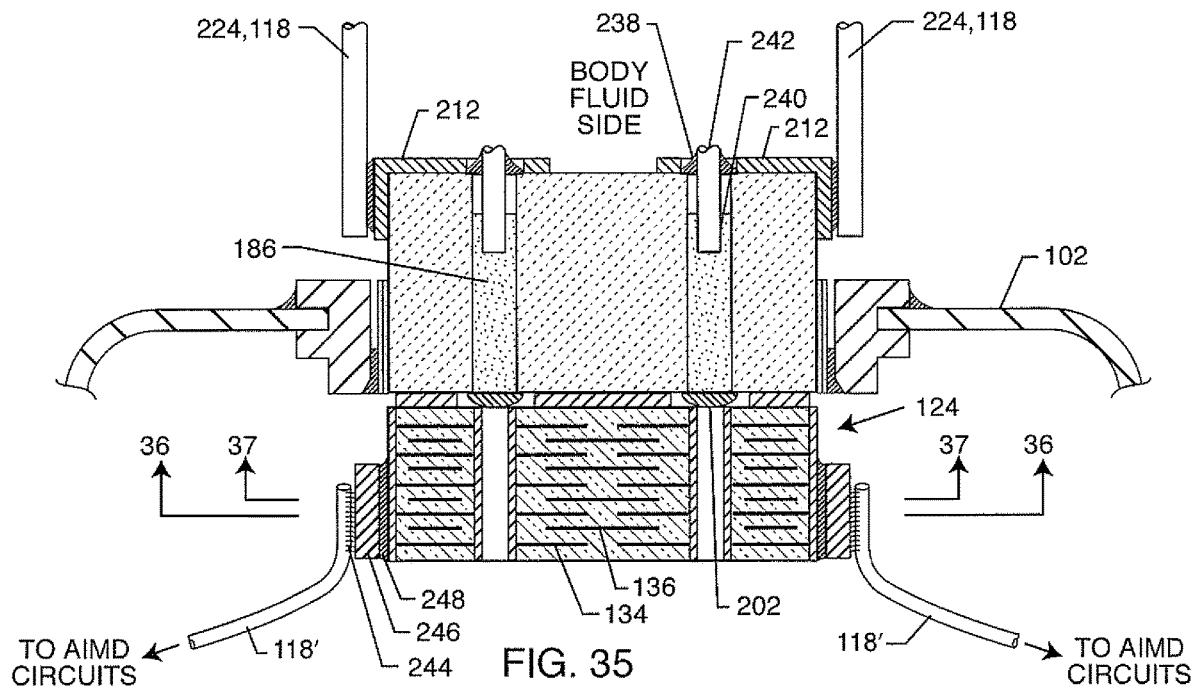
FIG. 35 is a sectional view similar to FIG. 30 now showing another exemplary embodiment of the present invention.
Figure 36:
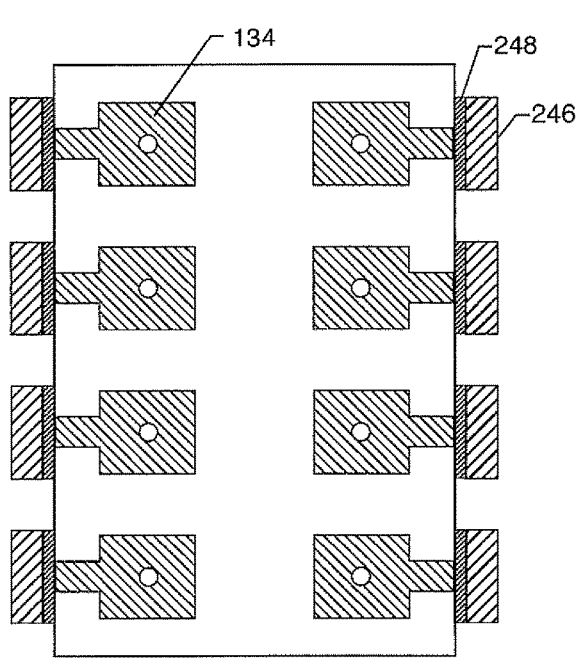
FIG. 36 is a sectional view taken from FIG. 35 along lines 36-36 now showing the active plates.
Figure 37:
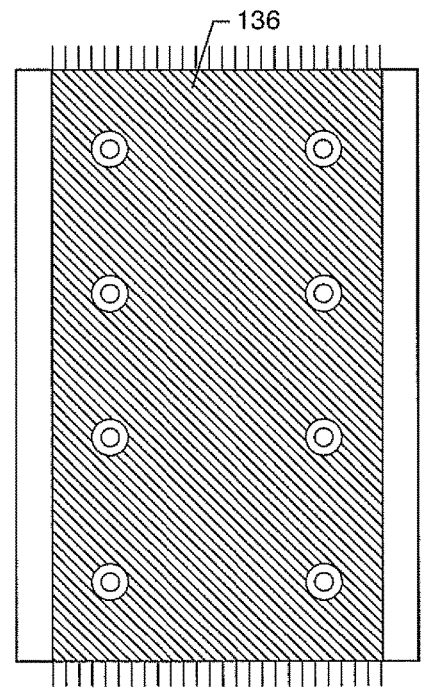
FIG. 37 is a sectional view taken from FIG. 35 along lines 37-37 now showing the ground plates.

FIG. 35 is similar to FIG. 30. There is a difference in the L-shaped wire bond pad 212. In this case, there is a hole in the wire bond cap through which a pin 242 is either laser welded, brazed or the like 238 to the L-shaped wire bond pad 212. This pin ideally would be of platinum or similar compatible metal. This assembly is co-fired along with the pure platinum conductor 186 so that a solid mechanical and electrical connection is made between the pin 240 and the platinum conductor 186. There is also a difference in the way that the internal leadwires 118' are attached to the feedthrough capacitor 124. This is a special feedthrough capacitor that is rectangular in shape. The rectangular shape is better understood by looking at the cross-sectional views shown in FIGS. 36 and 37. FIG. 36 is taken generally along section 36-36 of FIG. 35. FIG. 37 is generally taken from section 37-37 of FIG. 35. The view in FIG. 35, therefore, is the end view of a rectangular structure. The active electrode plates 134 are brought out to the sides of the capacitor, which is better illustrated in FIG. 36. This allows wire bond pads 246 to be attached to the capacitor. Attachment is done by thermal-setting conductive adhesives, gold braze, high temperature solders, or the like 248. The capacitor ground plates 136 is terminated at its ends. This is important so that the ground electrode plates 136 do not short to the active electrode plates 134. This makes subsequent attachment of internal leadwires 118' very easy. Internal leadwires 118' can be attached to the wire bond pads 246 by thermal sonic bonding, resistance bonding, resistance welding, soldering, thermal-setting conductive adhesives, brazes, or the like, 244.

Figure 38:
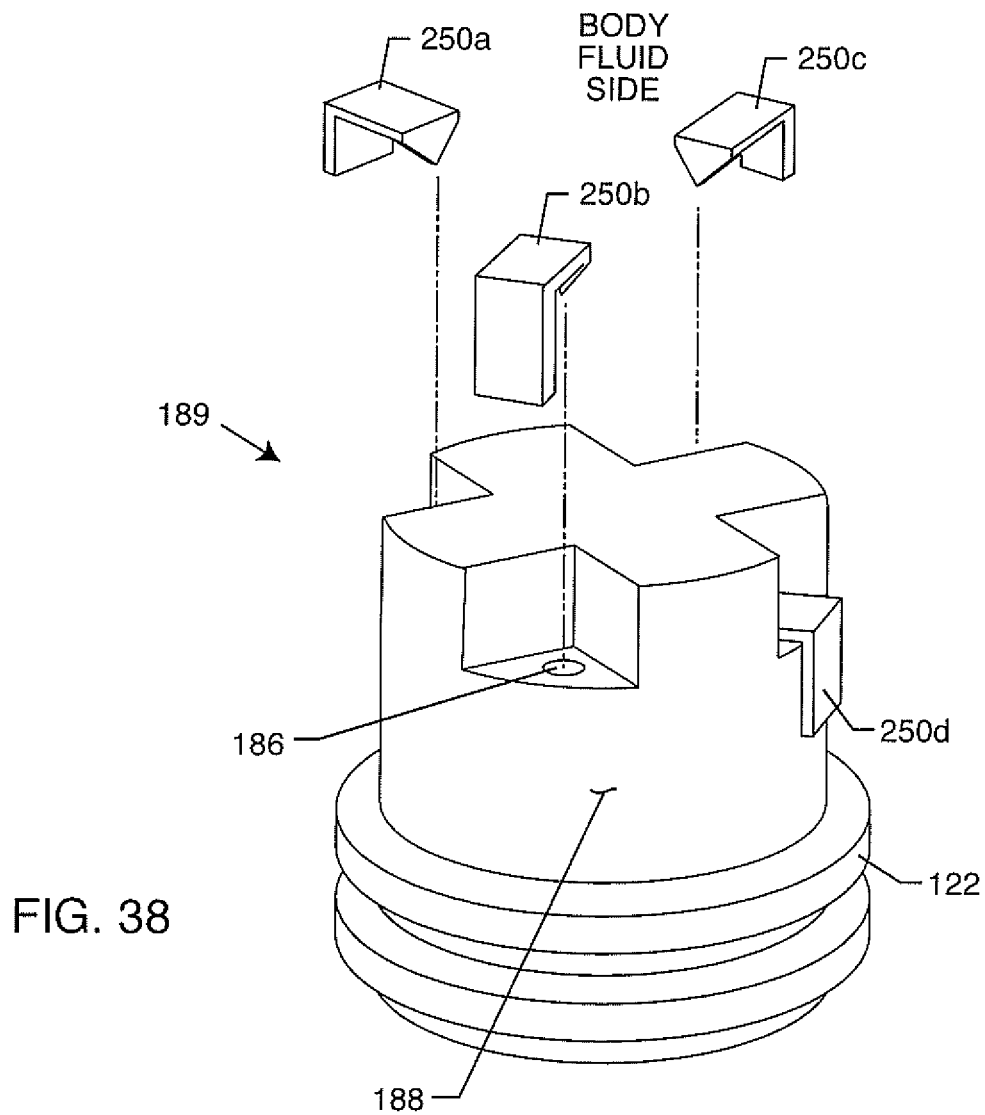
FIG. 38 is a perspective view of an exemplary embodiment of a round quad polar hermetic terminal assembly.
Figure 39:
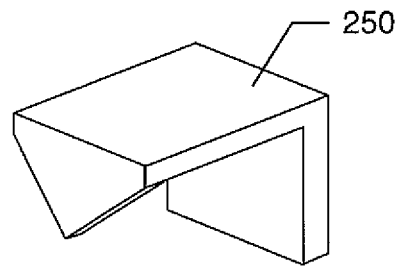
FIG. 39 is a perspective view of an exemplary wire bond pad.
Figure 40:
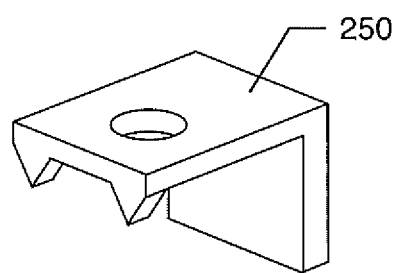
FIG. 40 is a perspective view of another exemplary wire bond pad.
Figure 41:
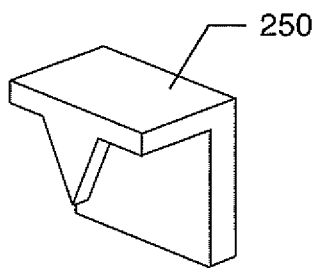
FIG. 41 is a perspective view of another exemplary wire bond pad.
Figure 42:
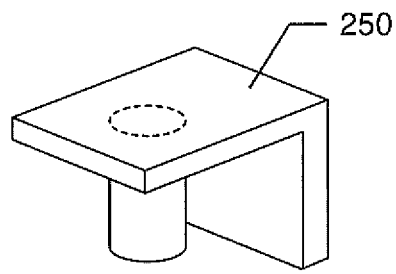
FIG. 42 is a perspective view of another exemplary wire bond pad.

FIG. 38 illustrates a round quad polar co-fired high purity alumina ($Al_2O_3$) hermetic terminal subassembly with one or more pure platinum conductors 186 of the present invention. Shown are novel L-shaped wire bond pads 250a through 250d, which can be co-fired with the pure platinum conductors 186 in the via holes. Since these wire bond pads 250 are on the body fluid side, it is important that they be non-toxic and biocompatible. Ideally, they would be of platinum or similar metal that was readily co-fired and matched to the CTE of the solid platinum conductor 186.

FIGS. 39 through 42 illustrate alternative shapes for the wire bond pads 250A through 250D previously illustrated in FIG. 38. Each wire bond pad has one or more respective downwardly extending extrusions 250A' to 250D' in order to penetrate the paste comprising the platinum conductor 186 so that when co-firing, a solid mechanical and electrical connection is made.

Figure 43:
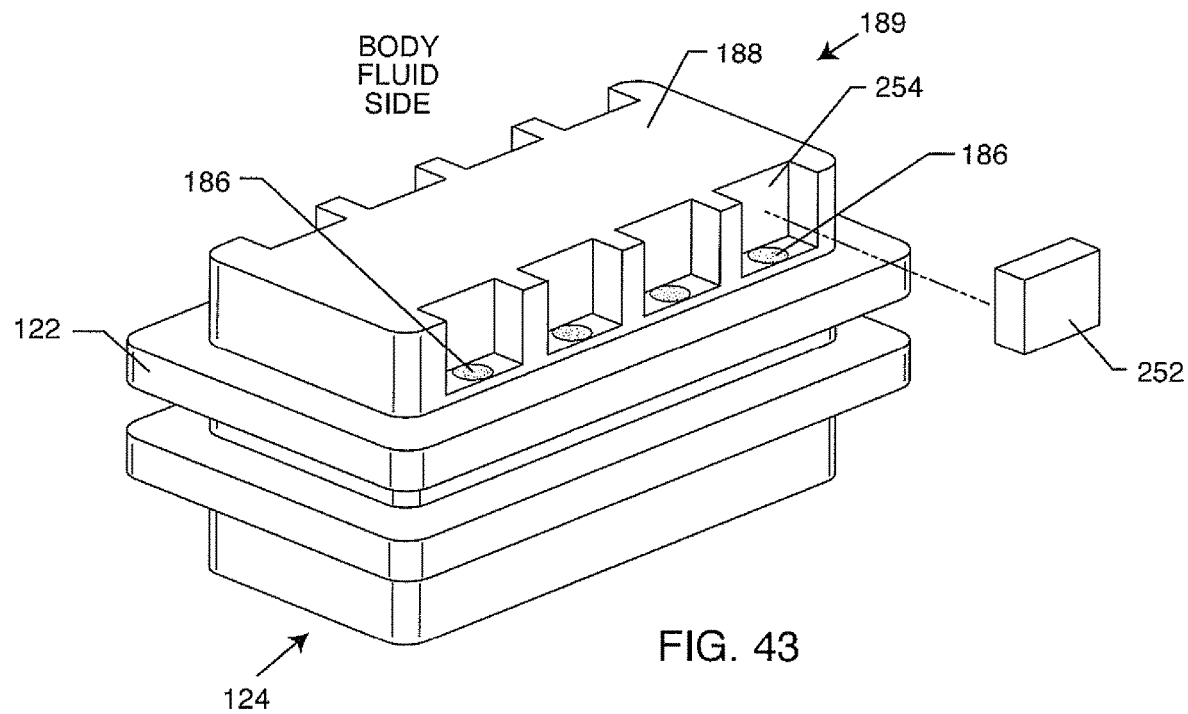
FIG. 43 is a perspective view of an exemplary embodiment of a hermetic terminal subassembly now showing castellations formed in the insulator configured to receive wire bond pads.

FIG. 43 illustrates the co-fired high purity alumina ($Al_2O_3$) hermetic terminal subassembly 189 with one or more pure platinum conductors 186 of the present invention wherein, the alumina substrate 188 protrudes towards the body fluid side well above the ferrule 122. There are castellations 254 formed into the side of the alumina substrate 188 to conveniently hold and register wire bond pads 252. The wire bond pad 252 can have a pin or extrusion 250A' to 250D' as shown in FIGS. 39 to 42 coming out the bottom wherein, the extrusion would be co-fired with the platinum conductor 186. In the embodiment illustrated in FIG. 43, the wire bond pad 252 would be gold brazed with a gold braze pre-form (not shown) to make a solid mechanical and electrical contact between the bottom of the wire bond pad 252 and the platinum conductor 186.

Figure 44:
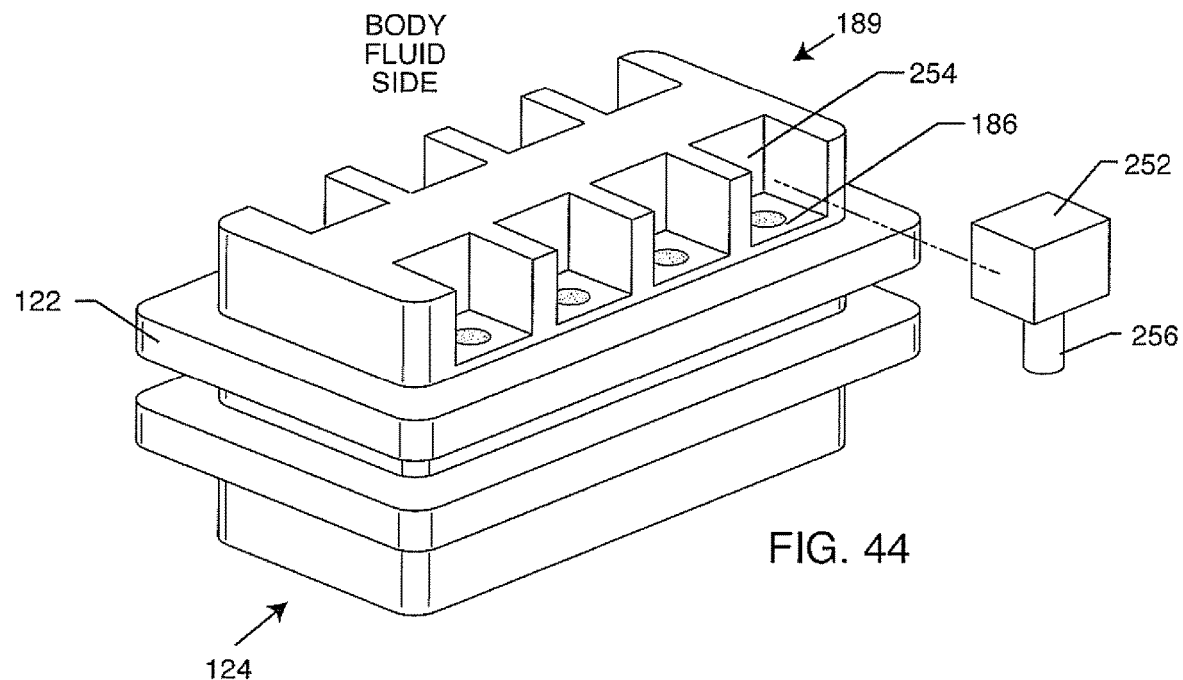
FIG. 44 is a perspective view of another exemplary embodiment of a hermetic terminal subassembly similar to FIG. 43 now showing deeper castellations.

FIG. 44 is nearly identical to FIG. 43 except that the castellations 254 have been made larger (into a square shape) and the corresponding wire bond pad 252 has also been made square. This structure would be much more robust during compressing welding operations during attachment of leadwires 118 where substantial force is pressed against the wire bond pad. Referring once again to FIG. 44, one can see that the wire bond pads 252 have a co-machined or co-formed post 256. This post would slip down into the paste comprising the platinum conductor 186 and be co-fired. An ideal material for CTE match would, therefore, be a platinum post; however, gold, titanium, tantalum, palladium can all be used.

Figure 45:
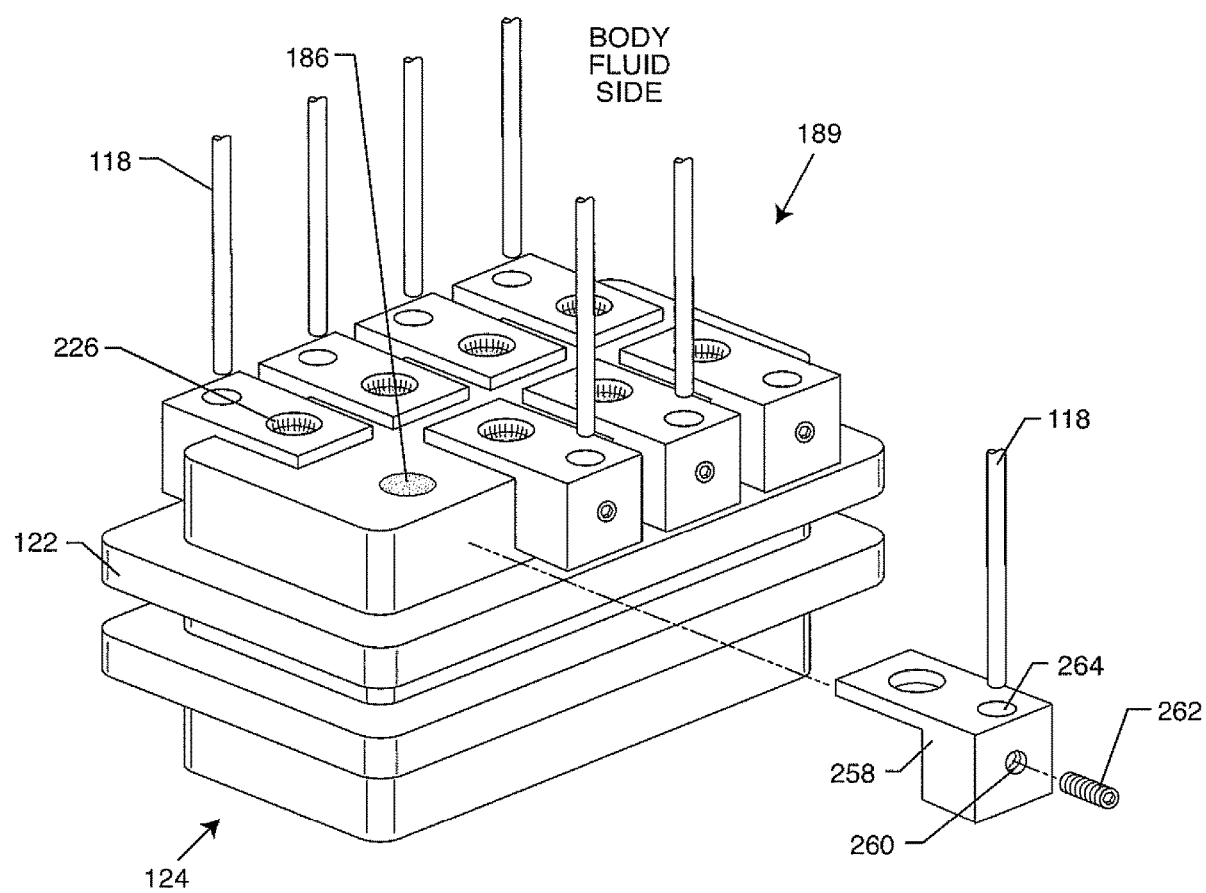
FIG. 45 is a perspective view of another exemplary embodiment of a hermetic terminal subassembly now showing leadwire holes and set screws.

FIG. 45 is similar to FIGS. 43 and 44 except that the L-shaped wire bond pad 258 has a threaded hole 260. There is a hole 264 to receive leadwires 118 coming from the header block connector assembly. A set screw 262, which may have an Allen head or the like, is used to firmly secure the leadwire 118 into the hole 264 in the wire bond pad hole. The L-shaped wire bond pad 258 is attached to the platinum conductors 186 by means of electrical connection material 226, which has been previously described.

Figure 46:
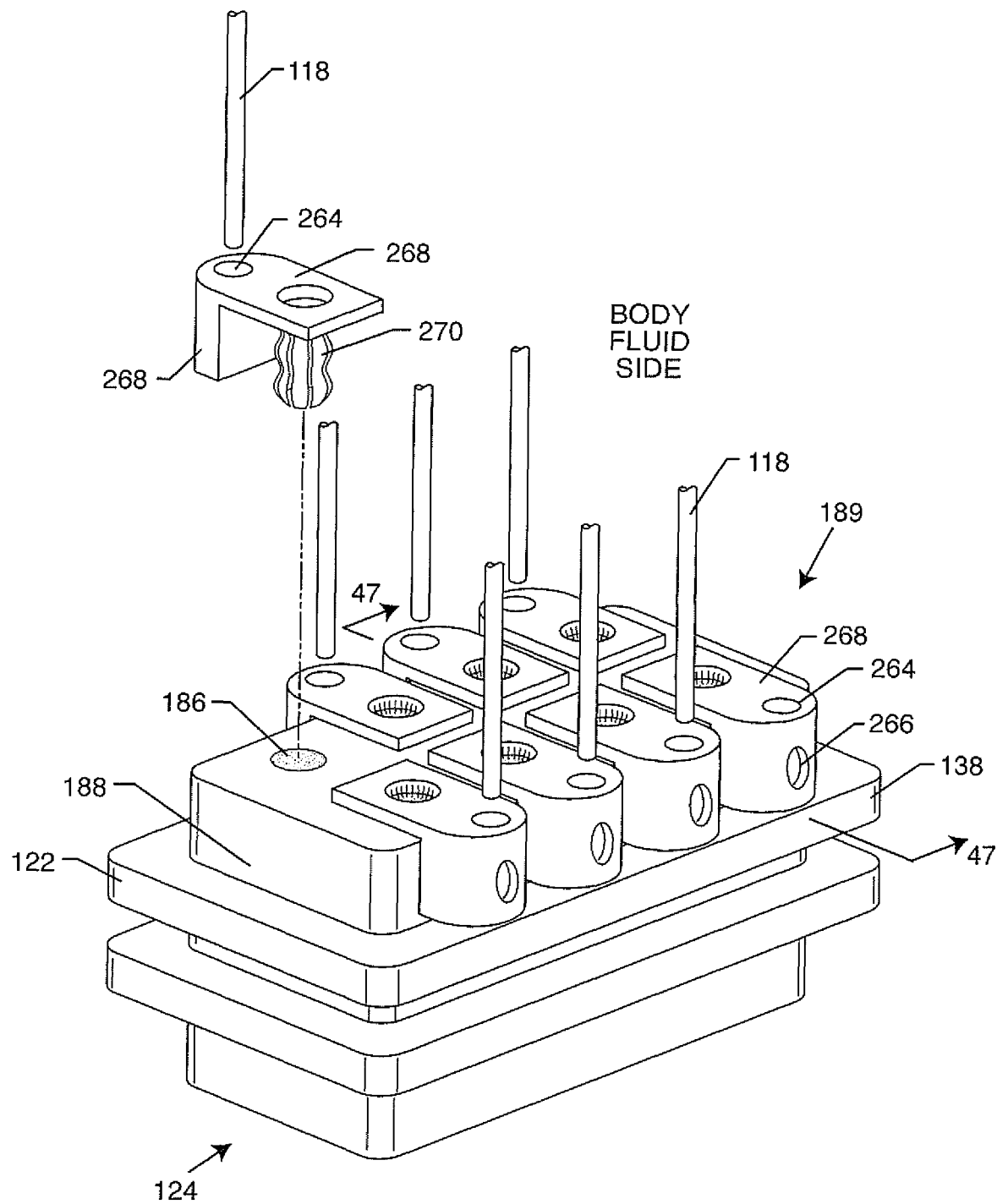
FIG. 46 is a perspective view of another exemplary embodiment of a hermetic terminal subassembly now showing an insertable contact spring.

FIG. 46 illustrates a different type of header block connector assembly 268 which has an insertable contact spring 270. This allows the co-fired high purity alumina ($Al_2O_3$) hermetic terminal subassembly 189 with one or more pure platinum conductors 186 of the present invention to be formed and then the header block connector assemblies to be attached by simple mechanical force insertion. This is best understood by referring to FIGS. 47 and 48, which are sectional views taken from FIG. 46. One can see that the insertable contact spring 270 has been inserted about half way down into the via hole. The bottom of the via hole is co-fired pure platinum in accordance with the present invention and forms a hermetic terminal subassembly 189 (FIG. 49).

Figure 47:
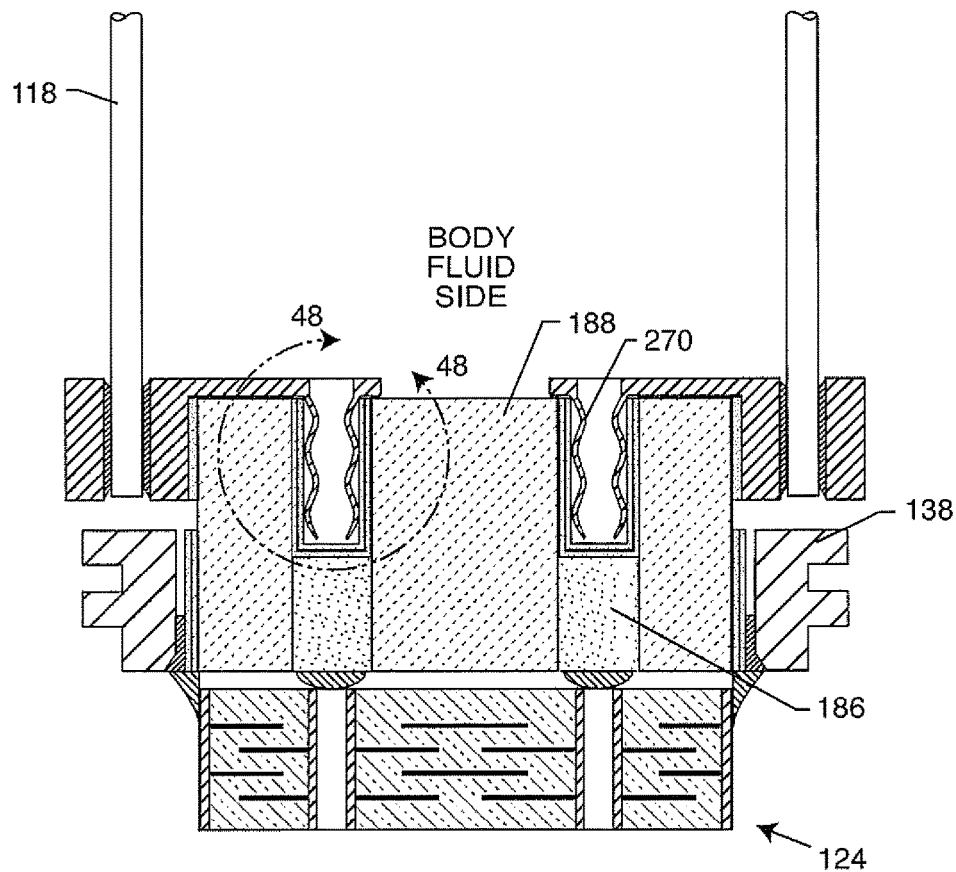
FIG. 47 is a sectional view of the structure of FIG. 46 taken along lines 47-47.
Figure 48:
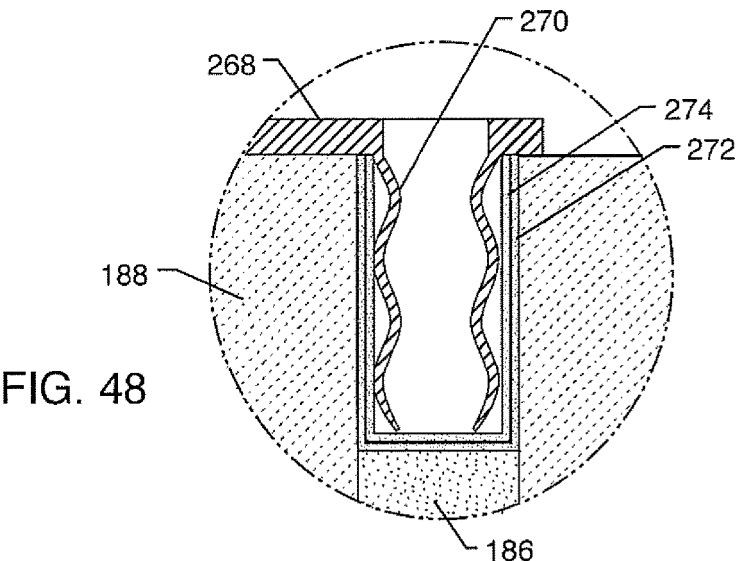
FIG. 48 is an enlarged view of the structure of FIG. 47 taken along lines 48-48.

FIG. 48 is a sectional view 48-48 taken from FIG. 47 and illustrates the insertable contact spring 270 inserted into the bore hole. Importantly, the bore hole is first metallized with an adhesion layer 272 and a wetting layer 274. These layers could be actually merged into a single layer in the case where gold or platinum was sputtered on. Or, an adhesion layer of titanium could be used with a niobium or molybdenum layer 274 sputtered on top. In a preferred embodiment, the insertable contact spring 270 would be of Nitinol alloy. At relatively cold temperature, the insertable (Nitinol) contact spring 270 would shrink down and contract. This memory shaped alloy would be designed in this application to expand rapidly at room temperature and, therefore, mechanically fit very securely into the via hole. This would, of course, be true both at room temperature 25° C. and at body temperature 37° C. As it turns out, the entire assembly is easily reworkable. All one would have to do is chill it down, say to around freezing temperature, and then literally all the Nitinol leadwires would contract and insertable contact spring 270 could easily be pulled out. Leadwire 118 coming from the header block connector assembly (not shown) could either be laser welded to the end of a connector block or, as is shown in FIG. 46, could be slipped into a hole 264. There is a side hole 266 wherein a laser weld could be performed to make a secure electrical and mechanical attachment between the leadwire 118 and the header block connector assembly 268.

Figure 49:
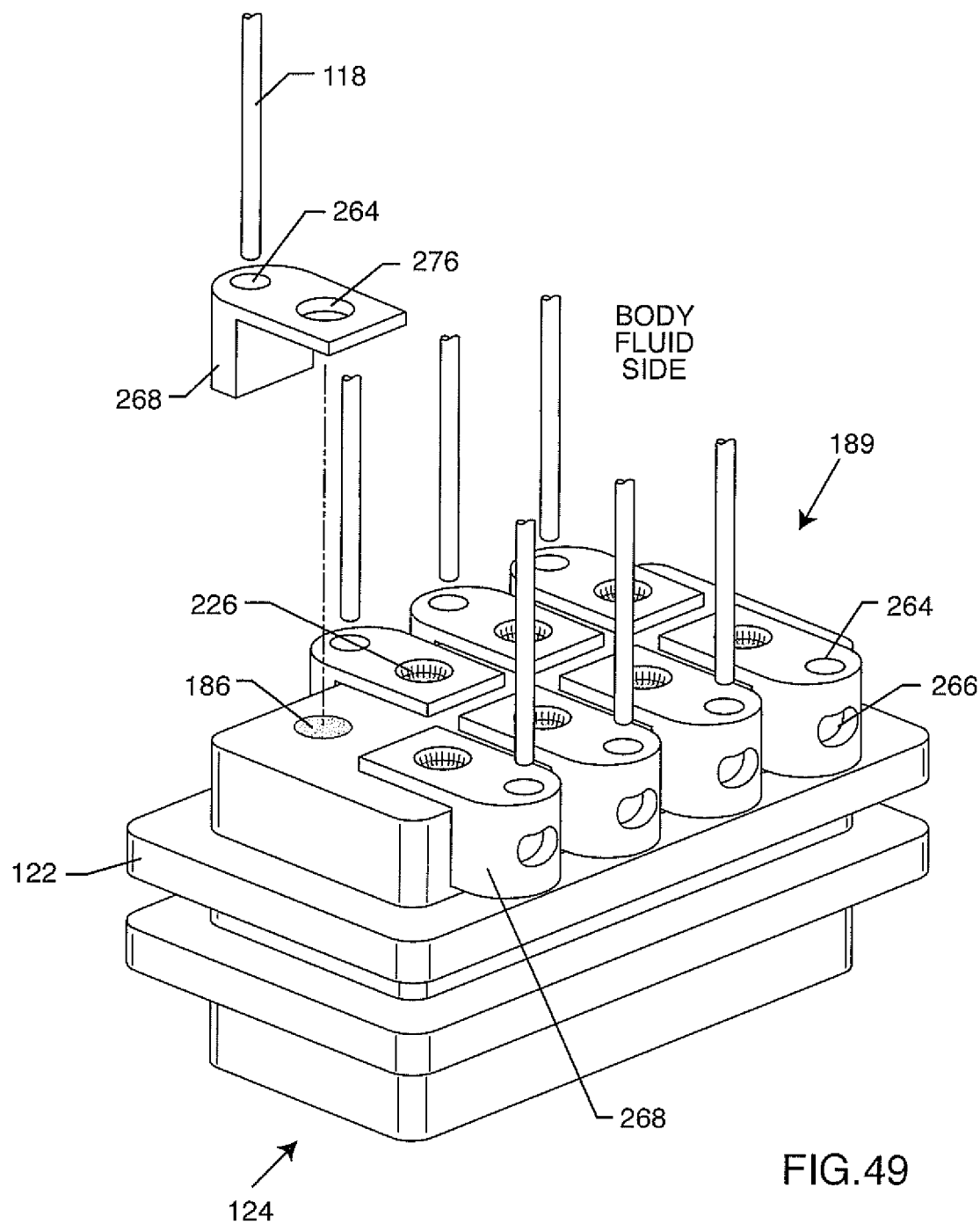
FIG. 49 is a perspective view of another exemplary embodiment of a hermetic terminal subassembly now showing laser weld access holes.

FIG. 49 is the same as a combination of the co-fired high purity alumina ($Al_2O_3$) hermetic terminal subassembly 189 with one or more pure platinum conductors 186 previously described in FIG. 30 and FIG. 46. In this case, the wire connector blocks 268 have a hole 264, as previously described in FIG. 46, for convenient reception of leadwire 118 from the header block connector assembly (not shown). The header block connector assembly 268 has a hole 276 which is designed to be aligned directly over the platinum conductors 186. An electrical connection material 226 is then made either by gold brazing, thermal-setting conductive adhesives, or the like. A side hole 266 is used to laser weld the terminal pin or leadwire 118 to the inside of the header block connector assembly 268 hole 264.

Figure 50:
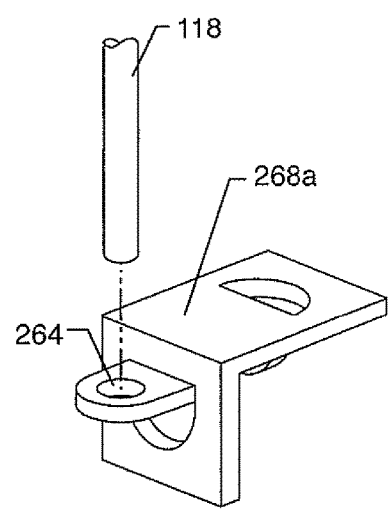
FIG. 50 is a perspective view of an embodiment of a wire bond pad.
Figure 50A:
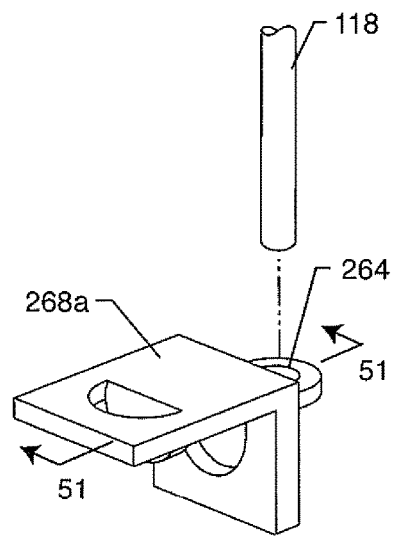
FIG. 50A is a perspective view of an embodiment of wire bond pad similar to FIG. 50.

FIGS. 50 through 56 show alternative embodiments of the header block connector assemblies such as those previously illustrated in FIGS. 46 and 49. FIGS. 50 and 50A illustrate stampings, which are ideally of platinum or some other similar biocompatible material. They have a hole for convenient reception of leadwire 118 which may then be permanently attached by laser welding.

Figure 51:
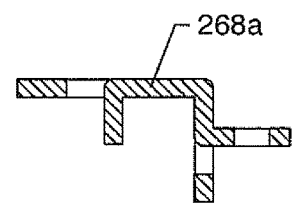
FIG. 51 is a sectional view of the structure of FIG. 50A taken along lines 51-51.

FIG. 51 is a sectional view 51-51 taken from FIG. 50A showing the stamping and cross-section.

Figure 52:
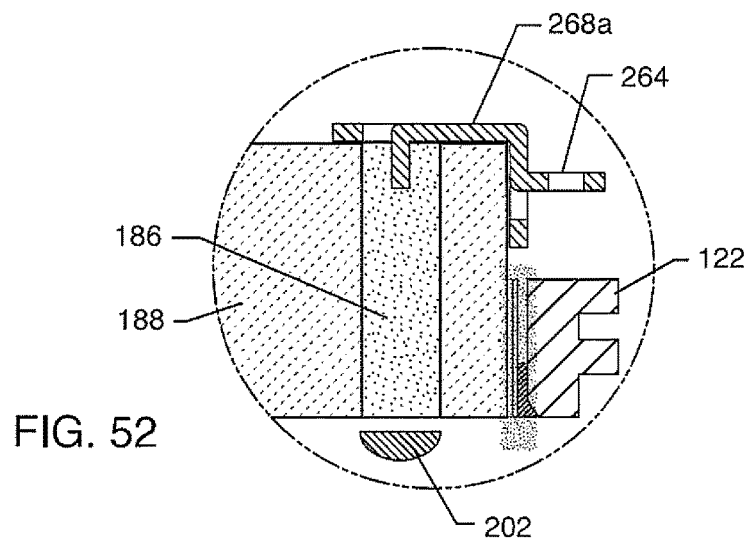
FIG. 52 is an enlarged sectional view of the wire bond pad of FIGS. 50A and 51 co-fired into the platinum filled via.

FIG. 52 is a sectional view showing the stamping of FIGS. 50, 50A and 51 co-fired into the novel platinum conductor 186 of the present invention.

FIGS. 53 and 53A illustrate another embodiment of stamped header block connector assembly 268b now with fingers 265 that capture the leadwire 118.

FIG. 54 is an alternative embodiment for the header block connector assembly 268c, which in this case, has a leadwire 278. The leadwire may be attached to the header block connector assembly 268c by laser welding or the entire assembly could be co-machined or even formed by metal injection processes. In this case, the leadwire is a platinum or suitable biocompatible material that has a CTE that will match that of the platinum conductor 186. In this case, the leadwire 278 is co-fired with the platinum conductor 186 to form a solid electrical and mechanical joint.

Figure 55:
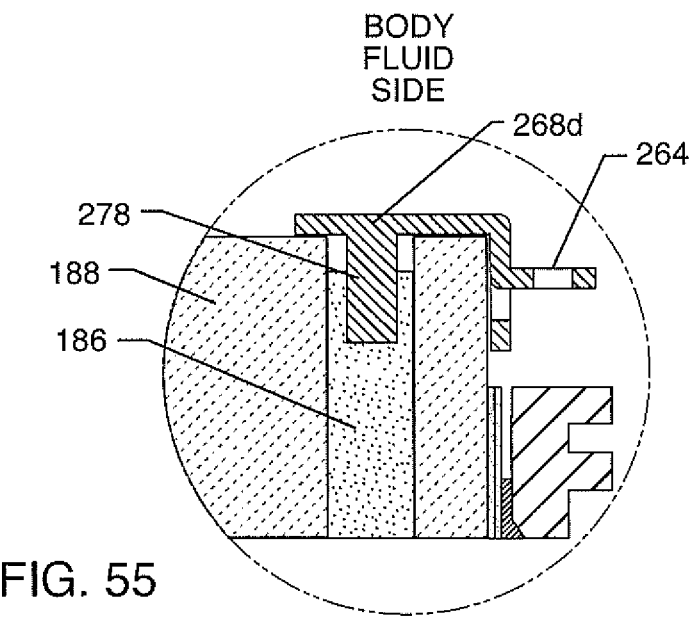
FIG. 55 is an enlarged sectional view of another embodiment of a wire bond pad similar to FIG. 55 now showing a hole to capture the leadwire.

FIG. 55 is similar to FIG. 54 except that the header block connector assembly 268d has a hole 264 for insertion of the leadwire 118 (not shown) where it can be laser welded.

Figure 56:
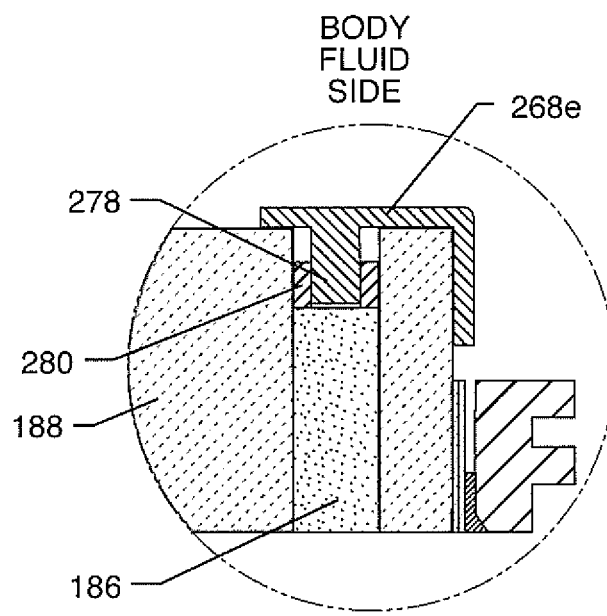
FIG. 56 is an enlarged sectional view of another embodiment of a wire bond pad similar to FIGS. 55 and 56 now showing a gold braze.

FIG. 56 is similar to FIG. 54 except that the header block connector assembly 268e shows where the leadwire 278 has been gold brazed 280 to the via hole pure platinum conductor 186.

Figure 57:
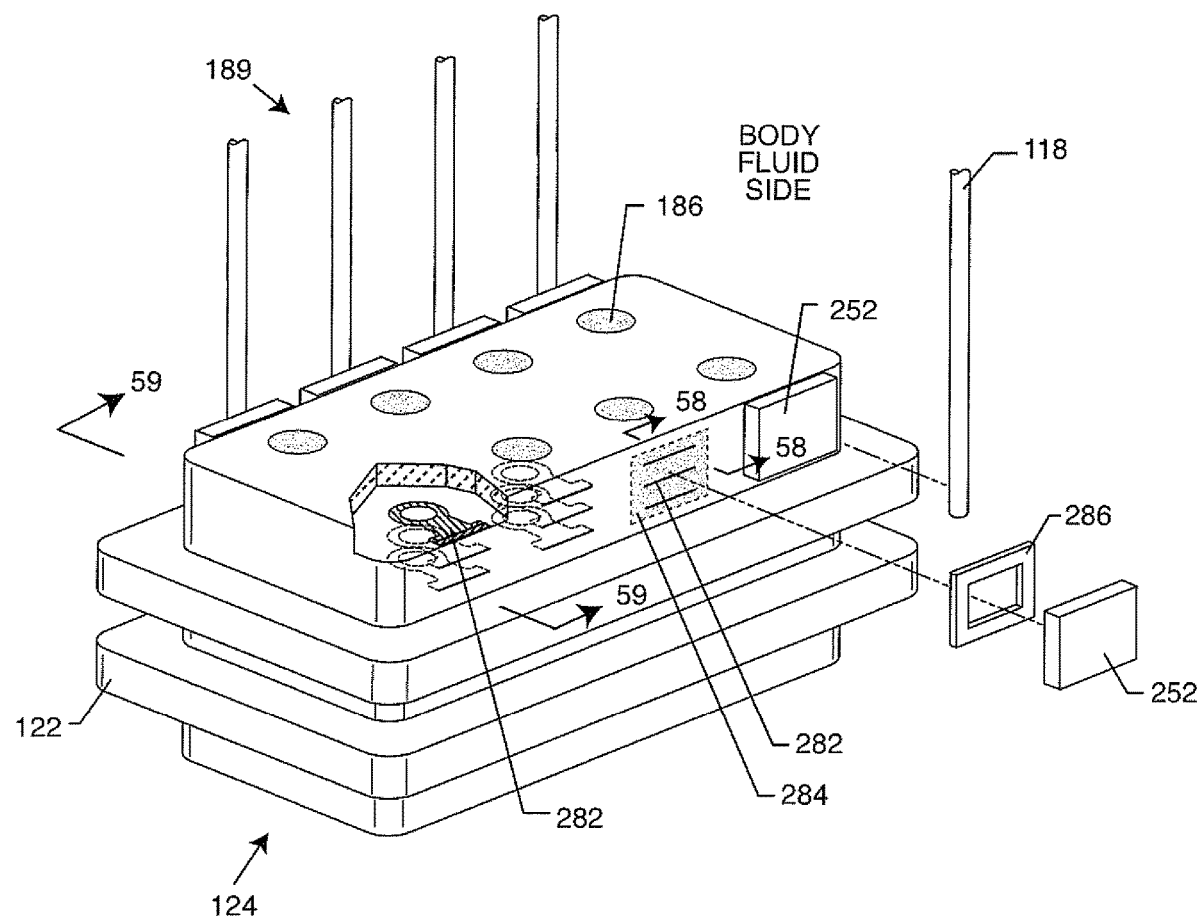
FIG. 57 is a perspective view of another embodiment of a hermetic terminal subassembly with internal circuit traces.

FIG. 57 illustrates a co-fired high purity alumina ($Al_2O_3$) hermetic terminal subassembly 189 with one or more pure platinum conductors 186 with brazed wire bond pads 252. There are internal circuit traces 282 which are exposed on edge where each of the wire bond pads 252 of the header block connector assemblies are to be attached. There is a metallization added 284 such as a gold or a platinum sputtering over a titanium bonding layer. When the metallization 284 is on the device side (not shown), those skilled in the art could use a variety of materials beyond gold and platinum. There is a gold braze pre-form 286 that is disposed between the wire bond pad 252 of the header block connector assembly and the metallization 284.

Figure 58:
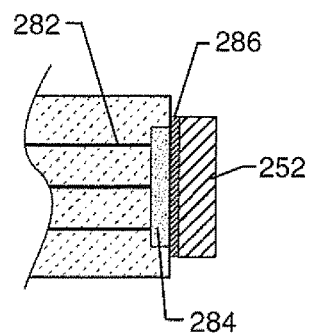
FIG. 58 is an enlarged sectional view taken from FIG. 57 along lines 58-58 showing the internal circuit traces.

FIG. 58 is a sectional view taken from section 58-58 of FIG. 57 illustrating the gold braze pre-form 286 after it has been melted at high temperature to make a solid electrical and mechanical connection between the wire bond pad 252 of the header block connector assembly and the metallization 284. The metallization 284 desirably connects the internal circuit traces 282 in parallel. In another embodiment (not shown) it is possible to use a dispensable gold paste in lieu of the gold braze pre-form to act as a sort of "mortar" to bind components.

Figure 59:
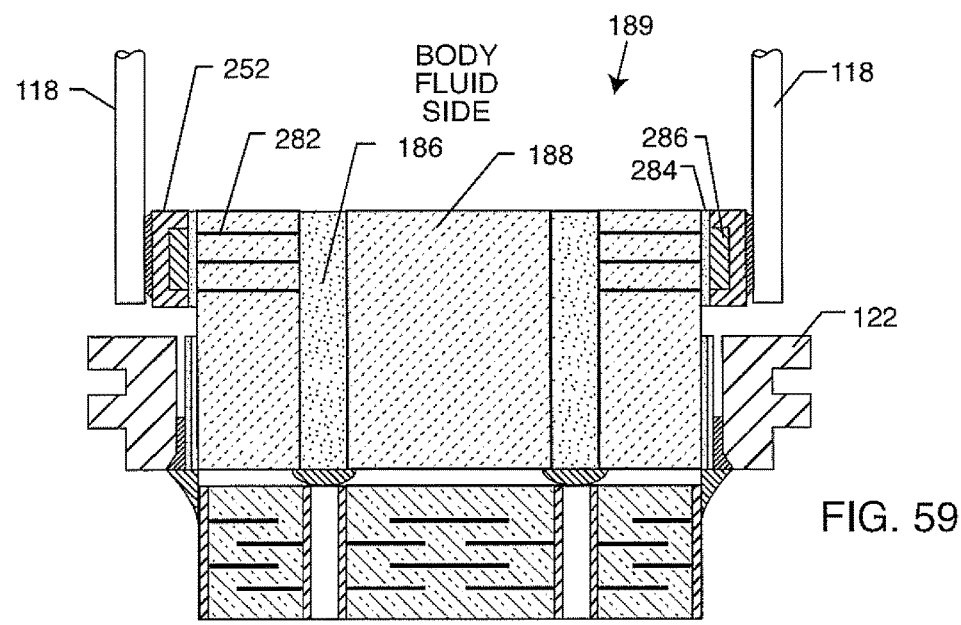
FIG. 59 is a sectional view taken from FIG. 57 along lines 59-59.

FIG. 59 is taken from section 59-59 of FIG. 57 and illustrates an alternative form of the wire bond pad 252 of the header block connector assembly. In this case, the header block connector assembly has been hollowed out, that is, a void or opening was made in the header block connector assembly to hold a gold braze pre-form 286 for attachment, at high temperature, to metallization 284.

Figure 60:
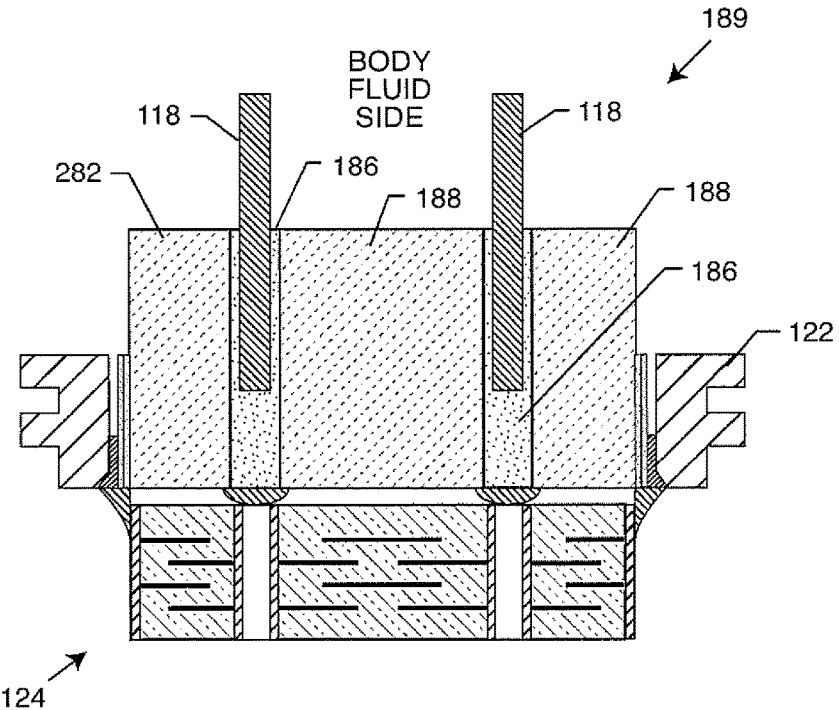
FIG. 60 is a sectional view of another exemplary embodiment of a hermetic terminal subassembly now showing a solid wire co-fired into the platinum filled via.

FIG. 60 illustrates a co-fired high purity alumina ($Al_2O_3$) hermetic terminal subassembly 189 with one or more pure platinum conductors 186 of the present invention wherein, leadwires 118 have been co-fired into the platinum conductors 186. In other words, the leadwires 118 are co-fired with the alumina substrate 188 and with the platinum conductors 186, all in one single operation. Leadwires 118 would be routed and connected to implantable lead conductors or header block connector assemblies, as is well known in the prior art. As an alternative to a platinum leadwire 118, the leadwires 118 may comprise iridium, rhodium, niobium if a reducing atmosphere is used or palladium in air if the sintering temperature is low enough.

Figure 61:
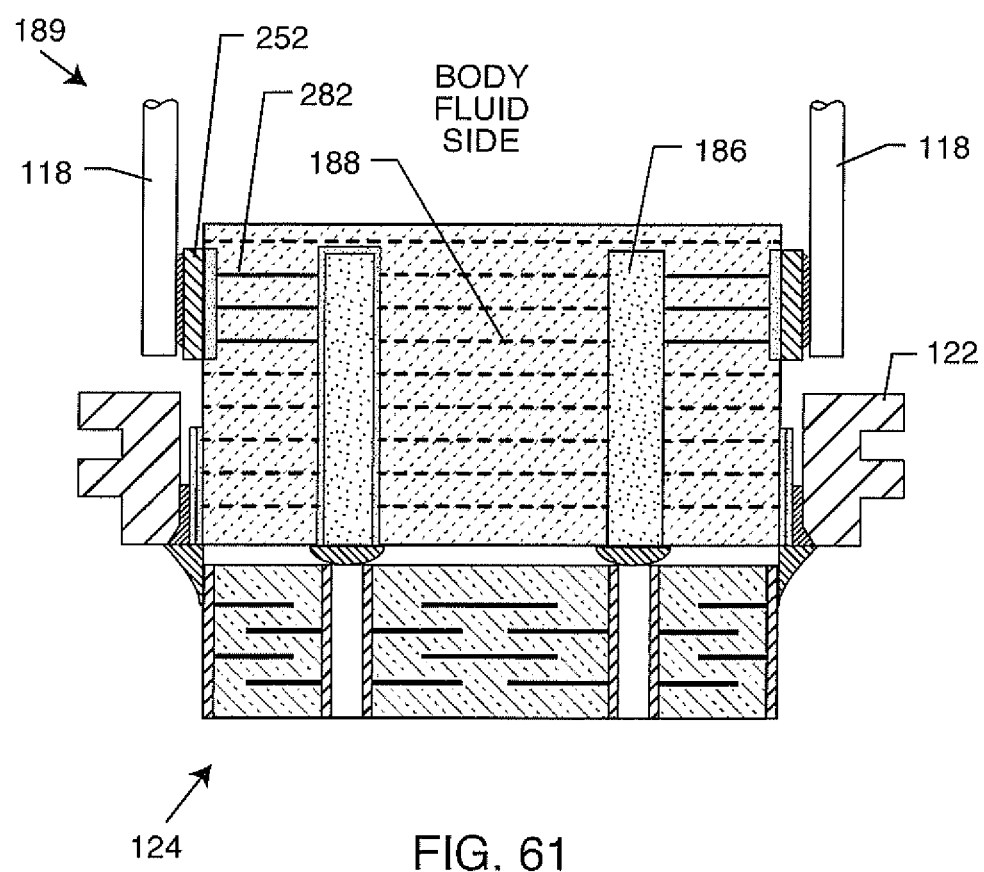
FIG. 61 is a sectional view of an embodiment of a filled via with internal circuit traces.

FIG. 61 illustrates an alternative embodiment for the co-fired high purity alumina ($Al_2O_3$) hermetic terminal subassembly 189 with one or more pure platinum conductors 186 of the present invention. In this case, there are internal circuit traces 282. The alumina substrate 188 then is laid down in tape layers where the upper layers are metallized to form the internal circuit traces 282 which contact the wire bond pad 252 of the header block connector assemblies, as previously described in FIG. 57. In this case, the platinum filled via holes 180 are blind holes, in that the platinum does not penetrate all the way through to the top. These blind holes are important in this case, since the high purity alumina substrate 188 now completely surrounds the via holes 180. Electrical continuity is provided from the platinum filled via hole 180 to internal circuit traces 282, which are in turn connected to wire bond pad 252 and to leadwires 118. It will be understood by those skilled in the art that leadwires 118 may be directly routed to implanted lead conductors, to distal electrodes or to header block connector assemblies which facilitate insertion of an implantable lead.

Figure 62:
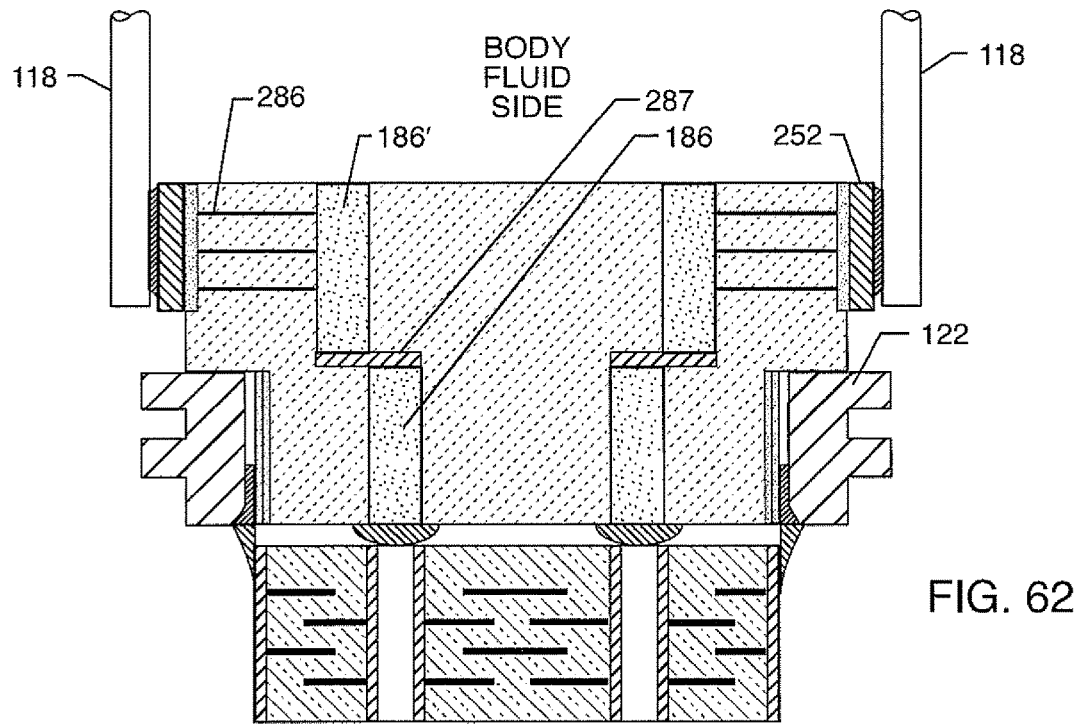
FIG. 62 is a sectional view similar to FIG. 59 now showing a staggered via hole.

FIG. 62 is similar to FIG. 59 except that the platinum conductors 186 and 186' have been staggered. They have a section of circuit trace 287 between the stagger. This is a way of increasing the reliability and the hermeticity of the overall terminal subassembly.

Figure 63:
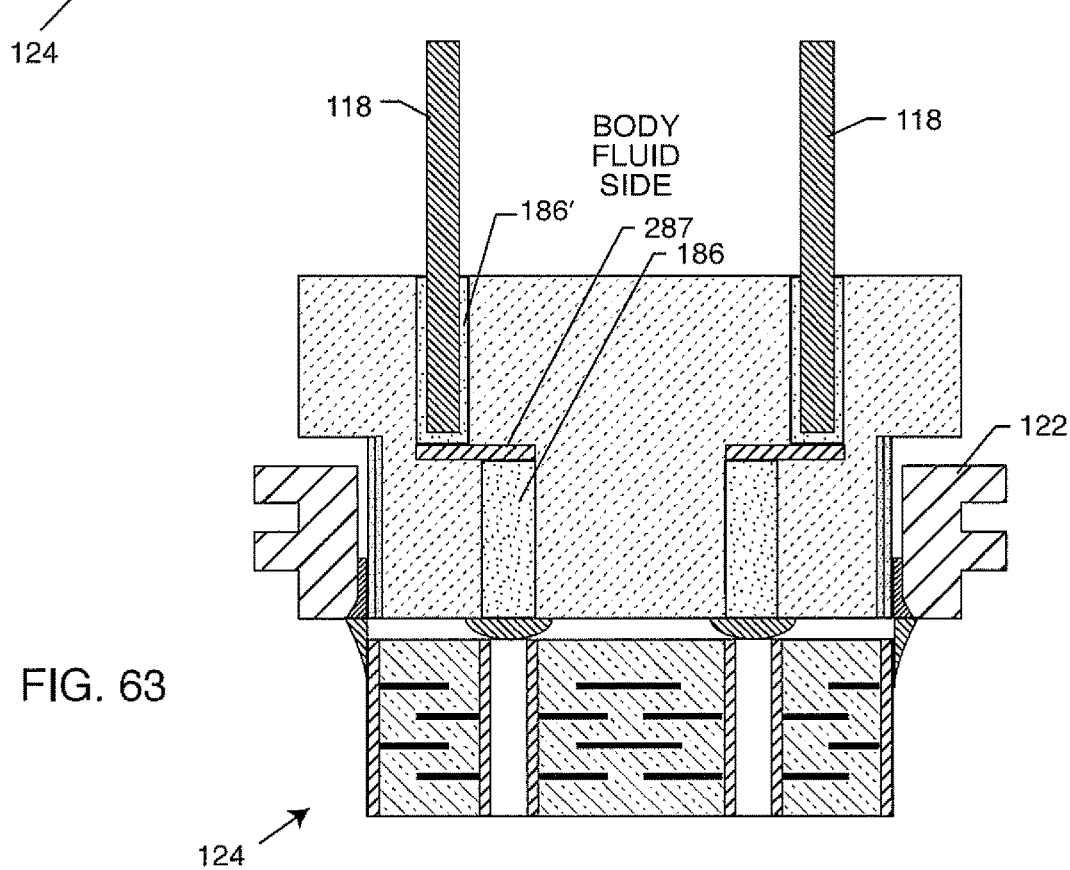
FIG. 63 is a sectional view similar to FIG. 62 now showing a staggered via hole with a solid wire co-fired into the platinum filled via.

FIG. 63 is similar to FIG. 62 in that there are staggered via holes that are filled with pure platinum conductors 186 and 186'. In this case, platinum leadwires 118 have been co-fired into the upper platinum conductors 186'. As previously stated, these leadwires 118 could be routed to implanted leads, to implanted distal electrodes or header block connector assemblies of AIMDs.

Figure 64:
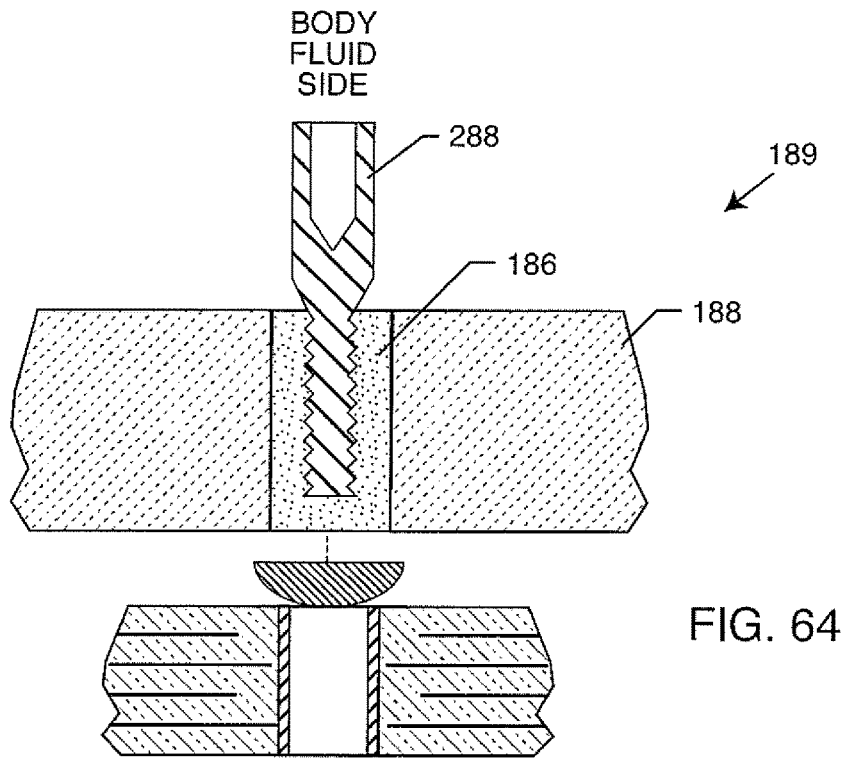
FIG. 64 is a sectional view of an exemplary embodiment of a crimp post co-fired into the platinum filled via.

FIG. 64 illustrates the co-firing of a novel crimp post 288 into the platinum conductor 186. Ideally, the crimp post would be of platinum or similar biocompatible material, which would have a CTE which closely matches that of platinum. A leadwire 118 (not shown) would be inserted into the crimp post and then a mechanical crimping tool would be used to form a mechanical and electrical connection between the walls of the crimp post and the leadwire 118. An optional or supplementary laser weld could also be performed at the point where the leadwire 118 is inserted into the top of the crimp post 288.

Figure 65:
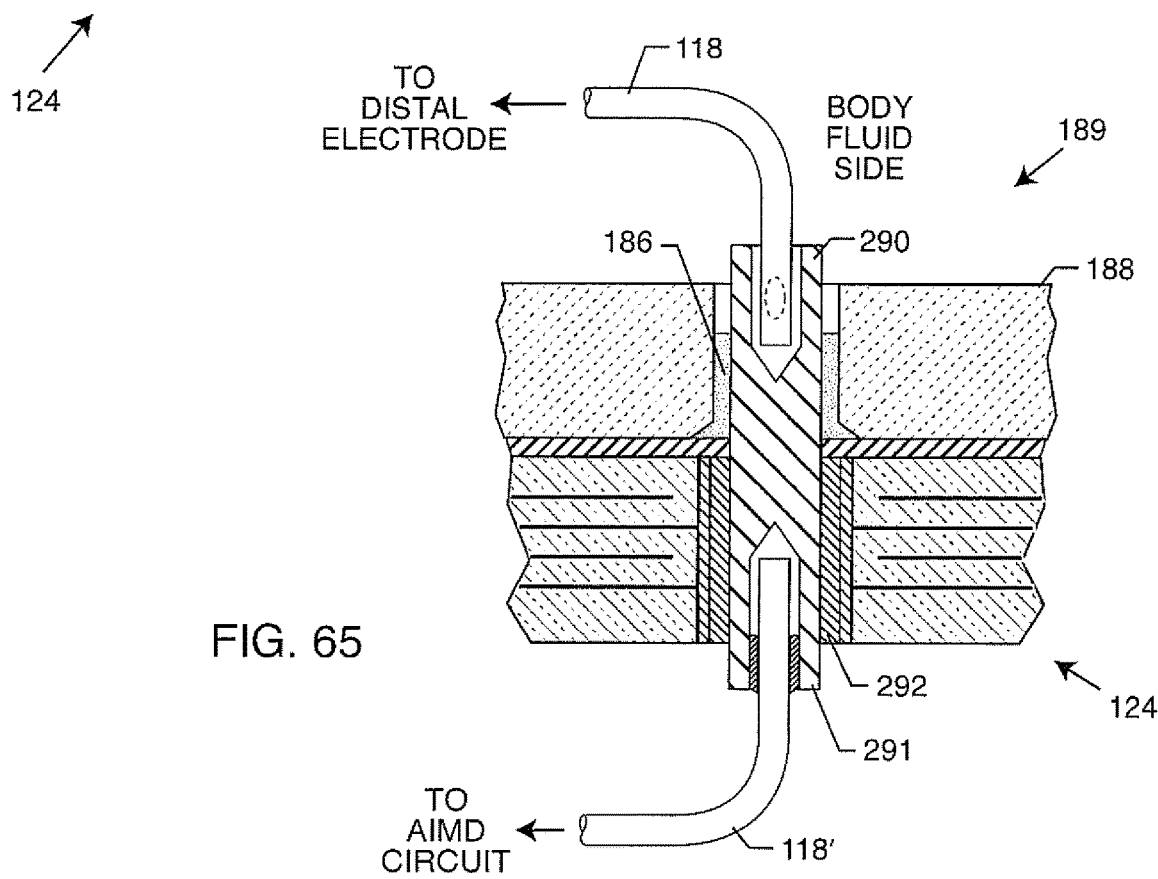
FIG. 65 is a sectional view of an exemplary embodiment of a double crimp post co-fired into the platinum filled via.

FIG. 65 is similar to FIG. 64 but illustrates a double crimp post. On the body fluid side, leadwire 118 is crimped into the crimp post 290 as shown. On the device inside, an internal leadwire 118' can be inserted and crimped into the opposite side 291 of the crimp post 290 to make connection to internal AIMD circuits. As described before, internal leadwire 118' could be an inexpensive copper insulated leadwire or, as in this case, a bare leadwire.

Figure 66:
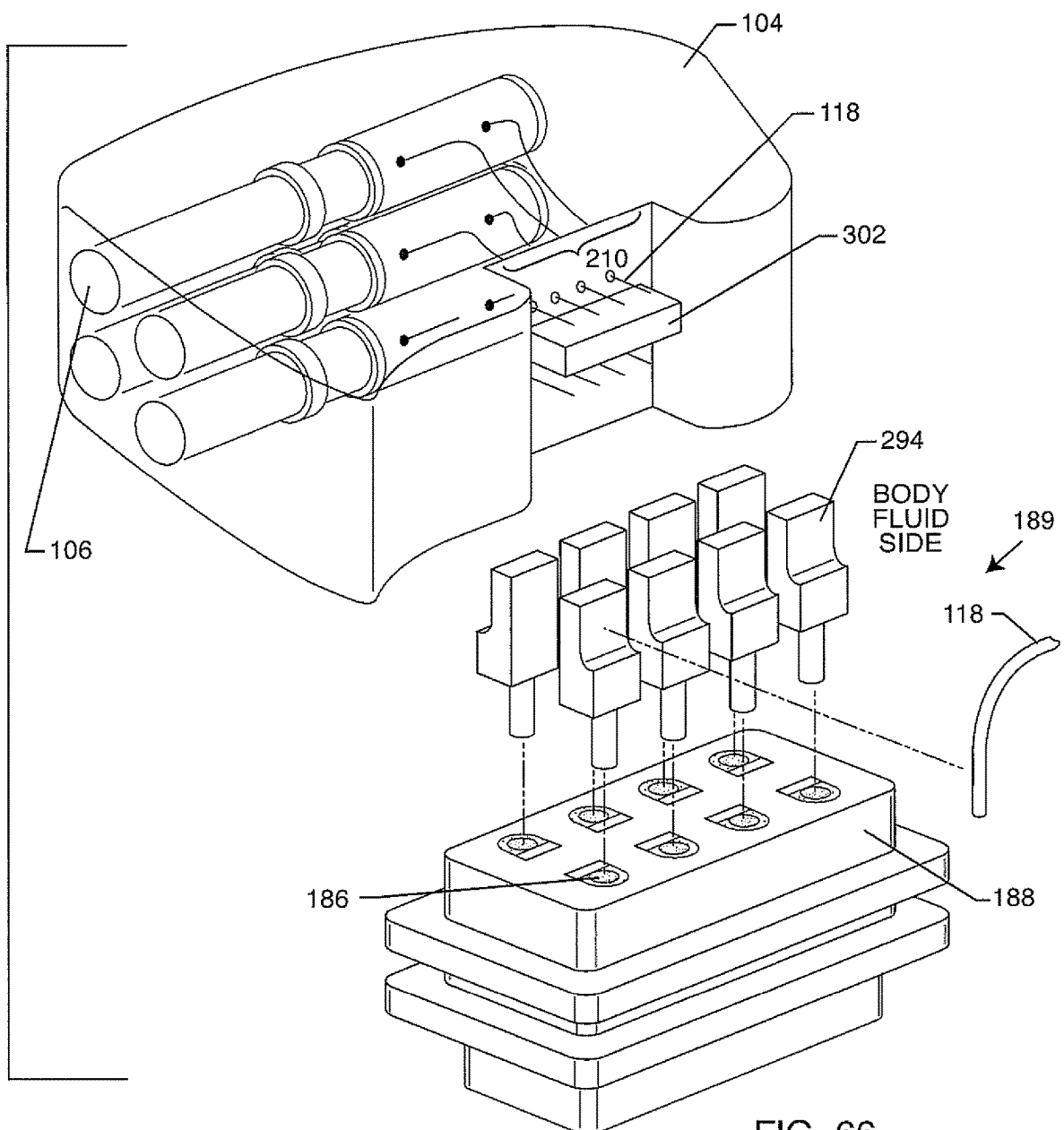
FIG. 66 is a perspective view of an exemplary embodiment of a novel method of header block connector assembly attachment showing a support structure behind the wire bond pads.

FIG. 66 illustrates a novel method of header block connector assembly attachment. The header block connector assembly 104 has been completely prefabricated in accordance with the present invention and has leadwires 118 extending down into a side window 210 of the present invention. Co-molded or co-formed with the header block connector assembly 104 is a support structure 302. The header block connector assembly 104 is shown tilted 90°. There is a co-fired high purity alumina (Al$_2$O$_3$) hermetic terminal subassembly 189 with one or more pure platinum conductors 186 of the present invention with novel wire bond post 294. These wire bond posts 294 each have a leadwire protrusion which are inserted into the via holes and are co-fired with the pure platinum conductor 186. The support structure 302 is designed to slip between the two rows of wire bond posts 294 and provide back support for them. That is, when one pushes against leadwire 118 very firmly with a resistance welder, this will prevent a platinum or equivalent post (which are very ductile) from deforming.

Figure 67:
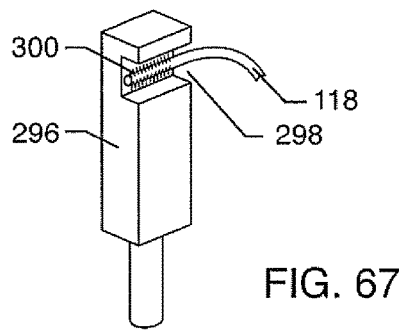
FIG. 67 is a perspective view of a wire bond pad of FIG. 66 with a novel slot.

FIG. 67 illustrates a different type of post 296 which could be used in FIG. 66. Post 296 has a novel slot 298 which can receive a leadwire 118 where a laser weld 300 or the like can be performed.

Figure 68:
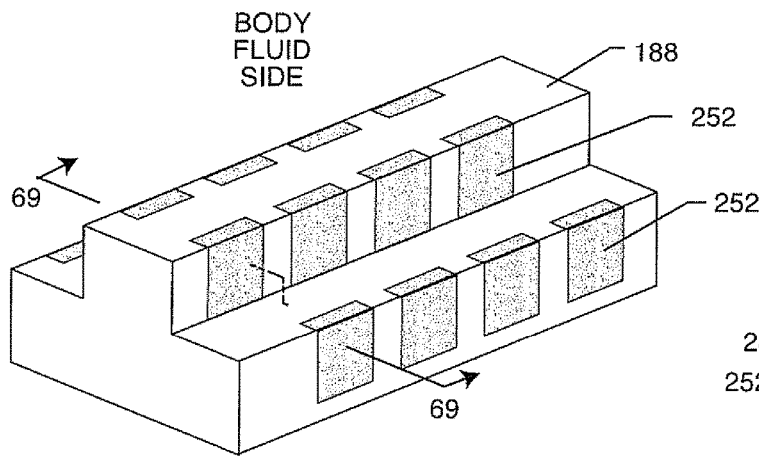
FIG. 68 is a perspective view of an exemplary embodiment of a hermetic terminal subassembly now showing a high density stacking configuration.

FIG. 68 illustrates a layered co-fired high purity alumina (Al.sub.2O.sub.3) hermetic terminal subassembly with one or more filled vias 304 designed for greater connection density in a neurostimulator or other type of AIMD. This type of high density stacking arrangement is particularly useful in conjunction with the window 210 previously described in novel header block connector assembly in FIG. 28.

Figure 69:
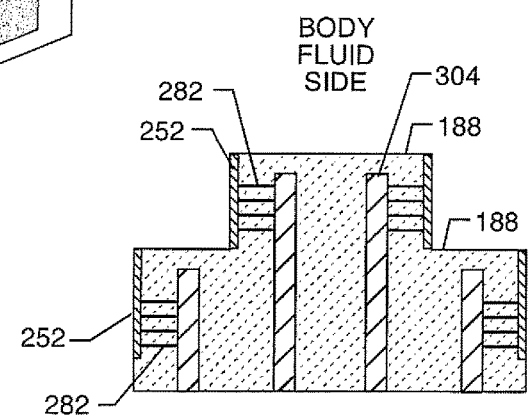
FIG. 69 is a sectional view taken from the structure of FIG. 69 along lines 69-69.

FIG. 69 is a cross-sectional view taken generally from section 69-69 of FIG. 68. FIG. 69 illustrates vias 304 along with internal circuit traces 282 that make contact to the wire bond pad 252 of the header block connector assemblies. It will be appreciated that there is a metallization and gold braze (not shown) that connects the wire bond pads 252 of the header block connector assemblies to the internal circuit traces 282. The body of the co-fired high purity alumina (Al$_2$O$_3$) hermetic terminal subassembly with one or more filled vias 304, as illustrated in FIG. 69, is of high purity alumina substrate 188. The via hole 304 may be filled with pure platinum or a less expensive material, such as tungsten or the like. In this case, the via holes are never exposed to body fluid therefore, less expensive materials can be used. It is important that the internal circuit traces 282 be of platinum or similar biocompatible material since there is some exposure on the body fluid side where the wire bond pads 252 appear. Not shown is a ferrule 122 or means of installing this assembly into a prior art AIMD housing 102. Any of the ferrule or connection structures in any of the previous drawings can, of course, be adapted to the structure illustrated in FIGS. 68 and 69.

Figure 70:
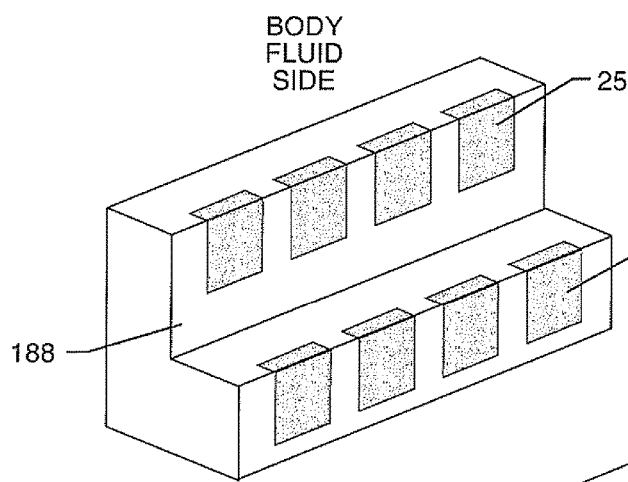
FIG. 70 is a perspective view of another exemplary embodiment of a hermetic terminal subassembly now showing an alternative high density stacking configuration.
Figure 71:
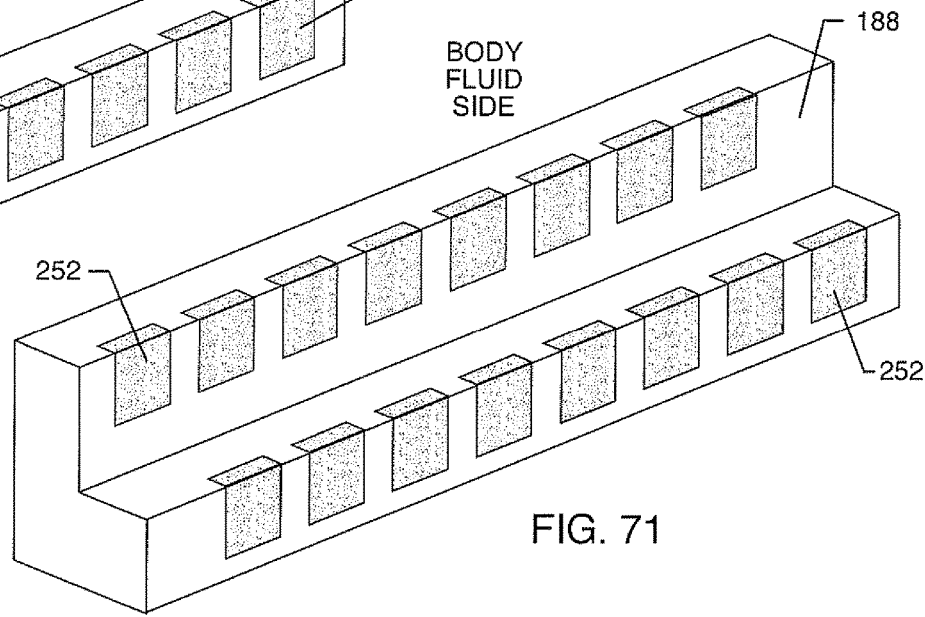
FIG. 71 is a perspective view of another exemplary embodiment of a hermetic terminal subassembly now showing an alternative high density stacking configuration.

FIGS. 70 and 71 are similar to FIG. 68 except that they show alternative stacking methodologies.

Figure 72:
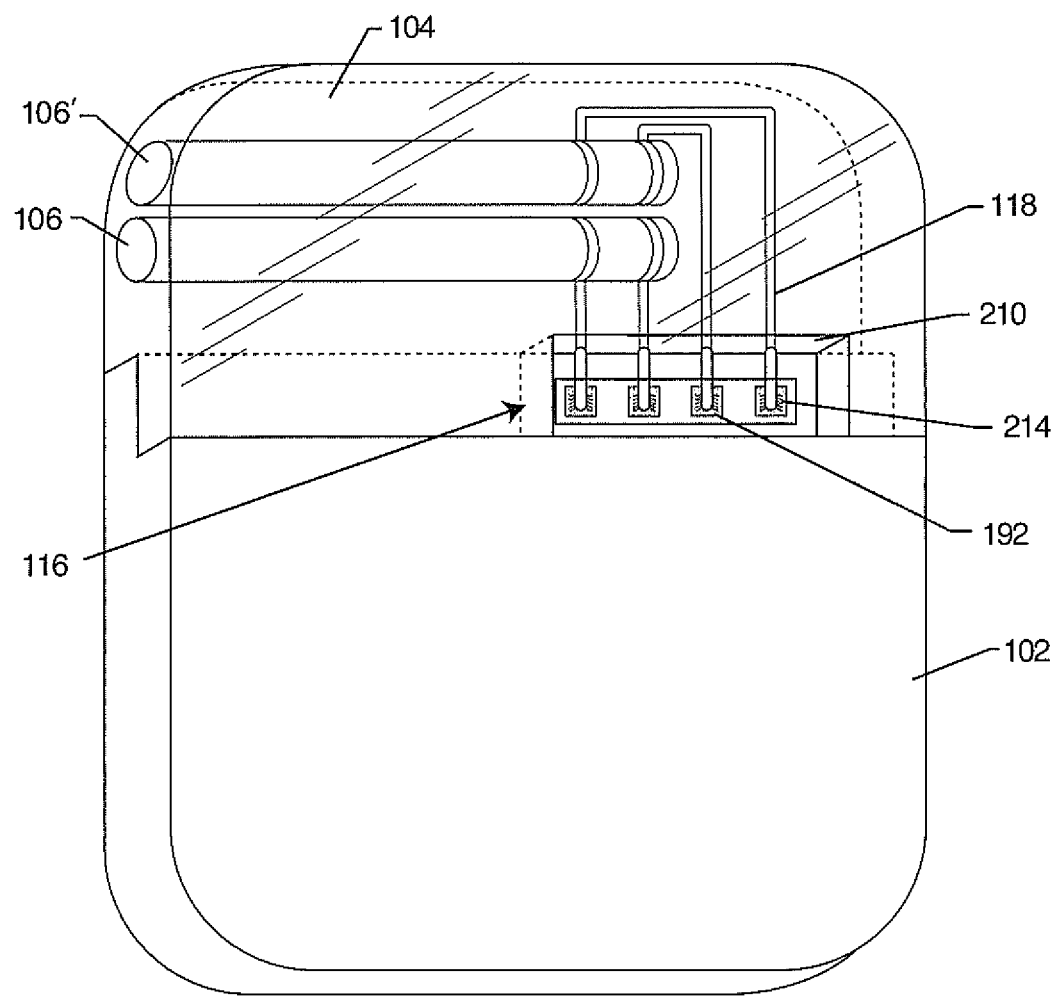
FIG. 72 is a perspective view of an AIMD and header block with a window allowing access to connect the side attachment wire bond pads to the leadwires.

FIG. 72 is similar to FIG. 28 except that the hermetic terminal subassembly of the present invention has a side attachment wire bond pad 192 where leadwires 118 are routed from header block connector port assemblies 106 and 106'. These leadwires 118 are attached by laser welding, or the like, to the side of the hermetic terminal subassembly using electrical attachment material 214.

Figure 73:
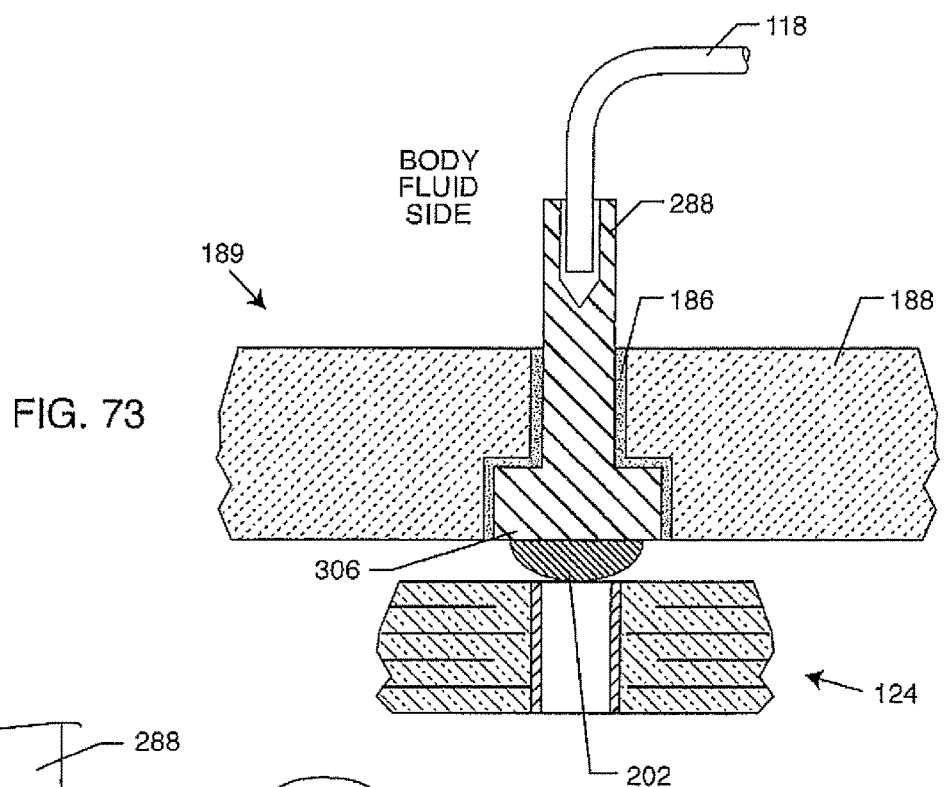
FIG. 73 is a sectional view with a novel crimp post co-fired into the platinum filled via.

FIG. 73 illustrates a co-fired high purity alumina (Al$_2$O$_3$) hermetic terminal subassembly 189 with one or more pure platinum conductors 186 of the present invention with a novel crimp post 288 similar to that previously illustrated in FIGS. 64 and 65. In this case, the crimp post 288 is designed to receive an external leadwire 118 on the body fluid side. On the opposite side is the nail head structure 306, which in this case is radiused. In this case, the crimp post 288 is ideally of platinum or similar material and is co-fired into the platinum conductor 186 in accordance with the present invention. A feedthrough capacitor 124 is attached using a solder BGA 202. It will be obvious to those skilled in the art that any of the BGA attachments as illustrated herein could also be solder dots, solder bumps or dots of thermal-setting conductive adhesives or epoxies, or the like. In a preferred embodiment, the BGA 202 could be of thermal-setting conductive polyimide.

Figure 74:
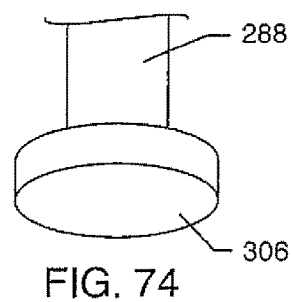
FIG. 74 is a perspective view of another exemplary embodiment of a novel crimp post similar to FIG. 73.
Figure 75:
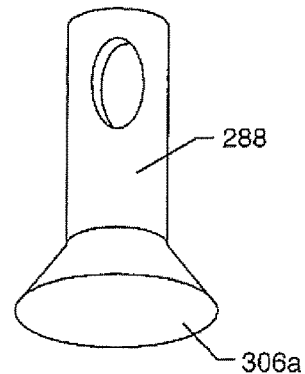
FIG. 75 is a perspective view of another exemplary embodiment of a novel crimp post similar to FIG. 73.
Figure 76:
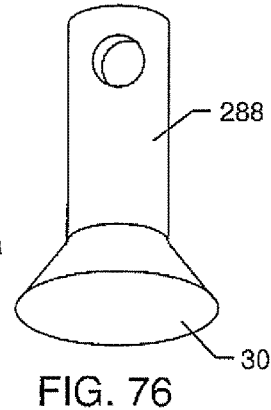
FIG. 76 is a perspective view of another exemplary embodiment of a novel crimp post similar to FIG. 73.
Figure 77:
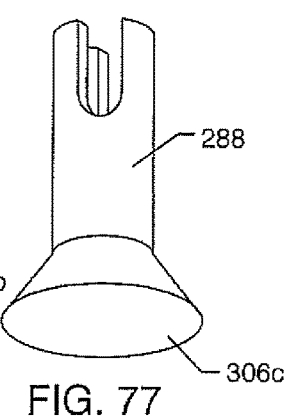
FIG. 77 is a perspective view of another exemplary embodiment of a novel crimp post similar to FIG. 73.
Figure 78:
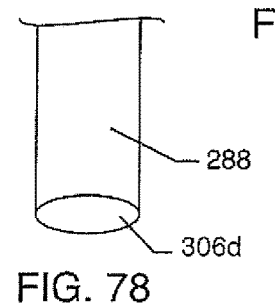
FIG. 78 is a perspective view of another exemplary embodiment of a novel crimp post similar to FIG. 73.

FIGS. 74 through 78 show alternative embodiments of the crimp posts 288 previously illustrated in FIG. 72. FIG. 74 illustrates the end view of the nail head 306 as previously illustrated in FIG. 73. FIGS. 75 through 78 illustrate alternative embodiments of the crimp post 288 having respective nail head ends 306a through 306d.

Figure 79:
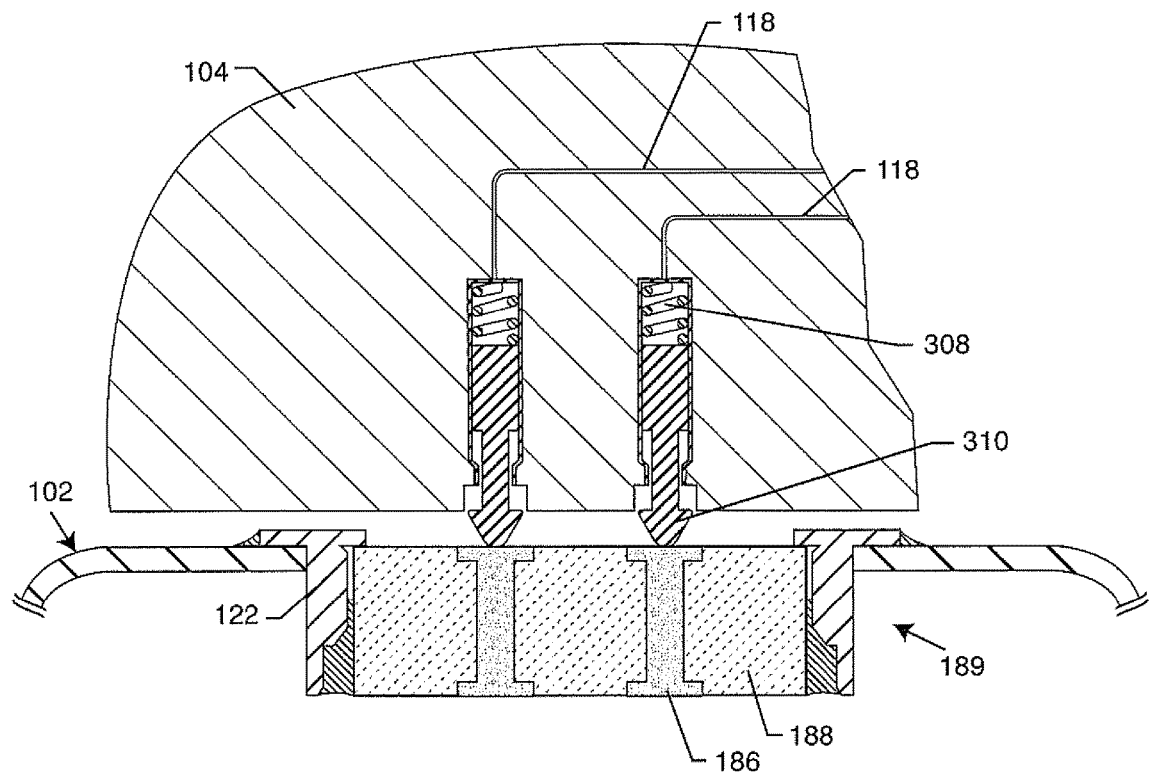
FIG. 79 is a sectional view of an exemplary embodiment of a novel spring electrically connecting the platinum filled via to the leadwires in the header block.

FIG. 79 illustrates a novel header block connector assembly 104 with leadwires 118 routed to connector ports (not shown). Shown are novel springs 308, which push against a contact post 310. Contact posts 310 are designed to be pressed firmly against the novel platinum conductors 186 of the present invention. There is also a methodology of firmly attaching the header block connector assembly 104 to the (pacemaker) AIMD housing 102 (not shown).

Figure 80:
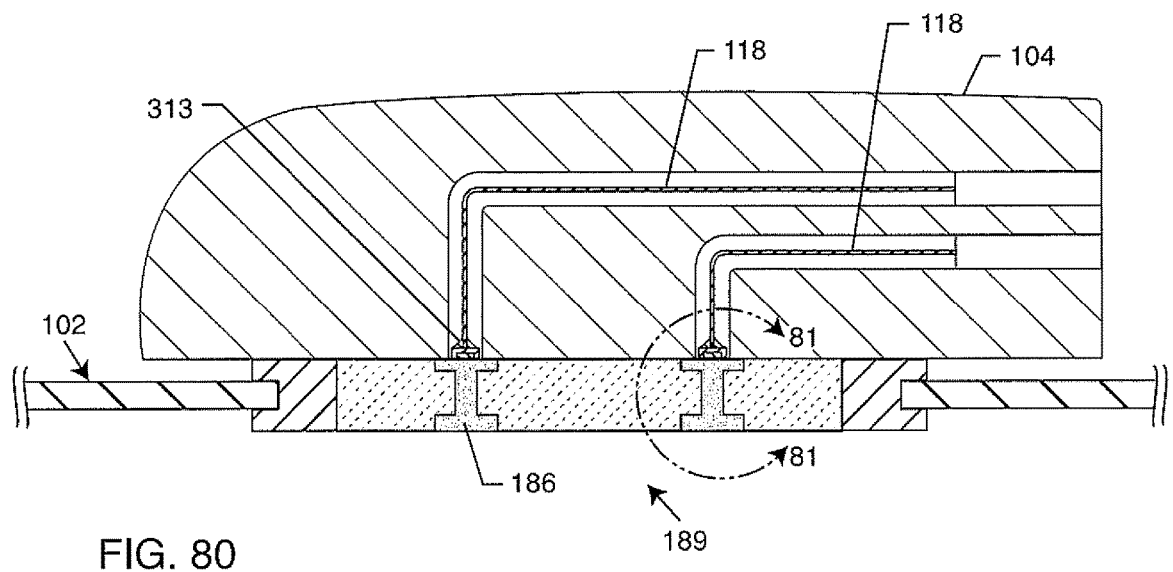
FIG. 80 is a sectional view of another exemplary embodiment of leadwire attachment to the platinum filled vias.
Figure 81:
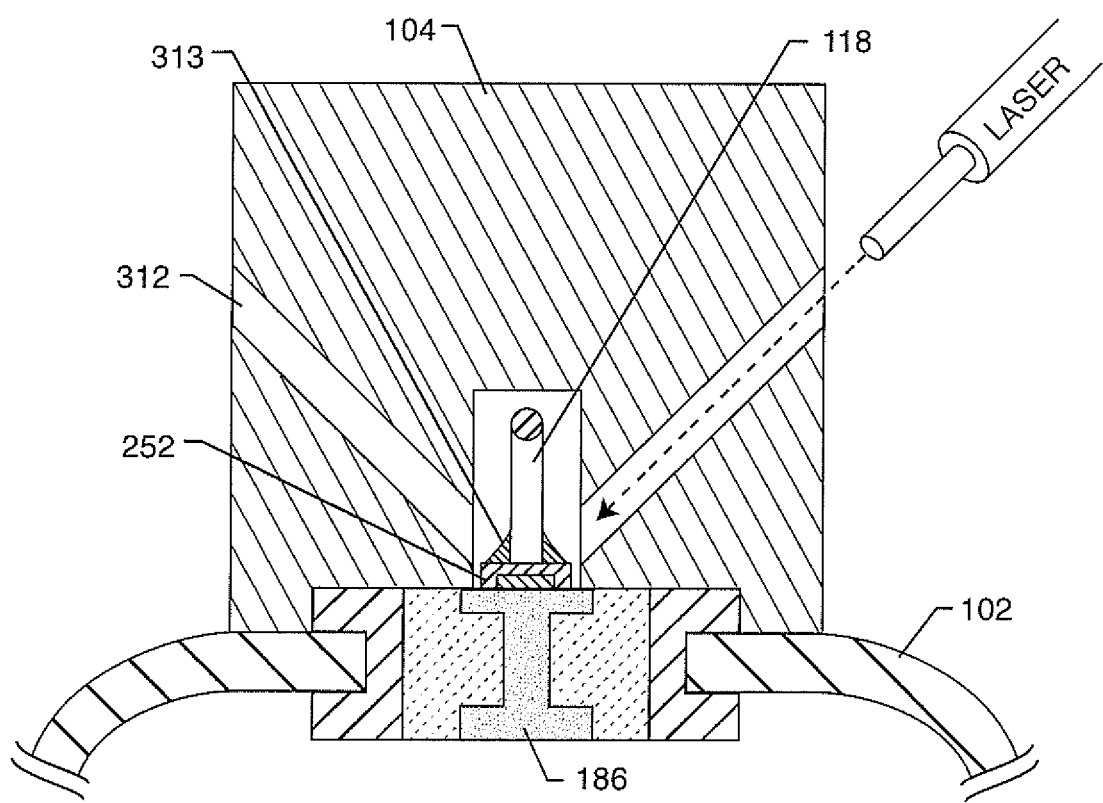
FIG. 81 is a sectional view rotated 90° taken from FIG. 80 along lines 81-81.

FIG. 80 shows an alternative type of novel header block connector assembly 104 with leadwires 118 that are designed to be routed to connectors (not shown). In this case, they are laser welded 313 to the platinum conductors 186. This is better understood by referring to the enlarged drawing FIG. 81, which is taken from section 81-81 of FIG. 80. This view is taken at 90° to the view shown in FIG. 80. As one can see, the AIMD housing 102 is much narrower. In the header block connector assembly 104, there are novel access holes 312 so a laser can be directed and make an electrical connection between the leadwire 118 and the platinum conductors 186. In this case, a wire bond pad and gold braze has been previously attached to the platinum conductor 186 as has been described in previous drawings.

Figure 82:
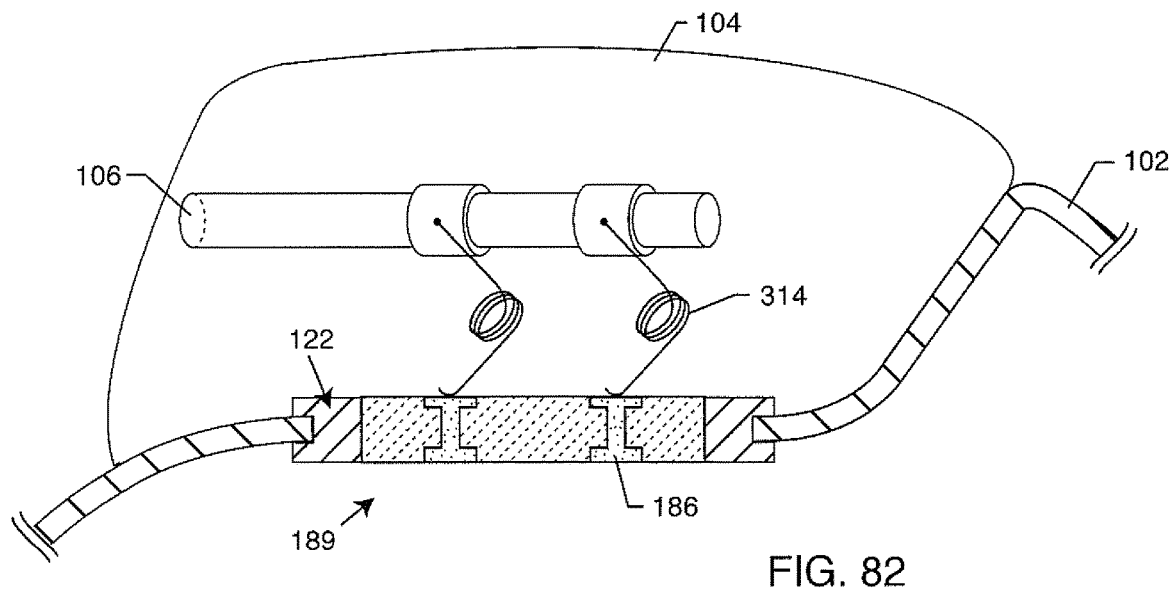
FIG. 82 is a side perspective view of another exemplary embodiment of a novel spring electrically connecting the platinum filled via to the leadwires in the header block.

FIG. 82 illustrates the cross-section of a novel port in the header block connector assembly 104, which is attached to an AIMD housing 102. Shown is a bipolar connector similar to IS-1 or DF-1 header block connector assembly 106. Previous FIG. 3 illustrates a typical prior art header block connector assembly 104 with such header block connector port assemblies 106 and 106'. Novel springs 314 in FIG. 82 make electrical contact to the two terminals of the bipolar connector and also make mechanical and electrical contact against the novel platinum conductor 186 of the present invention.

Figure 83:
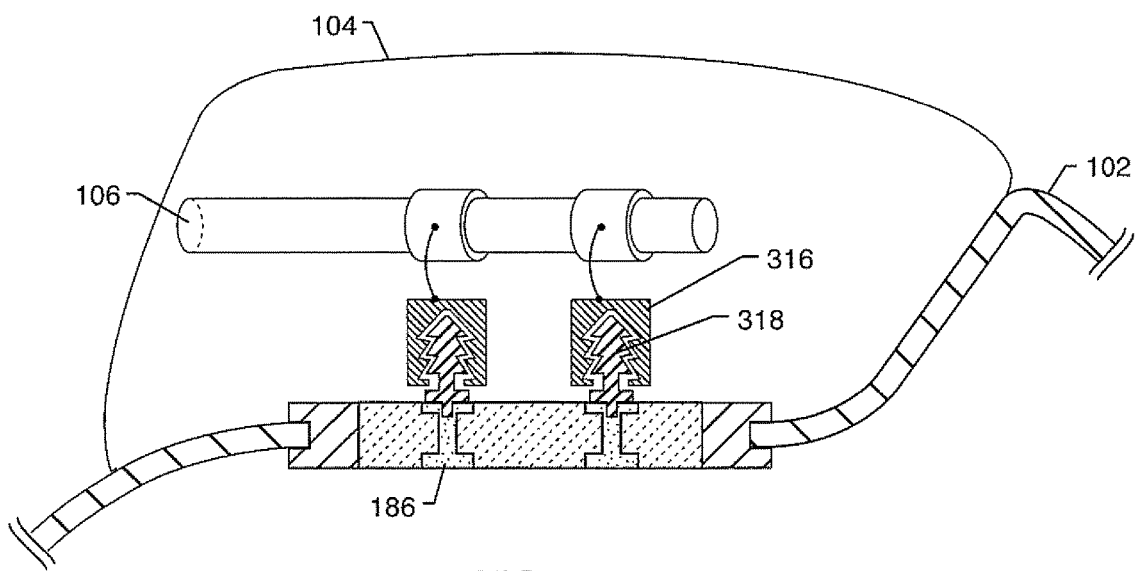
FIG. 83 is a side perspective view of another exemplary embodiment of a novel connector electrically connecting the platinum filled via to the leadwires in the header block.

FIG. 83 is similar to FIG. 82 except that the bipolar connections to the header block connector port assembly 106 are routed to a female push pin header block connector assembly 316. The male push pin header block connector assembly 318 are designed to be firmly inserted into place. The female push pin header block connector assembly 316 is flexed outward as the male push pin header block connector assembly 318 is pushed in so that after insertion, it forms a firm mechanical and electrical connection. The male posts are co-fired into the platinum filled vias of the present invention as shown. The male push pin header block connector assembly 318 and female push pin header block connector assembly 316 must be made from a biocompatible material such as platinum, platinum-iridium, palladium, palladium-iridium alloys, palladium-rhodium alloys or niobium alloys.

Figure 84:
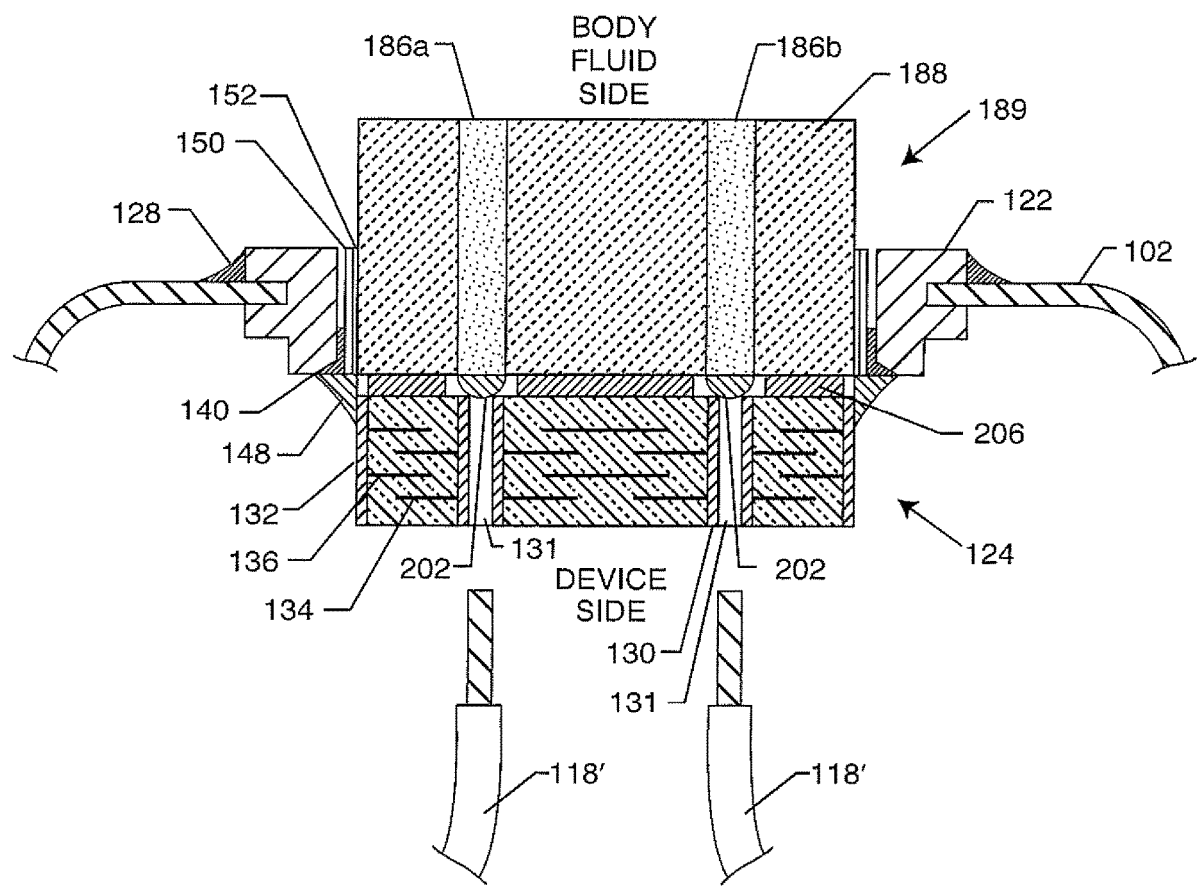
FIG. 84 is another embodiment similar to FIGS. 22 and 23A now showing a sectional view of an exemplary hermetic terminal subassembly with an insulative feedthrough assembly sealed to a ferrule, including a feedthrough capacitor having a bore hole for connection to a leadwire assembly.

FIG. 84 is another embodiment similar to a combination of FIGS. 22 and 23A now showing a sectional view of an exemplary hermetic terminal subassembly 189. The insulative feedthrough body alumina substrate 188 has platinum conductors 186a and 186b. It is understood that the insulative feedthrough body alumina substrate 188 and platinum conductors 186 have been sintered into a rigid structure. The filled via is therefore conductive between the body fluid side (first side) and the device side (second side). The insulative feedthrough has an adhesion layer 152 and wetting layer 150 on an outer surface as previously shown and described. In another embodiment not shown, the wetting and adhesion layers 150 and 152 can also be done with a single layer that both adheres and wets. The insulative feedthrough alumina substrate 188 is then attached at the wetting layer and adhesion layer with connection by a gold braze 140 to the conductive ferrule 122. The gold braze 140 or the like forms a hermetic seal.

The feedthrough capacitor 124 may be attached to the insulative feedthrough alumina substrate 188 by an optional adhesive insulator washer 206 as previously shown and described.

An internal leadwire 118' is connectable to various electronic devices within the AIMD at its proximal end. The distal end of the internal leadwire 118' is then fed through the exposed bore of the capacitor until it touches or is near the device side of the platinum conductors 186. Then the connection material comprising the BGA 202 is used to attach the internal metallization 130 of the capacitor via hole 131 (passageway) to the platinum conductor 186 and the internal leadwire 118'. The connection material comprising the BGA 202 may be a solder BGA structure. It will be known to those skilled in the art that any of the BGA attachments as illustrated herein could also be solder dots, solder bumps or dots of thermal-setting conductive adhesives or epoxies, or the like. In an embodiment, material comprising the BGA 202 could be of thermal-setting conductive polyimide.

Figure 84A:
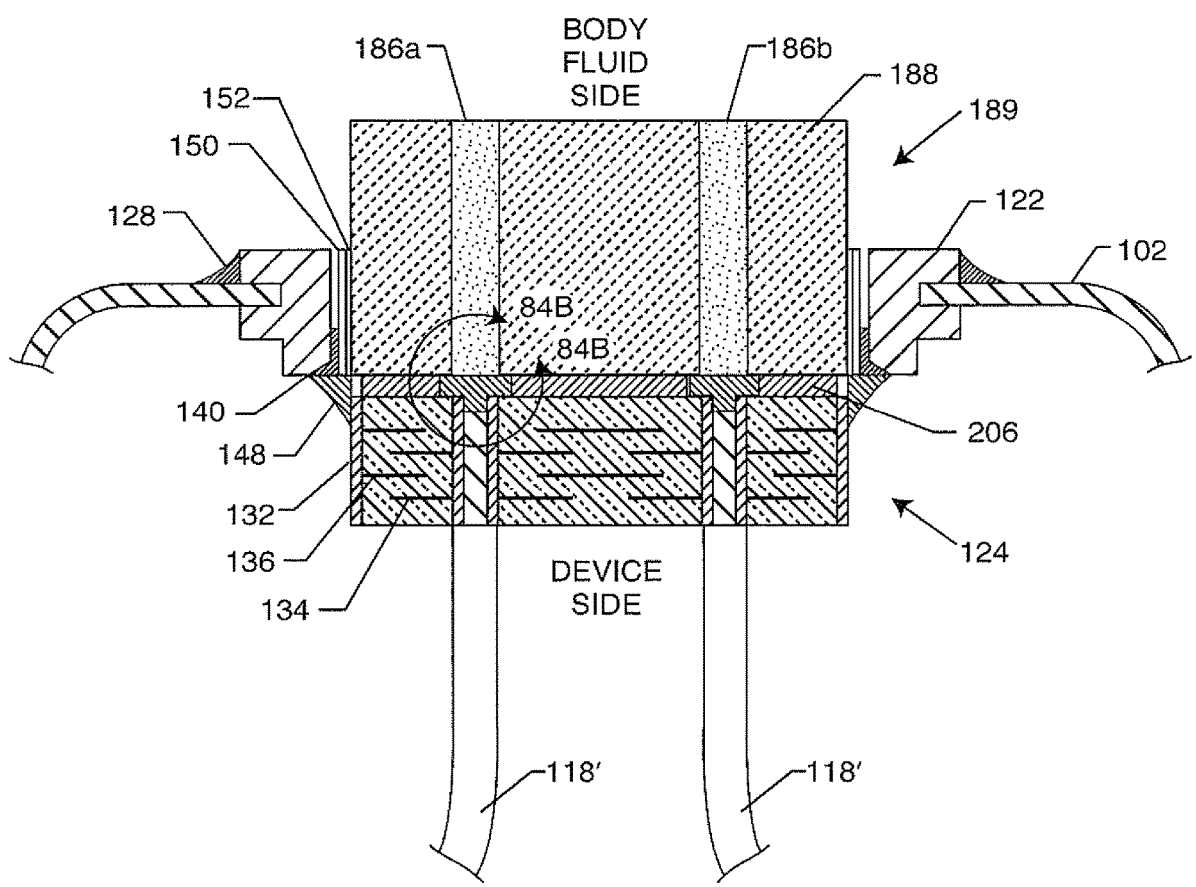
FIG. 84A is a view similar to FIG. 84 now showing the three-way electrical attachment made between the conductive fill, the internal metallization of the feedthrough capacitor and the leadwire assembly.
Figure 84B:
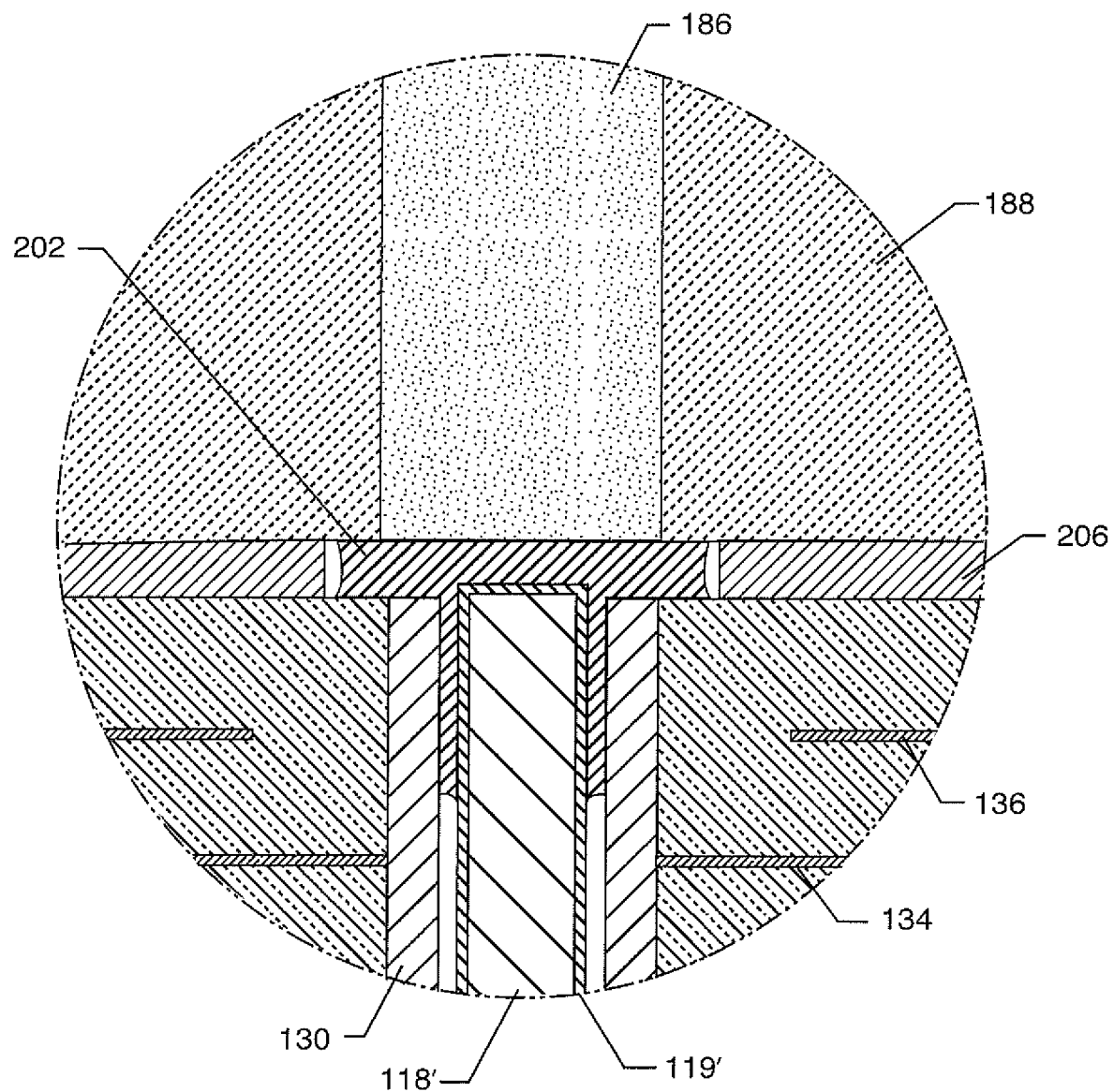
FIG. 84B is an enlarged view of the structure of FIG. 84A taken along lines 84B-84B now showing the pre-tin of the leadwire and the wetting action of the connection material.

One novel feature of this invention is that the connection material comprising the BGA 202 simultaneously connects the conductive platinum conductor 186, the internal leadwire 118' and the internal metallization 130 connected to the active electrode plates all at once. This is best shown in FIGS. 84A and 84B, where the electrical connection material is flowed and makes a three-way electrical connection. In this way a simple and reliable electrical connection is formed in one step between three different structures. None of the prior art embodiments taught, suggested or mentioned such a novel structure.

As shown in FIG. 84 the via hole through the insulator alumina substrate 188 is straight. However, it will be understood by those skilled in the art that the via hole may also be staggered as shown in FIGS. 62 and 63.

As shown in FIG. 84, the external metallization 132 and the electrical connection material 148 extend around the circumference of the feedthrough capacitor 124. However, it will be known to those skilled in the art that it is possible to stagger either of the external metallization 132 and/or the electrical connection material 148 such that it is not continuous around the entirety of the circumference or perimeter. This may result in reduced filtering performance but could still function appropriately. Furthermore, the structure shown in FIG. 84 does not have to be round but could take other shapes such as rectangles and the like.

FIG. 84B is an enlarged view taken from FIG. 84A along lines 84B-84B. The internal leadwire 118' is now showing a pre-tin layer 119'. The pre-tin layer 119' can be made of tin, solder, silver, gold or any material that promotes solder wetting. The layer 119' covers the copper internal leadwire 118' due to coppers unfavorable wetting characteristics. As shown, the connection material comprising the BGA 202 flows down around the internal leadwire 118' to make a strong and reliable electrical and mechanical connection. The solder joint comprising the BGA 202 can now be seen to act in a sheer stress if pulled or tugged, which is stronger than if the connection was merely in tension.

Figure 85:
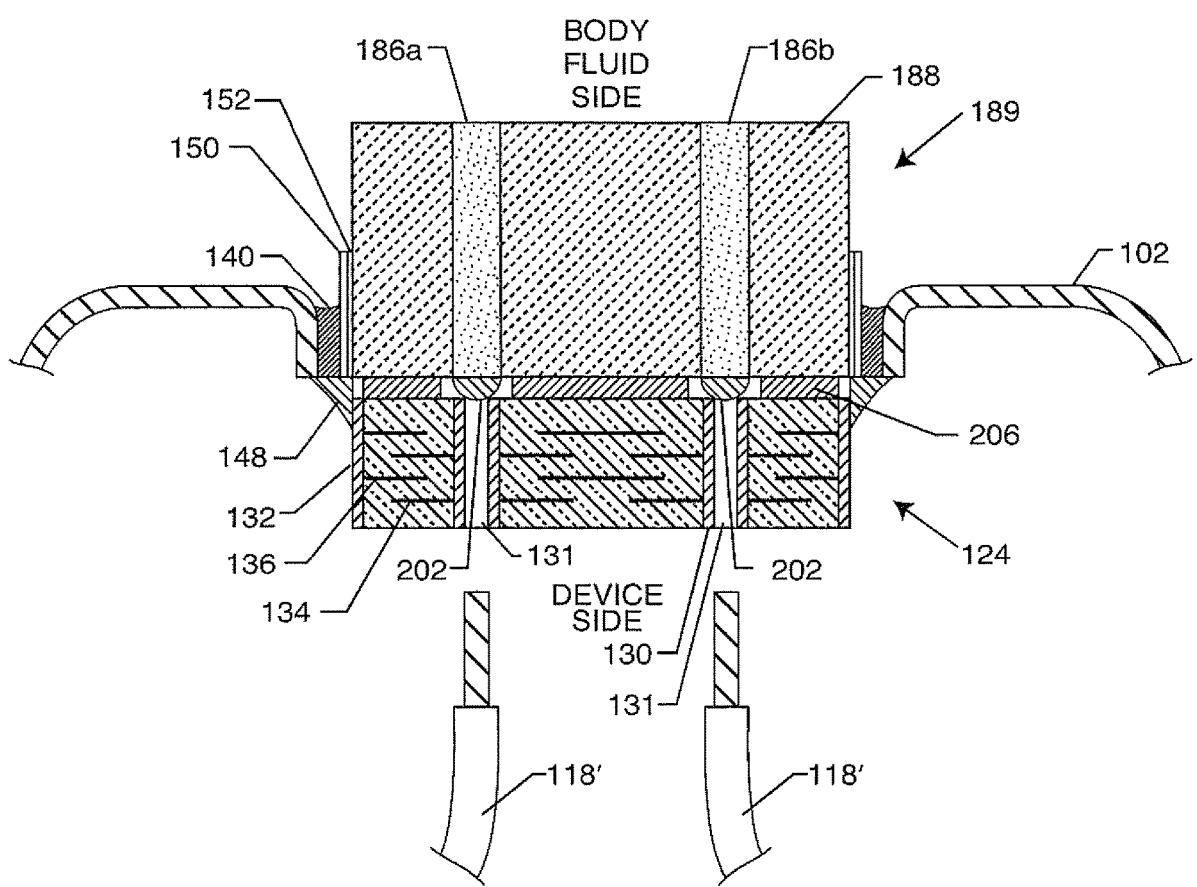
FIG. 85 is another embodiment similar to FIG. 84 showing a sectional view of an exemplary hermetic terminal subassembly now without a ferrule where the insulative feedthrough assembly is sealed to an AIMD housing, and still including a feedthrough capacitor having a bore hole for connection to the leadwire assembly.
Figure 85A:
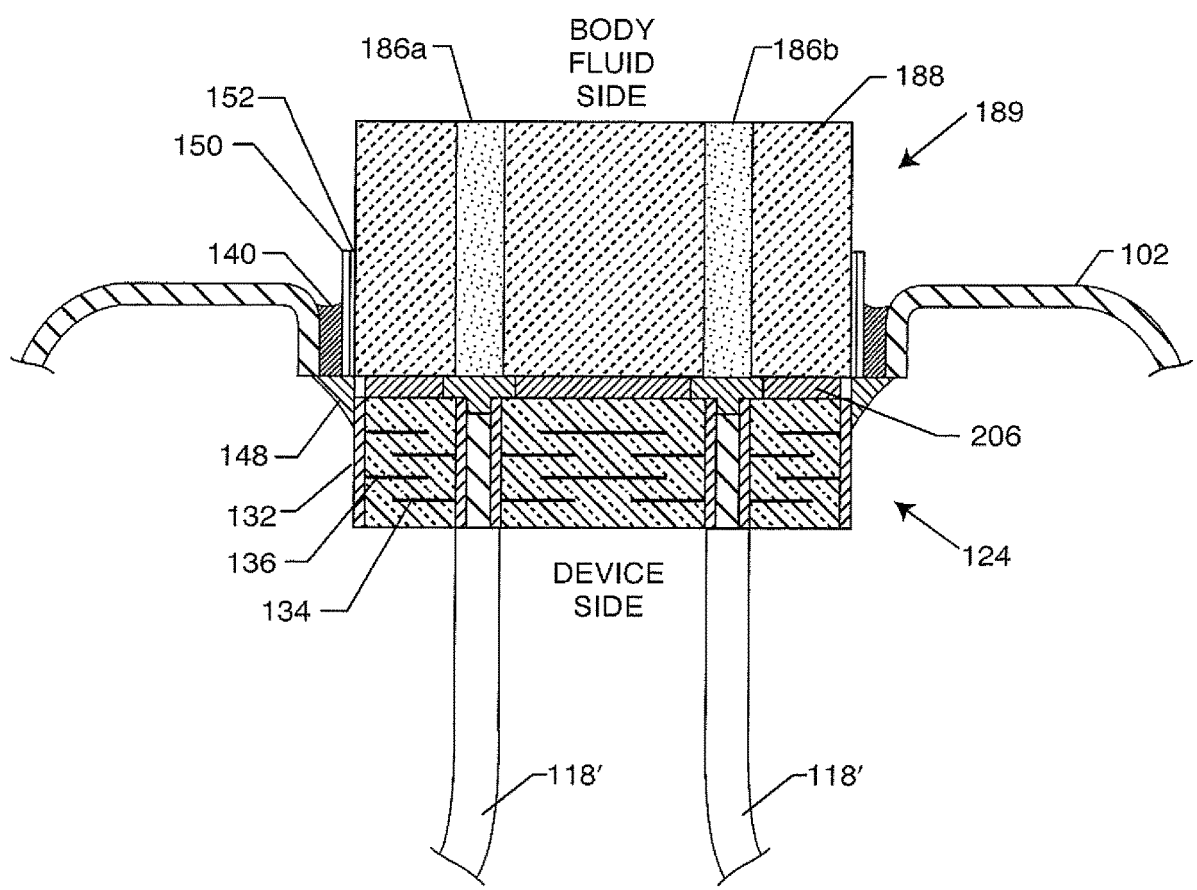
FIG. 85A is a view similar to FIG. 85 now showing the three way electrical attachment between the conductive fill, the internal metallization of the feedthrough capacitor and the leadwire assembly.

FIG. 85 is another embodiment similar to FIG. 84 showing a sectional view of an exemplary hermetic terminal subassembly now without a ferrule. Instead of using ferrule 122, the hermetic terminal subassembly 189 is sealed directly to the AIMD housing 102. This embodiment still includes a feedthrough capacitor 124 having a bore hole (capacitor via) 131 for making the three-way connection to the internal leadwire 118', the conductive platinum conductor 186 and the internal metallization 130 of the feedthrough capacitor 124. FIG. 85A is a view similar to FIG. 85 now showing the three-way electrical attachment of the BGA 202 flowed between the conductive fill, the internal metallization of the feedthrough capacitor and the leadwire assembly.

Figure 86:
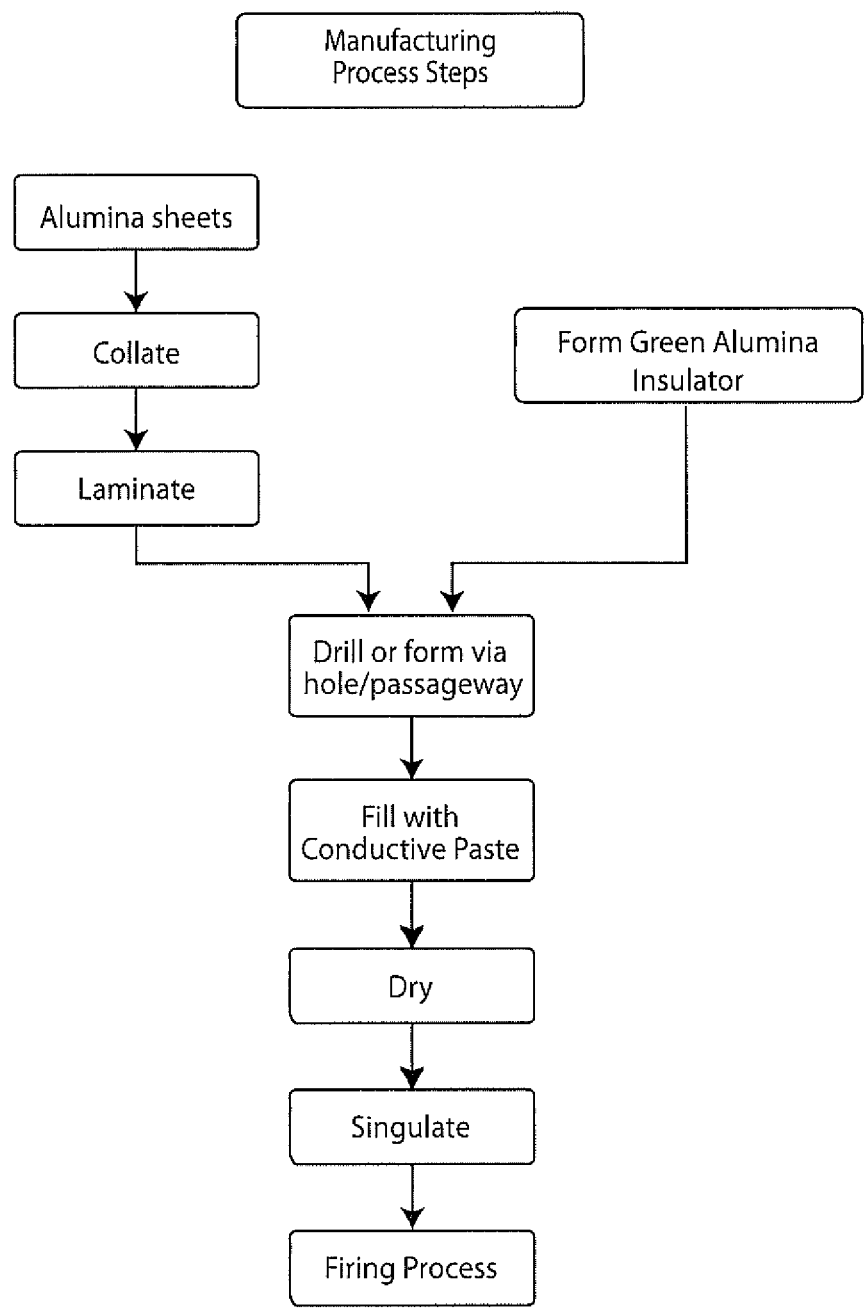
FIG. 86 is a process flow block diagram of a method of manufacturing a conductive feedthrough for a hermetic seal of an AIMD.

FIG. 86 is a process flow block diagram similar to that previously illustrated in FIG. 12 herein. FIG. 86 is reorganized, in that, on the left-side of the process flow block diagram alumina sheets are stacked up and collated and then laminated (i.e. pressed) together to form the insulator alumina substrate 188. On the right-hand side of the process flow block diagram, another way to form the alumina substrate 188 would be to form a green alumina insulator as a monolithic structure. Now referring back to FIG. 12, forming the green alumina substrate 188 may include the steps of injection, molding or green machining of the alumina ($Al_2O_3$) substrate or even using pressed powder. FIG. 86 reorganizes and corrects the former description blocks 166 and 168 from FIG. 12. Step 170, in FIG. 12 says "drill or press-form the via holes." This can still be the case for either side of FIG. 86 in terms of drilling or press forming the via holes. However, emphasis is now made on drilling which includes a step of precision drilling a passageway/via hole. The inventors have learned that precision drilling of a passageway with very sharp tools is important to avoid fractures or splits on the outside diameter of the passageway, which has been found to lead to micro-fracturing during sintering or thermal-shock of the post sintered assembly. The green ceramic bar with drilled or formed passageways can then be filled with conductive paste and then dried and singulated, at which time, the individual singulated insulators are sintered and are then ready for gold brazing into a ferrule.

The drying process in FIG. 86 is simplified (but understood to be the same) from FIG. 12 wherein, in step 174, it says "bake out the solvents and binders at elevated temperature." Referring once again to FIG. 12, step 178 is not shown in FIG. 86, which includes after sintering, sputtering the outside diameter or perimeter of the insulator is performed and then the insulator is gold brazed into a ferrule. However, it is understood that such steps are also performed in regard to FIGS. 86 and 87.

Referring now to FIGS. 13 and 14, one can see in FIG. 13, the right-hand part of FIG. 86, where the green alumina insulator is formed as a single block. FIG. 14 describes the left-hand of FIG. 86, where alumina sheets are stacked, collated and then laminated together. Referring back to FIG. 14, one can see dashed lines separating the various laminated layers $l_1, l_2, \ldots l_n$. After lamination, it is very hard to tell the difference between the monolithic green alumina substrate 188 of FIG. 13 in comparison to the laminated insulator structure of FIG. 14.

Referring once again to FIG. 86, one can see that the via hole or passageway can be drilled or formed.

As used herein, the terms "via hole" and "passageway" may be used interchangeably when referring to the feedthrough hole or via through a hermetic insulator, as described herein.

Figure 87:
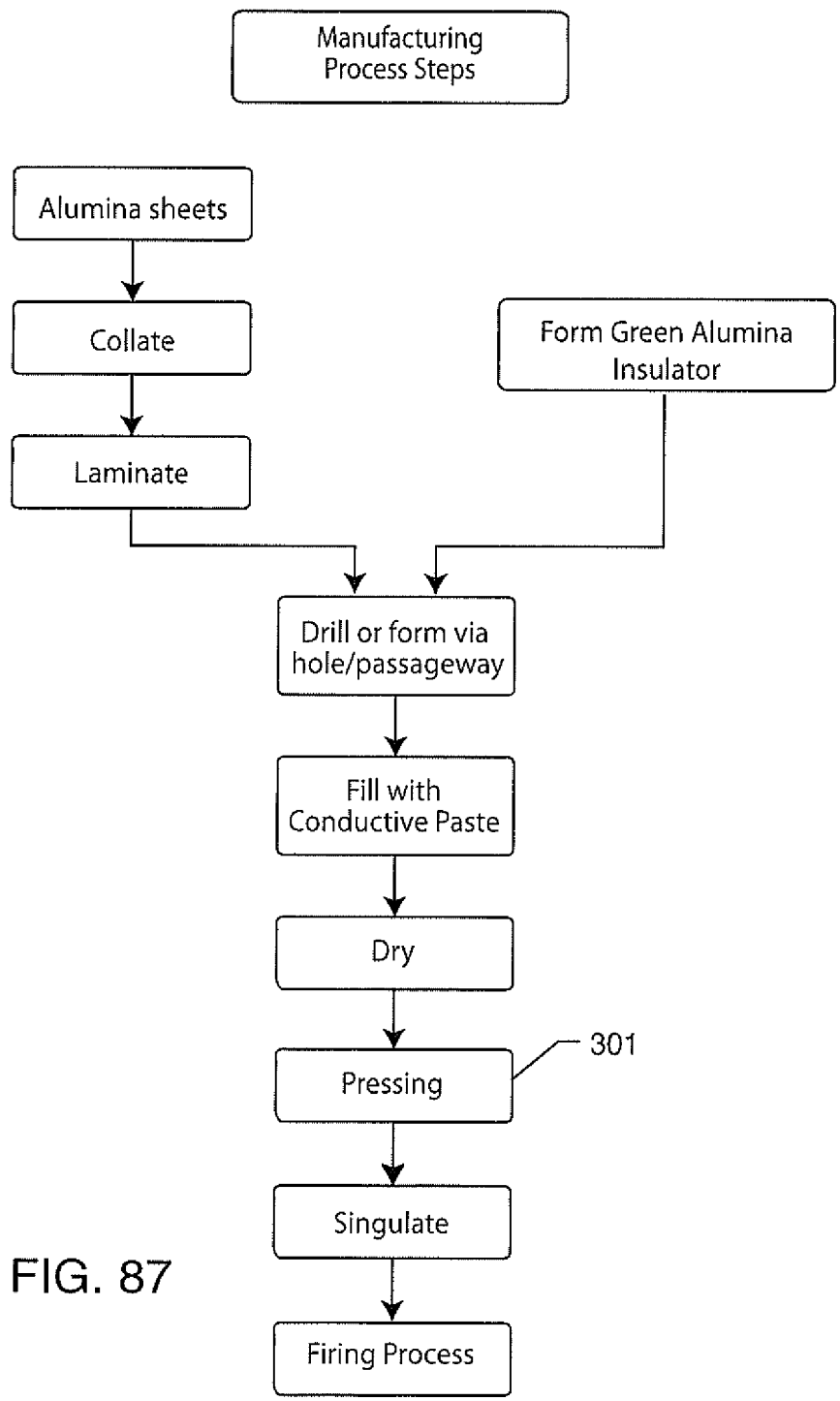
FIG. 87 is a process flow block diagram similar to FIG. 86 now including a novel pressing step for improved hermeticity.

Referring now to FIG. 87, one will see that it is a process flow block diagram identical to that described in FIG. 86, except for the addition of the novel pressing step 301. Pressing step 301 is performed after the via holes (i.e. passageways) are filled with conductive paste and dried. The added pressing step 301 ensures that each via hole is completely packed with conductive paste and that said conductive paste fills every crevasse or tortuous part of a pathway that was formed by drilling or forming of the via hole in the first place.

Referring once again to FIG. 87, step 301, the pressing step is essentially the same as the lamination step described on the left side of the block diagram. The pressing step is an isostatic pressing step applying pressures of approximately 5000 psi into a liquid bath at approximately 85° C. or greater (at least 55° C. or greater) for at least 5 minutes or greater. The isostatic pressing presses the green bar and its conductive paste-filled vias or passageways from all directions. In other words, the green bar is isostatically pressed from the top and bottom and all sides. Some bar deformation could occur during the isostatic pressing. Importantly, after this pressing step 301, the bar is then singulated by milling out the individual hermetic seals from the larger wafer. It is after singulation that each individual hermetic seal (which each can contain many via holes or passageways) is then sintered or fired.

As described, isostatic pressing is a preferred method, but it will also be appreciated that pressing could be accomplished in a variety of alternative processes, particularly, pressing between heated pressure plates or the like. It will also be appreciated that 5000 psi could comprise pressures anywhere from 1000 psi to 50,000 psi. In summary, the added pressing step 301, as illustrated in the FIG. 87 flow chart, is very novel and very important for improved hermeticity and long-term reliability.

Figure 88:
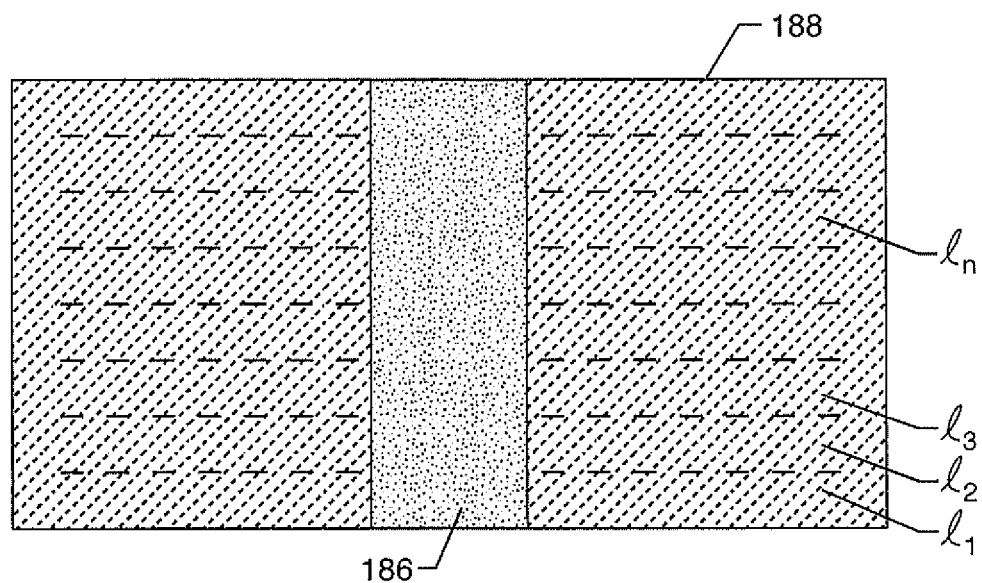
FIG. 88 is a sectional view of a conductive feedthrough in a green state.

Referring now to FIG. 88, one can see what the green bar looks like before pressing. In this case, this is a laminated bar, as described on the left-hand side of the flow chart in FIG. 86. It will be appreciated that the dashed lines can be removed, which would indicate that this could be a formed one-piece green alumina insulator as shown in the right-hand side of FIGS. 86 and 87. Conductive paste comprising the platinum conductor 186 has been filled into the via holes/passageways of the bar, as indicated. Not shown in FIG. 88, is there might be small voids or areas where the substantially pure platinum fill paste comprising the platinum conductor 186 is not in complete and total intimate contact with the outside diameter of the via hole, which comprises the alumina substrate 188.

Figure 89:
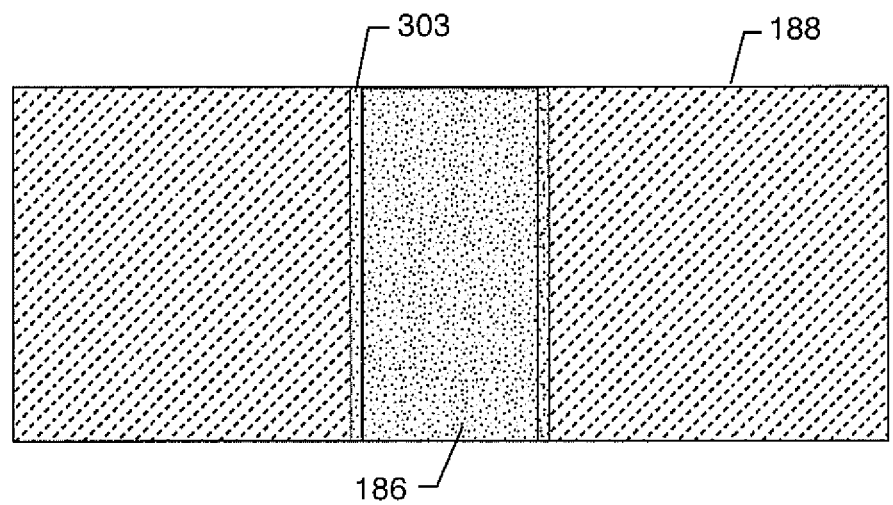
FIG. 89 is a sectional view of the structure of FIG. 88 after the novel pressing step illustrating improved hermeticity between the conductive fill and the insulator dielectric.

FIG. 89 reflects FIG. 88 after the additional pressing step 301, as described in FIG. 87. As illustrated, there is a thin layer 303 of mixing between the paste comprising the pure platinum conductor 186 and the alumina substrate 188. This thin layer 303 is actually a thin intermingling and/or gradient of a mixing of solid particles, which increases particle-to-particle proximity. This particle-to-particle nearness facilitates interface formation during sintering. The thickness of the thin layer 303 is on the order of microns, for example, tens of microns or hundreds of microns. The pressing step is not only sufficient but also necessary for this invention because it is important to have close proximity of the conductive paste (such as platinum) to the alumina particles in the green phase for formation of this thin layer 303 during the sintering step. During sintering, it is this close proximity (namely, while particles are touching one another) that enables formation of an interface layer between the conductive paste (platinum paste) and alumina particles. The inventors discovered that feedthroughs made using the pressing step demonstrate sustainable filled via hole hermeticity. Moreover, in the case when ceramic insulators with conductive paste filled vias are not pressed, hence, a thin intermingling and/or gradient layer does not form, the inventors discovered that during sinter, typically more voids will form between the conductive paste and alumina due to a separation of the alumina from the conductive paste. More specifically, when the via in the alumina is filled with conductive paste and not subsequently pressed, the conductive particles (platinum particles) are not woven in and/or onto the green alumina. This lack of intermingling and/or gradient layer formation subsequently results in a weaker post-sinter interface. The inventors discovered that, when feedthroughs made without pressing were tested, for example, by thermal or pressure shocking of the part, this weakness can be exposed. Subsequent thermal or pressure shocking, it was observed that cracks preferentially follow voids along the interface. Furthermore, it was learned that sustainable hermeticity can be affected when voids at the interface link together, as this linkage can form a leak path along the interface between the alumina and the conductive paste. In summary, formation of the thin layer 303 results in a very strong and sustainably hermetic post-sintered interface between the conductive paste comprising the platinum conductor 186 and the alumina substrate 188.

Although several embodiments have been described in detail for purposes of illustration, various modifications may be made to each without departing from the scope and spirit of the invention. Accordingly, the invention is not to be limited, except as by the appended claims.

What is claimed is:

1. A method for manufacturing a singulated feedthrough insulator for a hermetic seal of an active implantable medical device (AIMD), the method comprising the steps of:
    a) forming a green-state ceramic substrate having a ceramic substrate first side opposite a ceramic substrate second side;
    b) forming at least one via hole extending through the green-state ceramic substrate to the ceramic substrate first and second sides;
    c) filling the at least one via hole with a conductive paste;
    d) following filling step c), drying the green-state ceramic substrate containing the at least one via hole with the conductive paste forming an electrically conductive material filling the at least one via hole in the ceramic substrate;

e) following drying step d), pressing the green-state ceramic substrate comprising the electrically conductive material in the at least one via hole;
f) following pressing step e), singulating at least one green-state insulator from the green-state ceramic substrate, the green-state insulator having an insulator first side opposite an insulator second side; and
g) following singulating step f), sintering the singulated green-state insulator to thereby form an insulator comprising a sintered electrically conductive path extending through the at least one via hole to or adjacent to the insulator first and second sides.

2. The method of claim 1, including forming the green-state ceramic substrate comprising at least 96% percent alumina, by weight or by volume.

3. The method of claim 1, including:
h) providing an electrically conductive ferrule comprising a ferrule opening; and
i) hermetically sealing the insulator to the ferrule in the ferrule opening, wherein the ferrule is configured to be installed in an opening in a housing of an AIMD.

4. The method of claim 3, including providing the ferrule as a separately manufactured component configured to be attachable to an opening of a housing of the AIMD.

5. The method of claim 3, including providing the ferrule as part of the housing of the AIMD.

6. The method of claim 3, including hermetically sealing the insulator to the ferrule using a gold braze.

7. The method of claim 3, including, prior to hermetically sealing the insulator to the ferrule, contacting a wetting metallization to an outer surface of the insulator.

8. The method of claim 7, including providing the wetting metallization comprising niobium.

9. The method of claim 3, including, prior to hermetically sealing the insulator to the ferrule, contacting an adhesion metallization to an outer surface of the insulator, followed by contacting a wetting metallization onto the adhesion metallization.

10. The method of claim 9, including providing the adhesion metallization comprising titanium and the wetting metallization comprising molybdenum or niobium.

11. The method of claim 1, including performing the singulating step f) by milling the green-state insulator from the green-state ceramic substrate.

12. The method of claim 1, including performing the pressing step e) as an isostatic pressing.

13. The method of claim 12, including performing the isostatic pressing at a temperature that is equal to or greater than 55° C.

14. The method of claim 12, including performing the isostatic pressing at a pressure that is from 1,000 psi to 50,000 psi.

15. The method of claim 12, including holding the isostatic pressing at pressure for at least 5 minutes.

16. The method of claim 1, including drying the green-state ceramic substrate containing the at least one via hole filled with the conductive paste in step d) at a temperature of from 400° C. to 700° C.

17. The method of claim 1, including drying the green-state ceramic substrate containing the at least one via hole filled with the conductive paste in step d) by at least one technique selected from the group consisting of waiting a period of time, heating at an elevated temperature, and placing within a vacuum.

18. The method of claim 1, including forming the ceramic substrate in the green state by stacking discrete layers of ceramic in a green state one upon another and laminating them together.

19. The method of claim 1, including providing the conductive paste containing at least 90% metal, by weight or by volume.

20. The method of claim 1, including providing the conductive paste containing at least 90% platinum, by weight or by volume.

21. The method of claim 1, including forming the at least one via hole extending through the green-state ceramic substrate in step b) by at least one technique selected from the group consisting of drilling, punching, machining, laser cutting, and waterjet cutting.

22. The method of claim 1, including performing pressing step e) by at least one technique selected from the group consisting of hot pressing, cold pressing, die pressing, and mechanical pressing.

23. The method of claim 1, including after the sintering step g), removing a thin layer of material from at least one of the insulator first and second sides by at least one technique selected from the group consisting of lapping, grinding, water-cutting, jetting processes and grit-blasting.

24. The method of claim 1, including after the sintering step g), attaching a conductive leadwire to the electrically conductive path at at least one of the insulator first and second sides.

25. The method of claim 24, including attaching the conductive leadwire by a technique selected from the group consisting of ultrasonic welding, thermal sonic bonding, laser welding, arc welding, gas welding, resistance welding, projection welding, butt welding, slash welding, upset welding, solid state welding, friction welding, fusion welding, inductive welding, percussion welding, and electron beam welding.

26. A method for manufacturing a feedthrough insulator for an active implantable medical device (AIMD), the method comprising the steps of:
a) forming a green-state ceramic substrate having a ceramic substrate first side opposite a ceramic substrate second side, the ceramic substrate comprising at least 96% percent alumina, by weight or by volume;
b) forming at least one via hole extending through the green-state ceramic substrate to the ceramic substrate first and second sides;
c) filling the at least one via hole with a conductive paste containing at least 90% platinum, by weight or by volume;
d) following filling step c), drying the green-state ceramic substrate containing the at least one via hole filled with the conductive paste at a temperature of from 400° C. to 700° C. for at least 4 hours to thereby form an electrically conductive material filling the at least one via hole in the ceramic substrate;
e) following drying step d), isostatic pressing the green-state ceramic substrate comprising the electrically conductive material in the at least one via hole at a pressure greater than or equal to 1,000 psi and at a temperature equal to or greater than 55° C. for a time of at least 5 minutes;
f) following pressing step e), singulating at least one green-state insulator from the green-state ceramic substrate, the green-state insulator having an insulator first side opposite an insulator second side;
g) following singulating step f), sintering the singulated green-state insulator to thereby form an insulator comprising a sintered electrically conductive path extending through the at least one via hole to or adjacent to the insulator first and second sides;

h) sputtering an adhesion metallization comprising titanium onto an outer surface of the insulator, followed by sputtering a wetting metallization comprising molybdenum or niobium onto the adhesion metallization;

i) providing an electrically conductive ferrule comprising a ferrule opening, wherein the ferrule is a separately manufactured component that is attachable to an opening of a housing of the AIMD, or wherein the ferrule is formed as a part of the housing of the AIMD; and j) gold brazing the insulator to the ferrule in the ferrule opening.

27. The method of claim 26, including, prior to gold brazing the insulator to the ferrule in the ferrule opening, sputtering an adhesion metallization comprising titanium onto an outer surface of the insulator, followed by sputtering a wetting metallization comprising molybdenum or niobium onto the adhesion metallization.

28. The method of claim 26, including, prior to gold brazing the insulator to the ferrule in the ferrule opening, sputtering a wetting metallization comprising niobium onto an outer surface of the insulator.

* * * * *

UNITED STATES PATENT AND TRADEMARK OFFICE
CERTIFICATE OF CORRECTION

| | | |
|---|---|---|
| PATENT NO. | : 11,351,387 B2 | |
| APPLICATION NO. | : 16/578476 | |
| DATED | : June 7, 2022 | |
| INVENTOR(S) | : Robert A. Stevenson et al. | |

It is certified that error appears in the above-identified patent and that said Letters Patent is hereby corrected as shown below:

In the Specification

Column 41, Line 37, delete "(Al.sub.2O.sub.3)" and insert --($Al_2O_3$)--

Signed and Sealed this
Third Day of January, 2023

Katherine Kelly Vidal
*Director of the United States Patent and Trademark Office*